US012251365B2

(12) United States Patent
Moussa et al.

(10) Patent No.: US 12,251,365 B2
(45) Date of Patent: Mar. 18, 2025

(54) PHARMACEUTICAL FORMULATIONS FOR SUBCUTANEOUS ADMINISTRATION

(71) Applicant: AbbVie Inc., North Chicago, IL (US)

(72) Inventors: Ehab Moussa, Libertyville, IL (US); Matthew Rosebraugh, Grayslake, IL (US); Feroz Jameel, Gurnee, IL (US); Nancy Sever, Northbrook, IL (US); Maurizio F. Facheris, Chicago, IL (US); Weining Z Robieson, Hawthorn Woods, IL (US); Charles S. Locke, Gurnee, IL (US); Sven Stodtmann, Neustadt an der Weinstrasse (DE)

(73) Assignees: AbbVie Inc., North Chicago, IL (US); AbbVie Deutschland Gmbh & Co. KG, Wiesbaden (DE)

( * ) Notice: Subject to any disclaimer, the term of this patent is extended or adjusted under 35 U.S.C. 154(b) by 208 days.

(21) Appl. No.: 16/684,874

(22) Filed: Nov. 15, 2019

(65) Prior Publication Data
US 2020/0155578 A1    May 21, 2020

Related U.S. Application Data

(60) Provisional application No. 62/898,214, filed on Sep. 10, 2019, provisional application No. 62/863,093, filed on Jun. 18, 2019, provisional application No. 62/863,113, filed on Jun. 18, 2019, provisional application No. 62/863,101, filed on Jun. 18, 2019, provisional application No. 62/843,945, filed on May 6, 2019, provisional application No. 62/767,546, filed on Nov. 15, 2018.

(51) Int. Cl.
*A61P 25/16* (2006.01)
*A61K 9/00* (2006.01)
*A61K 31/198* (2006.01)
*A61K 31/661* (2006.01)

(52) U.S. Cl.
CPC .......... *A61K 31/198* (2013.01); *A61K 9/0019* (2013.01); *A61K 31/661* (2013.01); *A61P 25/16* (2018.01)

(58) Field of Classification Search
CPC .. A61K 9/0019; A61K 31/661; A61K 31/198; A61P 25/16
See application file for complete search history.

(56) References Cited

U.S. PATENT DOCUMENTS

| 3,132,171 | A | 5/1964 | Plaut |
| 3,891,696 | A | 6/1975 | Bodor et al. |
| 3,939,253 | A | 2/1976 | Bodor et al. |
| 3,998,799 | A | 12/1976 | Bodor et al. |
| 4,035,507 | A | 7/1977 | Bodor et al. |
| 4,065,566 | A | 12/1977 | Bodor et al. |
| 4,163,058 | A | 7/1979 | Stella et al. |
| 4,508,706 | A | 4/1985 | Pawelek et al. |
| 4,618,484 | A | 10/1986 | Pawelek |
| 4,673,671 | A | 6/1987 | Casagrande et al. |
| 5,013,753 | A | 5/1991 | Casagrande et al. |
| 5,073,547 | A | 12/1991 | Casagrande et al. |
| 5,438,047 | A | 8/1995 | Santangelo et al. |
| 5,635,213 | A | 6/1997 | Nystrom et al. |
| 5,874,468 | A * | 2/1999 | Atlas ............... A61K 31/16 562/556 |
| 6,204,257 | B1 | 3/2001 | Stella et al. |
| 6,365,180 | B1 | 4/2002 | Meyer et al. |
| 6,576,766 | B1 | 6/2003 | Weigele et al. |
| 6,872,838 | B2 | 3/2005 | Stella et al. |
| 8,048,926 | B2 | 11/2011 | Atlas |
| 8,557,239 | B2 | 10/2013 | Valdes et al. |
| 8,709,485 | B2 * | 4/2014 | Talwar ............ A61K 31/198 514/521 |
| 8,747,854 | B2 | 6/2014 | Okun et al. |
| 9,446,059 | B2 * | 9/2016 | Cardinal-David .... C07C 281/02 |
| 10,117,843 | B2 | 11/2018 | Conjeevaram et al. |
| 10,174,061 | B2 | 1/2019 | Cardinal-David et al. |
| 10,258,585 | B2 | 4/2019 | Yacoby-Zeevi |
| 10,730,895 | B2 | 8/2020 | Kym et al. |
| 11,091,507 | B2 | 8/2021 | Enright et al. |
| 11,213,502 | B1 | 1/2022 | Birnberg et al. |
| 11,331,293 | B1 | 5/2022 | Birnberg et al. |
| 2005/0282891 | A1 | 2/2005 | Hakamiun |

(Continued)

FOREIGN PATENT DOCUMENTS

CN  1845728 A   10/2006
EA  014576 B1   12/2010

(Continued)

OTHER PUBLICATIONS

Rebecca Gilbert (Predictors of motor complications in early Parkinson's disease. American Parkinson's Disease Association (Jan. 2024). https://www.apdaparkinson.org/wp-content/uploads/2022/05/APDA23371A-Motor-Fluctuations-Fact-Sheet_ENG_D2FA_ForWeb.pdf. 2 pages.) (Year: 2024).*

Abbvie Limited, "Duodopa intestinal gel - Summary of product characteristics (SPC)—(eMX)." https://www.medicines.org.uk/emc/medicine/20786/SPC/Duodopa+intestinal+gel/#COMPOSITION (2013).

Adar et al.,. "Continuous Administration of Subcutaneous Levodopa/Carbidopa (ND0612) Demonstrated Comparable Levodopa Pharmacokinetics to Levodopa/Carbidopa Intestinal Gel (LCIG) (S4.003)," Neurology, 88, Supplement 16 Abstract (2017).

Adar et al., "Pharmacokinetic profile of continuous levodopa/carbidopa delivery when administered subcutaneously (ND0612) versus duodenal infusion (levodopa/carbidopa intestinal gel)," International Parkinson and Movement Disorder Society—Meeting Abstracts, Abstract No. 1337 (2017).

(Continued)

*Primary Examiner* — Amanda L. Aguirre
*Assistant Examiner* — Chris E Simmons
(74) *Attorney, Agent, or Firm* — Foley Hoag LLP; Hathaway P. Russell; Benjamin A. Vaughan

(57) ABSTRACT

The present disclosure relates to compositions of levodopa 4'-monophosphate and carbidopa 4'-monophosphate having a weight by weight ratio of about 20:1 and methods of treating Parkinson's disease and associated conditions by subcutaneous administration of such compositions.

36 Claims, 26 Drawing Sheets

(56) References Cited

U.S. PATENT DOCUMENTS

| | | | |
|---|---|---|---|
| 2012/0288446 | A1 | 11/2012 | Garigapati et al. |
| 2013/0253056 | A1 | 9/2013 | Nemas et al. |
| 2014/0088192 | A1 | 3/2014 | Heller et al. |
| 2014/0187630 | A1 | 7/2014 | Kokubo et al. |
| 2014/0221489 | A1 | 8/2014 | Dizdar Segrell |
| 2016/0022573 | A1 | 1/2016 | Yacoby-Zeevi |
| 2016/0106765 | A1 | 4/2016 | Cardinal-David et al. |
| 2016/0362431 | A1 | 12/2016 | Cardinal-David et al. |
| 2018/0079762 | A1 | 3/2018 | Cardinal-David et al. |
| 2019/0224153 | A1 | 7/2019 | Tack et al. |
| 2019/0224220 | A1 | 7/2019 | Kym et al. |
| 2019/0375770 | A1 | 12/2019 | Cardinal-David et al. |
| 2020/0155578 | A1 | 5/2020 | Moussa et al. |
| 2020/0262852 | A1 | 8/2020 | Cardinal-David et al. |
| 2022/0153765 | A1 | 5/2022 | Cardinal-David et al. |
| 2023/0106081 | A1 | 4/2023 | Cardinal-David et al. |
| 2024/0024338 | A1 | 1/2024 | Cardinal-David et al. |
| 2024/0100072 | A1 | 3/2024 | Facheris et al. |

FOREIGN PATENT DOCUMENTS

| | | | |
|---|---|---|---|
| EA | 201290865 A1 | 2/2013 | |
| EP | 0216881 A1 | 4/1987 | |
| EP | 0309827 A1 | 4/1989 | |
| EP | 0393781 A2 | 10/1990 | |
| JP | 2007/504143 A | 3/2007 | |
| JP | 2007/509972 A | 4/2007 | |
| JP | 2008/505898 A | 2/2008 | |
| JP | 2013/545745 A | 12/2013 | |
| RU | 2365580 C2 | 8/2009 | |
| RU | 2429223 C2 | 9/2011 | |
| RU | 2484815 C2 | 6/2013 | |
| RU | 2485947 C2 | 6/2013 | |
| RU | 2559083 C2 | 8/2015 | |
| WO | WO-92/13868 A1 | 8/1992 | |
| WO | WO-94/03461 A1 | 2/1994 | |
| WO | WO-00/08033 A1 | 2/2000 | |
| WO | WO-2004/000863 A1 | 12/2003 | |
| WO | WO-2004/052841 A1 | 6/2004 | |
| WO | WO-2006/014282 A2 | 2/2006 | |
| WO | WO-2008/076458 A1 | 6/2008 | |
| WO | WO-2009/007696 A1 | 1/2009 | |
| WO | WO-2009/143295 A1 | 11/2009 | |
| WO | WO-2010/134074 A1 | 11/2010 | |
| WO | WO-2011/056240 A2 | 5/2011 | |
| WO | WO-2011/107653 A2 | 9/2011 | |
| WO | WO-2011/109767 A2 | 9/2011 | |
| WO | WO-2012/066538 A1 | 5/2012 | |
| WO | WO-2012/079072 A2 | 6/2012 | |
| WO | WO-2014/139161 A1 | 9/2014 | |
| WO | WO-2016/065019 A1 | 4/2016 | |
| WO | WO-2017/184871 A1 | 10/2017 | |
| WO | WO-2018/059739 A1 | 4/2018 | |
| WO | WO-2018/154447 A1 | 8/2018 | |
| WO | WO-2023/049534 A2 | 3/2023 | |
| WO | WO-2023/049534 A3 | 7/2023 | |

OTHER PUBLICATIONS

Agin et al., "Phosphorylated mixed isomers of L-dopa increase melanin content in skins of Skh-2 pigmented hairless mice," Pigment Cell Research, 1:137-142 (1987).

Benet et al., "Basic Principles of Pharmacokinetics," Toxicologic Pathology, 23(2): 115-123 (1995).

Cooper et al., "L-Dopa esters as potential prodrugs: Behavioural activity in experimental models of Parkinson's disease," Journal of Pharmacy and Pharmacology, 39(8):627-635 (1987).

Dauer et al., "Parkinson's Disease: Mechanisms and Models", Neuron, 39: 889-909 (2003).

De Lau et al., "Epidemiology of Parkinson's Disease," The Lancet Neurology, 5(6): 525-535 (2006).

Dhareshwar et al., "Prodrugs Releasing Formaldehyde in Vivo," Journal of Pharmaceutical Sciences, 97(10): 4184-4193 (2008).

Dhareshwar et al., "Your prodrug releases formaldehyde: Should you be concerned? No!," Journal of Pharmaceutical Sciences 97(10):4184-4193 (2008).

Ervin et al., "Dietary intake of selected minerals for the United States population: 1999-2000," Advanced Data, 341: 6 pages (2004).

Extended European Search Report for EP Application No. 3569587 dated Oct. 9, 2019.

Facheris et al., "Safety and Tolerability During a 4-Week Continuous Subcutaneous Infusion of ABBV-951, a New Drug Formulation for the Treatment of Parkinson's Disease: Final Results of a Phase 1b Study (1384)," Neurology, 94, 15 Supplement Abstract (2020).

Facheris et al., "Safety and Tolerability in Parkinson's Disease Patients Treated with a Continuous Subcutaneous Infusion of ABBV-951: Design of a 52-Week Phase 3 Study (4233)," Neurology, 94, 15 Supplement (2020).

Freitas et al., "Novel Levodopa Formulations for Parkinson's Disease," CNS Drugs, 30: 1079-1095 (2016).

Giacomoni, "Sun Protection in Man," Comprehensive Series in Photosciences, 3:642-648 (2001).

Institute of Medicine (US) Standing Committee on the Scientific Evaluation of Dietary Reference Intakes., "Dietary Reference Intakes for Calcium, Phosphorus, Magnesium, Vitamin D, and Fluoride," Washington, DC: The National Academies Press: 448 pages (1997).

International Search Report and Written Opinion for International Application No. PCT/US2015/056686 dated Feb. 9, 2016.

International Search Report and Written Opinion for International Application No. PCT/US2017/028646 dated Jun. 23, 2017.

International Search Report and Written Opinion for International Application No. PCT/US2019/061626 dated Feb. 13, 2020.

Kaakkola et al., "Effects of Catechol-O-Methyltransferase Inhibitors and L-3, 4-Dihydroxyphenylalaline With or Without Carbidope on Extracellular Dopamine in Rat Striatum," Journal of Neurochemistry, 60(1): 137-144 (1993).

Kearney et al., "The in vitro enzymic liabilities of chemically distinct phosphomonoester prodrugs," Pharmaceutical Research, 9(4):497-503 (1992).

Lee et al., "The Role of 3-O-Methyldopa in the Side Effects of L-dopa," Neurochem Res., 33: 401-411 (2008).

Maeda et al., "Phosphonylation of L-dopa with sodium phosphonate in aqueous solution," Phosphorus Research Bulletin, 25:56-60 (2011).

Murakami., "[New Series of anticancer drugs] Topoisomerase inhibitor: irinotecan hydrochloride," Tokai University School of Medicine: 9 pages (2000).

Nagatsu et al., "L-Dopa therapy for Parkinson's Disease: Past, Present, and Future," Parkinsonism & Related Disorders, 15(1): S3-S8 (2009).

NeuroDerm Press Release, "NeuroDerm Announces Presentation of Data from Studies Evaluating ND0612, an Investigational Levodopa Continuous Administration Drug, in Healthy Volunteers and in Patients with Advanced Parkinson's Disease," NeuroDerm Ltd dated Jun. 19, 2013.

Office Action and Search Report for Russian Application No. RU2017117413 mailed May 30, 2019.

Pawelek et al., "Increase in melanin formation and promotion of cytotoxicity in cultured melanoma cells caused by phosphorylated isomers of L-dopa," Cancer Research, 46(2):493- 497 (1996).

Poewe et al., "Novel Formulations and Modes of Delivery of Levodopa," Movement Disorders, 30(1): 114-120 (2015).

Rosebraugh et al., "A Novel Levodopa/Carbidopa Prodrug (ABBV-951) 24-Hour Continuous Subcutaneous Infusion Treatment for Parkinson's Disease (P3.8-037)," Neurology, 92,15 Supplement Abstract (2019).

Safadi et al., "Phosphoryloxymthyl carbamates and carbonates— Novel Water—soluble prodrugs for amines and hindered alcohols." Pharmaceutical Research, 10(9):1350-1355 (1993).

Tanner et al., "Epidemiology of Parkinson's Disease," Neurologic Clinics, 14: 317-335 (1996).

Taylor et al., "Fundamental of Nursing, " Lippincott Williams and Wilkins, p. 749, https://wikipedia.org/wiki/subcutaneous_injection.

Wadhwa et al., "Steady State Concentration," StatPearls Publishing retrieved online at <https://www.ncbi.nlm.nih.gov/books/NBK553-132/>: 4 pages (2021).

(56) References Cited

OTHER PUBLICATIONS

Written Opinion of the Intellectual Property Office of Singapore for Singapore Patent Application No. 11201703170R dated Feb. 26, 2018.
Y. Caraco et al.,. "Constant Therapeutic Levodopa Plasma Concentrations Maintained by Continuous Subcutaneous Administration of ND-0612, a Novel Formulation of Levodopa/Carbidopa" 17th International Congress of Parkinson's Disease and Movement Disorders, Jun. 2013, Sydney, Australia, Abstract No. 452: Abstract.
Y. Caraco et al.,. "Constant Therapeutic Levodopa Plasma Concentrations Maintained by Continuous Subcutaneous Administration of ND-0612, a Novel Formulation of Levodopa/Carbidopa" 17th International Congress of Parkinson's Disease and Movement Disorders, Jun. 2013, Sydney, Australia, Abstract No. 452: Poster.
Y. Caraco et al., "ND0612, A Novel Formulation of Levodopa/ Carbidopa for Continuous, Subcutaneous Administration, Achieves Steady-State Levodopa Plasma Concentrations in Parkinson's Disease Patients" 17th International Congress of Parkinson's Disease and Movement Disorders, Jun. 2013, Sydney, Australia, Abstract No. LBA26: Abstract.
Y. Caraco et al., "ND0612, A Novel Formulation of Levodopa/ Carbidopa for Continuous, Subcutaneous Administration, Achieves Steady-State Levodopa Plasma Concentrations in Parkinson's Disease Patients" 17th International Congress of Parkinson's Disease and Movement Disorders, Jun. 2013, Sydney, Australia, Abstract No. LBA26: Poster.
Zhu et al., "Phosphate prodrugs of PD154075," Bioorganic & Medicinal Chemistry Letters, 10:1121-1124 (2000).
Bodor et al., "Improved Delivery through Biological Membranes. 4. Prodrugs of L-Dopa," Journal of Medicinal Chemistry, 20(11): 1435-1445 (1977).
Carey., "Phase 3 of ND0612 clinical trial Initiated in the United States for Parkinson's disease with motor fluctuations," retrieved online <https://neuroderm.com/our-company/news-and-events/phase-3-initation/>: 6pages (2019).
Contin et al., "Pharmacokinetics of levodopa," J. Neurol., 257(Supplement 2): S253-S61 (2010).
Djaldetti et al., "Levodopa Ethylester: A novel Rescue therapy for Response Fluctuations in Parkinson's Disease," Annals of Neurology, 39(3): 400-404 (1996).
FDA Approved Labeling Text for NDA 017555: 9 pages (2011).
Guided Poster Tour Movement Disorder Society, Movement Disorders 27(Supp 1): S593-S601 (2012).
Guoxin et al., "Research Progress on the design and synthesis of phosphate ester prodrugs," Central South Pharmacy, 6(1): 82-85 w/ English translation (2008).
Haddad et al., "Dopamine and Levodopa Prodrugs for the Treatment of Parkinson's Disease," Molecules, 23(40): p. 1.-17 (2018).
Hauser., "Levodopa: Past, Present, and Future," European Neurology, 62: 1-8 (2009).
International Parkinson and Movement Disorder Society (MDS): 6 pages (2022).
Kleedorfer et al., "Subcutaneous and sublingual levodopa methyl ester in Parkinson's disease," Journal of Neurology, Neurosurgery & Psychiatry, 54(4): 373 (1991).
LeWitt et al., "Levodopa Thearpy for Parkinson's Disease: Pharmacokinetics and Pharmacodynamics," Movement Disorder, 30(1): 64-72 (2015).
LeWitt et al., "Levodopa therapy for Parkinson disease: A look backward and forward," Henry Ford Health System: 11 pages (2016).
LeWitt et al., "Pharmacokinetic-Pharmacodynamic Crossover Comparison of Two Levodopa Extension Strategies," Movement Disorders: 24(9): 1319-1324 (2009).
LeWitt., "Levodopa for the Treatment of Parkinson's Disease," The New England Journal of Medicine, 359(23): 2468-2476 (2008).
LeWitt., "Parkinson's Disease Guide for the Newly Diagnosed Understanding the Disease, Managing Your Symptoms & Navigating Treatment": 119 pages (2020).
LeWitt., "The Pharmacology of Levodopa in Treatment of Parkinson's Disease," Handbook of Experimental Pharmacology, vol. 88, Chapter 13: An Update: 61 pages (1989).
Lundqvist., "Continuous levodopa for advanced Parkinson's disease," Neuropsychiatric Disease and Treatment, 3(3): 335-348 (2007).
NeuroDerm., "Beyond Phase 2b Data Indicates ND0612 Has a Positive Long-Term Safety Profile for People with Parkinson's Disease," NeuroDerm Press Release: 4 pages (2022).
Nyholm et al., "Pharmacokinetics of Levodopa, Carbidopa, and 3-0-Methyldopa Following 16- hour Jejunal Infusion of Levodopa-Carbidopa Intestinal Gel in Advanced Parkinson's Disease Patients," The AAPS Journal, 15(2): 316-323 (2013).
Oren., "Continuous Subcutaneous Administration of Levodopa/ Carbidopa (ND0612) for the Treatment of Parkinson's Disease," NeuroDerm: 32 pages (2014).
Parkinson's News Today., "ND0612 for Parkinson's Disease," retrieved online <https://parkinsonsnewstoday.com/nd0612/>: 6 pages (2022).
Pfeiffer., "Transdermal drug delivery in Parkinson's disease," Aging Health, 3(4): 471-482 (2007).
Quinn et al., "Control of on/off phenomenon by continuous intravenous infusion of levodopa," Neurology, 34: 1131-1136 (1984).
Riley et al., "Parkinson's Disease: A Giving Smarter Guide," 52 pages (2022).
Stella., "Prodrugs: My Initial Exploration and Where It Led," Journal of Pharmaceutical Sciences, 109: 3514-3523 (2020).
Stella., "Prodrugs: Some Thoughts and Current Issues," Journal of Pharmaceutical Sciences, 99(12): 4755-4765 (2010).
Xun et al., "Application of phosphates and phosphonates prodrugs in drug research and development," Acta Pharmaceutica Sinica, 48(5): 621-634 (2013).
Zeevi et al., "Maintenance of Constant Steady State Therapeutic Plasma Concentrations of Levodopa Following Its Continuous Subcutaneous Administration with Carbidopa," NeuroDerm: 1 Page (2022).
2013 site map of Neuroderm.com from the Wayback Machine relating to the Neuroderm.com Home Page, 1 page.
2013 site map of Neuroderm.com from the Wayback Machine relating to the Neuroderm.com News Page, 1 page.
Abstracts of the Sixteenth International Congress of Parkinson's Disease and Movement Disorders, 27(S1) Movement Disorders S1-S523 (2012).
Aldred J et al: "Safety and Efficacy of 24-Hour/Day Subcutaneous Infusion of Foslevodopa/Foscarbidopa in Advanced Parkinson's Disease During a Phase 3 Study: 6-Month Interim Results", XP002808776, Database accession No. EMB-638416300 abstract & Neurology 20220501 Lippincott Williams, vol. 98, No. 18 Suppl, (2022).
Decision Granting Institution of Post-Grant Review, PTAB Case No. PGR2022-00040, dated Nov. 14, 2022, 52 pages.
Declaration of Geoffrey D. Biegler, dated Dec. 22, 2022, in *Neuroderm Ltd.* v. *AbbVie Inc.* (PTAB Case No. PGR2022-00040, filed Dec. 27, 2022).
Declaration of Jonathan E. Singer, dated Dec. 7, 2022, in *Neuroderm Ltd.* v. *AbbVie Inc.* (PTAB Case No. PGR2022-00040, filed Dec. 27, 2022).
Declaration of June Anne Munford, dated Jan. 13, 2022, in *Neuroderm Ltd.* v. *AbbVie Inc.* (PTAB Case No. PGR2022-00040, filed Jan. 17, 2023).
Declaration of Kenneth B. Sloan, Ph.D. in Support of Norwich's Opposition to Takeda's Motion for Summary Judgment, *Takeda Pharm. Co.* v. *Norwich Pharms., Inc.*, 2:20-cv-08966-SRC- CLW, (D.N.J. Oct. 28, 2022).
Declaration of Kenneth B. Sloan, Ph.D., dated May 10, 2022, in *Neuroderm Ltd.* v. *AbbVie Inc.* (PTAB Case No. PGR2022-00040, filed May 12, 2022).
Declaration of Matthew W. Johnson, dated Aug. 17, 2022, in *Neuroderm Ltd.* v. *AbbVie Inc.* (PTAB, Case No. PGR2022-00040, filed Aug. 17, 2022).
Declaration of Nathaniel E. Frank-White, dated Dec. 12, 2022, in *Neuroderm Ltd.* v. *AbbVie Inc.* (PTAB Case No. PGR2022-00040, filed Jan. 17, 2023).

(56) References Cited

OTHER PUBLICATIONS

Declaration of Nathaniel E. Frank-White, dated Feb. 2, 2022, in *Neuroderm Ltd.* v. *AbbVie Inc.* (PTAB Case No. PGR2022-00040, filed May 12, 2022).
Declaration of Peter A. LeWitt, M.D, dated May 10, 2022, in *Neuroderm Ltd.* v. *AbbVie Inc.* (PTAB Case No. PGR2022-00040, filed May 12, 2022).
Extended European Search Report for EP Application No. 22204022.2 dated May 3, 2023.
Hauser et al., Efficacy of Instradefylline, an Adenosine A2A Receptor Antagonist, as Adjunctive Therapy to Levodopa in Parkinson's Disease: A Pooled Analysis of 8 Phase 2b/3 Trials, 11 Journal of Parkinson's Disease 1663-75 (2021).
Hideko et al., "Phosphonylation of L-Dopa With Sodiijm Diphosphonate in Aqueous Solution" Phospitorus Research Bulletin, vol. 25, pp. 55-60. (2011).
How seeds, documents, and collections work together, Archive-It, https://support.archive-it.org/hc/en-us/articles/360000706843-Howseeds-documents-and-collections-work-together (last accessed Jun. 30, 2022).
International Search Report and Written Opinion for Application No. PCT/US2022/048056 dated May 24, 2023.
Isaacson et al., "Effect of using a wearable device on clinical decision-making and motor symptoms in patients with Parkinson's disease starting transdermal rotigotine patch: A pilot study", Parkinsonism Relat Disord, 64: 132-137 (2019).
Isaacson et al., Safety and Efficacy of Continuous Apomorphine Infusion in Patients with Parkinson's disease: Results from a Phase 3, Open-label Study (1771), 94 (15 Supplement) Neurology 1-6 (2020).
J. Chesler Opinion, *Takeda Pharm. Co.* v. *Norwich Pharms., Inc.*, 2:20-cv-08966-SRC-CLW, (D.N.J. Dec. 27, 2022) (Chesler Opinion).
J. Dickson Letter Order, *Teva Neuroscience Inc.* v. *Watson Pharma, Inc.*, 2:10-cv-05078-CCC-JAD, (D.N.J. Jun. 29, 2012).
June Ann Munford Cross-Examination Transcript dated Jan. 19, 2023 in *Neuroderm Ltd.* v. *AbbVie Inc.* (PTAB Case No. PGR2022-00040).
Kenneth B. Sloan, Ph.D. Cross-Examination Transcript dated Jan. 25, 2023 in *Neuroderm Ltd.* v. *AbbVie Inc.* (PTAB Case No. PGR2022-00040).
Letter from the Movement Disorder Society to Peter LeWitt of Mar. 2012.
LeWitt et al., "Levodopa therapy for Parkinson's disease: A look backward and forward," Neurology, 86(14 Suppl 1):S3-S12 (2016).
LeWitt et al., Double-Blind Study of the Actively Transported Levodopa Prodrug XP21279 in Parkinson's Disease, 29(1) Movement Disorders 75-82 (2014).
LeWitt et al., Parkinson Disease and Orthostatic Hypotension in the Elderly: Recognition and Management of Risk Factors for Falls, 11(3) Aging and Disease 679-91 (2020).
LeWitt et al., Pulmonary Safety and Tolerability of Inhaled Levodopa (CVT-301) Administered to Patients with Parkinson's Disease, 31(3) Journal of Aerosol Medicine and Pulmonary Drug Delivery 155-61 (2018).
LeWitt, "Levodopa Therapy for Parkinson's Disease: Pharmacokinetics and Pharmacodynamics," Movement Disorders, 30(1):64-72 (2015).
LeWitt, Recent advances in CSF biomarkers for Parkinson's disease, 18S1 Parkinsonism and Related Disorders S49-51 (2012).
Loeffler et al., Nocardia asteroides-Induced Movement Abnormalities in Mice: Relevance for Parkinson's Disease?, 31(8) Movement Disorders 1134-38 (2016).
Martinez☐Martin et al., "The Parkinson's Disease Sleep Scale-2 (PDSS [2]: Validation of the Spanish Version and Its Relationship With a Roommate☐Based Version." *Movement disorders clinical practice* 6(4): 294-301 (2019).
Mitsubishi Tanabe Is Making a Huge Mistake: Why We Believe NeuroDerm Is a Lemon, Seeking Alpha, https://seekingalpha.com/article/4104212-mitsubishi-tanabe-ismaking-huge-mistake-why-believe-neuroderm-is-lemon#comments (last visited Jan. 27, 2023).
ND0612 for Parkinson's Disease, https://parkinsonsnewstoday.com/nd0612/ (last visited May 10, 2022).
NeuroDerm Ltd. U.S. Sec Amendment No. 1 to Form F-1 as filed on Nov. 3, 2014.
Ondo et al., Comparison of the Fahn-Tolosa-Marin Clinical Rating Scale and the Essential Tremor Rating Assessment Scale, 5(1) Movement Disorders Clinical Practice 60-65 (2017).
Oren, "Continuous Subcutaneous Administration of Levodopa/Carbidopa (ND0612) for the Treatment of Parkinson's Disease," presentation presented at the Parkinson's Disease Therapeutics Conference, Oct. 29, 2014, New York, New York.
Parkinson.org "Motor Fluctuations and Parkinson's 'Off' Times", Parkinson's Foundation (2021).
Patent Owner' Sur-Reply, PTAB Case. No. PGR-2022-0040, filed Sep. 14, 2022, 11 pages.
Patent Owner's Non-Contingent Motion to Amend, PTAB Case. No. PGR2022-00040, filed Feb. 6, 2023, 36 pages.
Peter A. LeWitt, M.D. Cross-Examination Transcript dated Jan. 30, 2023, Public (Redacted) Version, in *Neuroderm Ltd.* v. *AbbVie Inc.* (PTAB Case No. PGR2022-00040).
Petition for Post Grant Review of U.S. Pat. No. 11,091,507, PTAB Case No. PGR2022-00040, filed May 12, 2022, 119 pages.
Petitioner's Reply to Patent Owner's Preliminary Response, PTAB Case No. PGR2022-00040, filed Sep. 2, 2022, 10 pages.
PGR2022-00040, Order: Granting Petitioner's Motion to Submit Supplemental Information, dated Jan. 13, 2023, 7 pages.
Poewe et al., Subcutaneous Levodopa Infusion for Parkinson's Disease: 1-Year Data from the Open-Label BeyoND Study, 36(11) Movement Disorders 2687-92 (2021).
Press Release, NeuroDerm, Phase 3 of ND0612 clinical trial Initiated in the United States for Parkinson's disease with motor fluctuations, (Aug. 28, 2019), available at https://neuroderm.com/our-company/news-and-events/phase3-initiation/ (last visited on May 10, 2022).
Printout of the Home Page of Neuroderm.com from the Wayback Machine as of Aug. 2, 2013, 1 page.
Printout of the News Page of Neuroderm.com from the Wayback Machine as of Aug. 2, 2013, 1 page.
Ramot et al., Ninety-day Local Tolerability and Toxicity Study of ND0612, a Novel Formulation of Levodopa/Carbidopa, Administered by Subcutaneous Continuous Infusion in Minipigs, 45(6) Toxicologic Pathology 764-773 (2017).
SciFinder Substances, Carbidopa. Retrieved from the internet on Feb. 21, 2023, https://scifinder-n.cas.org/searchDetail/substance/63f503012e7dee60e3d561ef/substanceDetails (Year: 2023).
SciFinder Substances, Levodopa. Retrieved from the internet on Feb. 21, 2023, https://scifinder-n.cas.org/searchDetail/substance/63f502ba2e7dee60e3d55e56/substanceDetails (Year: 2023).
Silbergleit et al., Quantitative Analysis of Voice in Parkinson Disease Compared to Motor Performance: A Pilot Study, 5 Journal of Parkinson's Disease 517-24 (2015).
Skorvanek et al., "Differences in MDS☐UPDRS scores based on Hoehn and Yahr stage and disease duration", *Movement disorders clinical practice* 4(4): 536-544 (2017).
Soileau M et al: "Impact of foslevodopa/foscarbidopa on key clinical and patient reported outcomes in patients with a PD: Responder analysis of two Phase 3 clinical trials", Movement Disorders 37: Abstracts of the 2022 MOS International Congress, Sep. 1, 2022 (Sep. 1, 2022), pp. S354-S355.
Stodtmann s et al., "Daily time-course of efficacy of continuous subcutaneous infusion of foslevodopa/ foscarbidopain advanced Parkinson's disease patients from a phase lb study", Movement Disorders, 35, Suppl 1 , p. 421 (2020).
The Movement Disorder Society, 16th International Congress of Parkinson's Disease and Movement Disorders, Final Conference Program.
What is a web crawler? | How web spiders work, Cloudflare, https://www.cloudflare.com/learning/bots/what-is-a-web-crawler/ (last accessed Jun. 30, 2022).

(56) References Cited

OTHER PUBLICATIONS www.neuroderm.com Access History, Wayback Machine, https://web.archive.org/web/20130115000000*/www.neuroderm.com (last accessed Jun. 30, 2022).
www.neuroderm.com/park.html Nov. 19, 2013 capture, Wayback Machine, https://web.archive.org/web/20131119225317/http://www.neuroderm.com/park.html (last accessed Jan. 18, 2023) (Neuroderm.com Pipeline-ND0612).
www.neuroderm.com/PDF/posterND0612MDS2012.pdf Access History, Wayback Machine, https://web.archive.org/web/2019*/www.neuroderm.com/PDF/posterND0612MDS2012.pdf (last accessed Jun. 30, 2022).
www.neuroderm.com/pipeline.html Nov. 26, 2013 capture, Wayback Machine, https://web.archive.org/web/20131126221018/http://neuroderm.com/pipeline.html (last accessed Jan. 18, 2023).
Extended European Search Report for EP Application No. 23192663.5 dated Jun. 17, 2024.
Partial European Search Report for EP Application No. 23192663.5 dated Mar. 27, 2024.
Rosebraugh et al., "Foslevodopa/Foscarbidopa Is Well Tolerated and Maintains Stable Levodopa and Carbidopa Exposure Following Subcutaneous Infusion," Journal of Parkinson's Disease 11 (2021): 1695-1702.
Vyalev, FDA Label, 31 pages, Revised Oct. 2024.

\* cited by examiner

PHARMACEUTICAL FORMULATIONS FOR SUBCUTANEOUS ADMINISTRATION

CROSS-REFERENCE TO RELATED APPLICATIONS

This application claims the benefit of U.S. Provisional Application No. 62/898,214 filed on Sep. 10, 2019; U.S. Provisional Application No. 62/863,113 filed on Jun. 18, 2019; U.S. Provisional Application No. 62/683,101 filed on Jun. 18, 2019; U.S. Provisional Application No. 62/863,093 filed on Jun. 18, 2019; U.S. Provisional Application No. 62/843,945 filed on May 6, 2019; and U.S. Provisional Application No. 62/767,546 filed on Nov. 15, 2018, each of which is incorporated herein by reference in its entirety.

FIELD OF THE INVENTION

The present disclosure relates to stable pharmaceutical formulations of levodopa prodrugs and carbidopa prodrugs for subcutaneous administration.

BACKGROUND

Parkinson's disease is a chronic and progressive neurodegenerative condition characterized by reduced levels in the brain of the neurotransmitter dopamine (i.e., 3,4-dihydroxyphenethylamine). Administration of levodopa (i.e., L-3,4-dihydroxyphenylalanine) currently is the most effective therapy for treating Parkinson's disease patients. Co-administration of carbidopa with levodopa inhibits the peripheral metabolism of levodopa to dopamine, which significantly reduces the levodopa dose required for a therapeutically effective clinical response and reduces the associated side effects.

Oral administration of tablets containing levodopa and carbidopa, particularly products having a 4:1 weight by weight (w/w) ratio of levodopa to carbidopa, have long been used for the treatment of the Parkinson's disease. For example, Sinemet® is the registered trademark for a preparation of levodopa and carbidopa from Merck Sharp and Dohme Corp., USA having a 4:1 weight by weight (w/w) ratio of levodopa to carbidopa. However, it is difficult to consistently maintain the desired dopamine levels in the brain with these oral tablets as levodopa has a short half-life, even when co-administered with carbidopa.

Oral ingestion of levodopa tablets is associated with variable exposure to plasma levodopa. One approach that has been effective in reducing variability of dopamine levels compared with oral administration of levodopa and carbidopa tablets is the continuous intestinal delivery of a levodopa/carbidopa gel. One product, known by its commercial name Duodopa® in Europe and Duopa® in the United States, from AbbVie Inc., USA, is a suspension of levodopa/carbidopa monohydrate (4:1 w/w ratio of levodopa to carbidopa monohydrate) in an aqueous gel (carboxymethyl cellulose sodium). The gel is delivered to the proximal small intestine through a jejunal tube inserted through a surgically implanted percutaneous endoscopic gastrostomy port. Continuous delivery of levodopa to provide therapeutic dopamine levels in the brain without the use of a surgical implant could be beneficial.

Levodopa and carbidopa each have low aqueous solubility at neutral pH. Stable, more soluble formulations comprising levodopa (or compounds capable of in vivo bioconversion to levodopa) are difficult to achieve due to the relatively insoluble nature of levodopa and carbidopa. Prior prodrug approaches for delivering levodopa subcutaneously have failed due to various technical challenges, for example, insufficient chemical stability, insufficient solubility, in vivo bioconversion issues, and toxicity, to name a few reasons. No subcutaneously administered levodopa product is commercially available and subcutaneous administration of levodopa, whether with or without carbidopa, has yet to be successfully commercialized.

Certain prodrugs of levodopa and carbidopa suitable for subcutaneous administration have been described in WO 2016/065019 A1, the administration, methods of manufacture and use of which are incorporated by reference. However, it would be beneficial to provide a safe and stable composition for administering such prodrugs.

One approach for formulating prodrugs of levodopa is described in WO 2018/154447 A1. This approach requires the use of one, two, or more antioxidants, which adds complexity in maintaining product quality. The compositions described contain 1.36% phosphate esters of carbidopa (CD-p) and 5.64% phosphate esters of levodopa (LD-p).

Another approach for delivering levodopa subcutaneously is described in WO 2015/136538 A1. This approach describes dopa decarboxylase inhibitor compositions requiring a carbidopa arginine complex in combination with levodopa. However, no evidence of subcutaneously delivering the compositions described therein is reported.

To date, there remains a need for commercially viable pharmaceutical compositions suitable for subcutaneous delivery of levodopa and carbidopa prodrugs for the treatment of Parkinson's disease.

SUMMARY OF THE INVENTION

The present disclosure relates to safe and stable aqueous pharmaceutical compositions suitable for subcutaneous administration comprising a ratio of about 20:1 levodopa phosphate prodrug to carbidopa phosphate prodrug. The compositions provide a stable liquid suitable for subcutaneous administration. In certain embodiments, when administered to human subjects, such compositions achieve similar pharmacokinetic plasma exposure of levodopa as oral levodopa/carbidopa therapy comparable to the Sinemet® product. Such pharmacokinetic plasma exposure is sustained over time. Furthermore, such compositions are safe and well tolerated in human subjects. Viewed from this aspect, the disclosure provides pharmaceutical compositions suitable for subcutaneous administration comprising a levodopa phosphate prodrug and a carbidopa phosphate prodrug as described herein and at least one pharmaceutically acceptable carrier, wherein the weight by weight ratio of the levodopa phosphate prodrug to the carbidopa phosphate prodrug is about 20:1 and can be administered in human subjects. In some embodiments, the composition is an aqueous liquid composition having a pH of between about 6.5 to about 9.0.

Accordingly, the present disclosure relates to a stable liquid aqueous pharmaceutical composition comprising a compound of formula:

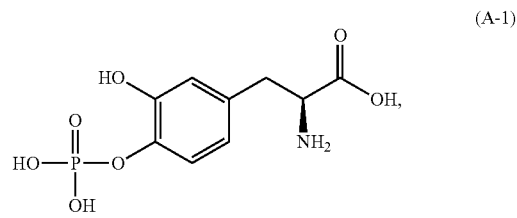 [SMILES: N[C@@H](Cc1ccc(OP(=O)(O)O)c(O)c1)C(=O)O]

(A-1)

and a compound of formula:

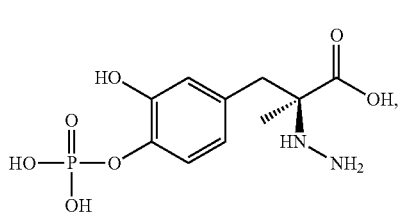
(B-1)

wherein the weight to weight ratio of compound (A-1) to compound (B-1) is about 20:1, and wherein the pharmaceutical composition is suitable for subcutaneous administration.

In another aspect, the present disclosure relates to a stable liquid aqueous pharmaceutical composition comprising:
a compound of formula:

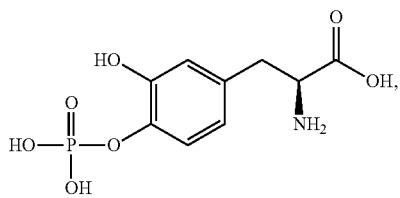
(A-1)

and
a compound of formula:

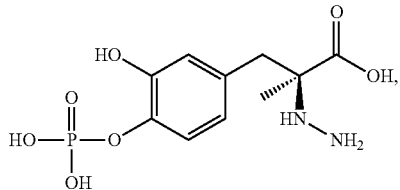
(B-1)

wherein the concentration of compound (A-1) is about 240 mg/mL and the concentration of compound (B-1) is about 12 mg/mL; wherein the pharmaceutical composition is suitable for subcutaneous administration, and
wherein the pharmaceutical composition provides a mean plasma exposure ratio of levodopa to carbidopa as measured by $AUC_{(0-t)}$ to $AUC_{(0-t)}$ is about 7.30 to 1 when administered to adult humans.

In another aspect, the present disclosure related to a stable liquid pharmaceutical composition comprising:
a compound of formula:

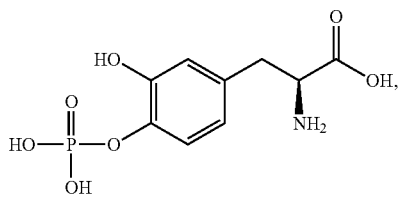
(A-1)

a compound of formula:

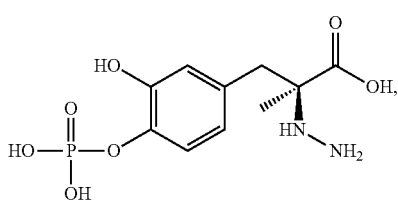
(B-1)

and water;
wherein the concentration of compound (A-1) is about 240 mg/mL and the concentration of compound (B-1) is about 12 mg/mL;
wherein the pharmaceutical composition is suitable for subcutaneous administration, and
wherein the composition is substantially antioxidant free.

In another aspect, the present disclosure relates to a stable liquid aqueous pharmaceutical composition comprising:
a compound of formula:

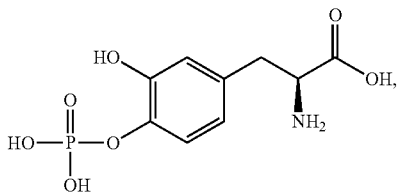
(A-1)

and
a compound of formula:

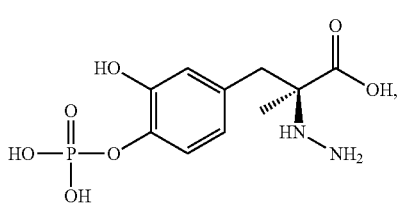
(B-1)

wherein the concentration of compound (A-1) is about 240 mg/mL and the concentration of compound (B-1) is about 12 mg/mL;
wherein the pharmaceutical composition is suitable for subcutaneous administration, and
wherein the composition comprises less than about 5.4% w/w DHPPA-P at a pH between 6.5 and 9.0 after 5 days at 25° C. followed by 30 days at 5° C.

As disclosed herein, the present disclosure relates to the following embodiments.

Embodiment 1

A stable liquid aqueous pharmaceutical composition comprising
a compound of formula:

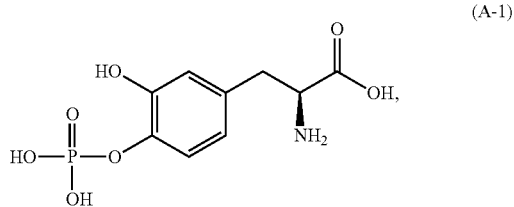 [SMILES: N[C@@H](Cc1ccc(OP(=O)(O)O)c(O)c1)C(=O)O]

(A-1)

and
a compound of formula:

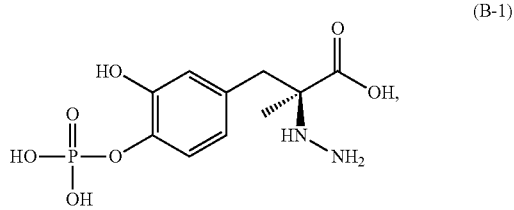 [SMILES: C[C@@](Cc1ccc(OP(=O)(O)O)c(O)c1)(NN)C(=O)O]

(B-1)

wherein the weight to weight ratio of compound (A-1) to compound (B-1) is about 20:1, and wherein the pharmaceutical composition is suitable for subcutaneous administration.

Embodiment 2

The stable liquid aqueous pharmaceutical composition of embodiment 1, wherein the concentration of compound (A-1) is between about 216 mg/mL and about 264 mg/mL.

Embodiment 3

The stable liquid aqueous pharmaceutical composition of embodiment 1 or 2, wherein the concentration of compound (B-1) is between 9.6 mg/mL and 13.2 mg/mL.

Embodiment 4

The stable liquid aqueous pharmaceutical composition of embodiment 1, wherein the concentration of compound (A-1) is about 240 mg/mL, and the concentration of compound (B-1) is about 12 mg/mL.

Embodiment 5

The stable liquid aqueous pharmaceutical composition of any one of embodiments 1 to 4, wherein the composition has a pH of between about 6.5 and about 9.0.

Embodiment 6

The stable liquid aqueous pharmaceutical composition of embodiment 1, wherein the concentration of compound (A-1) is between 324 mg/mL and 396 mg/mL, and the concentration of compound (B-1) is between 16.2 mg/mL and 19.8 mg/mL.

Embodiment 7

The stable liquid aqueous pharmaceutical composition of embodiment 6, wherein the concentration of compound (A-1) is about 360 mg/mL, and the concentration of compound (B-1) is about 18 mg/mL.

Embodiment 8

The stable liquid aqueous pharmaceutical composition of embodiment 6 or 7, wherein the composition has a pH of between about 6.5 and about 9.0.

Embodiment 9

The stable liquid aqueous pharmaceutical composition of any one of embodiments 1 to 5, wherein the pharmaceutical composition provides a mean plasma exposure ratio of levodopa to carbidopa as measured by $AUC_{(0-t)}$ to $AUC_{(0-t)}$ between 6.57 and 8.03 levodopa to about 1 carbidopa when administered to adult humans.

Embodiment 10

The stable liquid aqueous pharmaceutical composition of embodiment 9, wherein the pharmaceutical composition provides a mean plasma exposure ratio of levodopa to carbidopa as measured by $AUC_{(0-t)}$ to $AUC_{(0-t)}$ of about 7.30 levodopa to about 1 carbidopa when administered to adult humans.

Embodiment 11

The stable liquid aqueous pharmaceutical composition of any one of embodiments 1 to 5, wherein the continuous subcutaneous administration of the pharmaceutical composition to a population of adult humans achieves a mean plasma concentration of levodopa having a degree of fluctuation of about 0.3 or less over 2-16 hours following administration, wherein the degree of fluctuation is defined as the $([C_{max} - C_{min}]/C_{ave})$ for the given time period.

Embodiment 12

The stable liquid aqueous pharmaceutical composition of any one of the embodiments 1 to 5, wherein the continuous subcutaneous administration of the composition to a population of adult humans achieves a mean plasma concentration of levodopa having a degree of fluctuation of about 0.40 over 2-72 hours following administration, wherein the degree of fluctuation is defined as the $([C_{max} - C_{min}]/C_{ave})$ for the given time period.

Embodiment 13

The stable liquid aqueous pharmaceutical composition of any one of embodiments 1 to 5, wherein the pharmaceutical composition is in a vial having a gaseous headspace comprising about 5.5% or less oxygen.

Embodiment 14

The stable liquid aqueous pharmaceutical composition of embodiment 13, wherein the pharmaceutical composition has a pH of between about 6.8 to about 7.8.

Embodiment 15

The stable liquid aqueous pharmaceutical composition of any one of the preceding embodiments, wherein the pharmaceutical composition is substantially antioxidant free.

Embodiment 16

The stable liquid aqueous pharmaceutical composition of any one of the preceding embodiments, wherein the pharmaceutical composition is substantially arginine free.

Embodiment 17

The stable liquid aqueous pharmaceutical composition of any one of the preceding embodiments, wherein the composition comprises less than about 5.4% w/w DHPPA-P relative to carbidopa 4' monophosphate at a pH between 6.5 and 9.0 after 5 days at 25° C. followed by 30 days at 5° C.

Embodiment 18

The stable liquid aqueous pharmaceutical composition of any one of the preceding embodiments, wherein the pharmaceutical composition is substantially free of ascorbic acid or a pharmaceutically acceptable salt of ascorbic acid.

Embodiment 19

The stable liquid aqueous pharmaceutical composition of any one of the preceding embodiments, wherein the pharmaceutical composition is substantially free of L-cysteine or a pharmaceutically acceptable salt thereof; N-acetylcysteine (NAC) or a pharmaceutically acceptable salt thereof; glutathione or a pharmaceutically acceptable salt thereof; diacetyl cysteine or a pharmaceutically acceptable salt thereof; and sodium bisulfite, or any combination thereof.

Embodiment 20

The stable liquid aqueous pharmaceutical composition of any one of the preceding embodiments, wherein the composition is substantially antioxidant free and wherein the composition comprises less than about 15 micrograms/mL hydrazine following storage at 5 days at 25° C. followed by 30 days at 5° C. conditions at pH neutral conditions.

Embodiment 21

A stable liquid aqueous pharmaceutical composition comprising
a compound of formula:

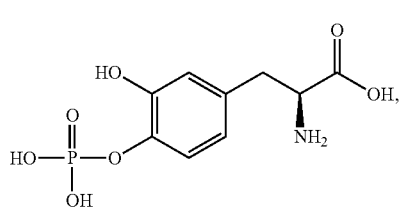

(A-1)

a compound of formula:

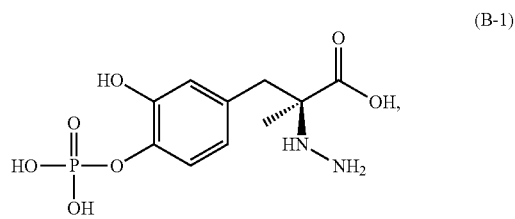 [SMILES: C[C@@](Cc1ccc(OP(=O)(O)O)c(O)c1)(NN)C(=O)O]

(B-1)

and water;
wherein the concentration of compound (A-1) is about 240 mg/mL and the concentration of compound (B-1) is about 12 mg/mL; wherein the pharmaceutical composition is suitable for subcutaneous administration, and,
wherein the pharmaceutical composition provides a mean plasma exposure ratio of levodopa to carbidopa as measured by $AUC_{(0-t)}$ to $AUC_{(0-t)}$ is about 7.30 to 1 when administered to adult humans.

Embodiment 22

The stable liquid aqueous pharmaceutical composition of embodiment 21, wherein the pharmaceutical composition is stable for at least three months in a 10-cc vial having less than about 9% oxygen at 1 atmospheric pressure at temperatures between 2° C. to 8° C.

Embodiment 23

The stable liquid aqueous pharmaceutical composition of embodiment 22, wherein the composition has a pH of between about 6.5 and about 9.0.

Embodiment 24

The stable liquid aqueous pharmaceutical composition of embodiment 23, wherein the composition has a pH of between about 6.8 and about 7.8.

Embodiment 25

The stable liquid aqueous pharmaceutical composition of any one of embodiments 22 to 24, wherein the vial has less than about 5.5% oxygen in the vial headspace.

Embodiment 26

A stable liquid aqueous pharmaceutical composition comprising
a compound of formula:

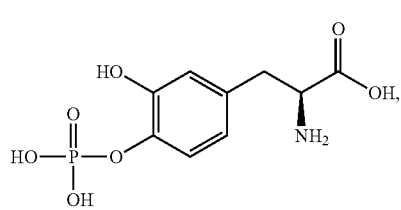

(A-1)

a compound of formula:

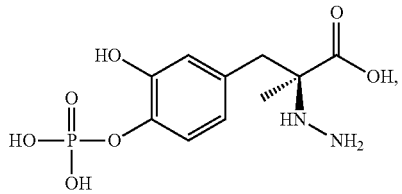

and water;
wherein the concentration of compound (A-1) is about 240 mg/mL and the concentration of compound (B-1) is about 12 mg/mL;
wherein the pharmaceutical composition is suitable for subcutaneous administration, and,
wherein the pharmaceutical composition is substantially antioxidant free.

Embodiment 27

The stable pharmaceutical composition of embodiment 26, wherein the pharmaceutical composition provides a mean plasma exposure ratio of levodopa to carbidopa as measured by $AUC_{(0-t)}$ to $AUC_{(0-t)}$ is about 7.30 to 1 when administered to adult humans.

Embodiment 28

The stable liquid aqueous pharmaceutical composition of embodiment 27, wherein the pharmaceutical composition is stable for at least three months in a 10-cc vial having less than about 9% oxygen at 1 atmospheric pressure at temperatures between 2° C. to 8° C.

Embodiment 29

The stable liquid aqueous pharmaceutical composition of any one of embodiments 26 to 28, wherein the composition has a pH of between about 6.5 and about 9.0.

Embodiment 30

The stable liquid aqueous pharmaceutical composition of embodiment 29, wherein the composition has a pH of between about 6.8 and about 7.8.

Embodiment 31

The stable liquid aqueous pharmaceutical composition of any one of embodiments 28 to 30, wherein the vial has less than about 5.5% oxygen.

Embodiment 32

A stable liquid aqueous pharmaceutical composition comprising
a compound of formula:

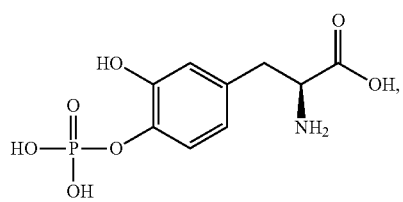

and
a compound of formula:

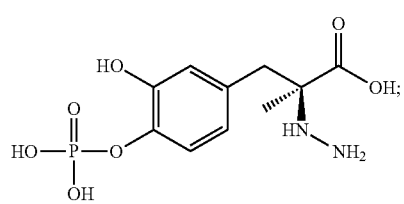

wherein the concentration of compound (A-1) is about 240 mg/mL and the concentration of compound (B-1) is about 12 mg/mL;
wherein the pharmaceutical composition is suitable for subcutaneous administration, and,
wherein the pharmaceutical composition comprises less than about 5.4% w/w DHPPA-P at a pH between 6.5 and 9.0 after storage for 5 days at 25° C. followed by 30 days at 5° C.

Embodiment 33

The stable liquid aqueous pharmaceutical composition of embodiment 32, wherein the pharmaceutical composition is stable for at least three months in a 10-cc vial having less than about 9% oxygen volume to volume at 1 atmospheric pressure at temperatures between 2° C. to 8° C.

Embodiment 34

The stable liquid aqueous pharmaceutical composition of embodiment 32 or 33, wherein the composition has a pH of between about 6.5 and about 9.0.

Embodiment 35

The stable liquid aqueous pharmaceutical composition of embodiment 34, wherein the composition has a pH of between about 6.8 and about 7.8.

Embodiment 36

The stable liquid aqueous pharmaceutical composition of any one of embodiments 33 to 35, wherein the vial has less than about 5.5% oxygen.

Embodiment 37

The stable pharmaceutical composition of any one of embodiments 32 to 36, wherein the pharmaceutical composition provides a mean plasma exposure ratio of levodopa to carbidopa as measured by $AUC_{(0-t)}$ to $AUC_{(0-t)}$ is about 7.30 to 1 when administered to adult humans.

Embodiment 38

A method of treating Parkinson's disease in a subject, comprising subcutaneously administering a pharmaceutical composition of anyone of embodiments 1 to 37 to a patient in need thereof.

Embodiment 39

A method of treating Parkinson's disease in a subject, comprising subcutaneously administering a pharmaceutical composition of embodiment 32 to a patient in need of Parkinson's disease treatment to provide a mean plasma exposure ratio of levodopa to carbidopa as measured by $AUC_{(0-t)}$ to $AUC_{(0-t)}$ of about 7.30 to 1 when administered to adult humans.

Embodiment 40

A method of improving "off" time of parkinsonian symptoms in a subject from a baseline score, comprising subcutaneously administering a pharmaceutical composition of any one of the embodiments 1-37, to a patient in need of treatment for Parkinson's Disease in an amount effective for reducing parkinsonian symptoms by at least 46% from baseline.

Embodiment 41

A method of improving a Movement Disorder Society-Unified Parkinson's Disease Rating Scale (MDS-UPDRS) total score in a subject having a baseline MDS-UPDRS score, comprising subcutaneously administering a pharmaceutical composition of claim 21 to a subject in need of treatment for Parkinson's disease in an amount effective for reducing the baseline MDS-UPDRS total score by at least 9 units.

Embodiment 42

A method of improving quality of life in a subject having a baseline Parkinson's disease Questionnaire-39 items (PDQ-39) summary index score, comprising subcutaneously administering a pharmaceutical composition of claim 21 to a subject in need of treatment for Parkinson's disease in an amount effective for reducing the baseline PDQ-39 score by at least 6.9 units.

Embodiment 43

A method of improving sleep in a subject having a baseline Parkinson's disease Sleep Scale-2 (PDSS-2) total score, comprising subcutaneously administering a pharmaceutical composition of claim 21 to a subject in need of treatment for Parkinson's disease in an amount effective for reducing the baseline PDSS-2 total score by at least 2 units.

Embodiment 44

A method of any one of embodiments 38-43, wherein the subject is treated for at least 10 days with no incidence of developing skin nodules.

Embodiment 44

A method of reducing incidences of "off" time of parkinsonian symptoms in a subject compared with the subject receiving oral administration of tablets containing levodopa and carbidopa, comprising subcutaneously administering a pharmaceutical composition of any of the embodiments 1 to 21 to a patient in need of treatment for Parkinson's disease.

Embodiment 45

A method of embodiment 44, wherein the incidences of "off" time of parkinsonian symptoms in a subject are reduced while increasing "on" time without troublesome dyskinesia.

Further benefits of the present disclosure will be apparent to one skilled in the art from reading this patent application. The embodiments of the disclosure described in the following paragraphs are intended to illustrate the invention and should not be deemed to narrow the scope of the invention.

DETAILED DESCRIPTION OF THE INVENTION

Figure 1:
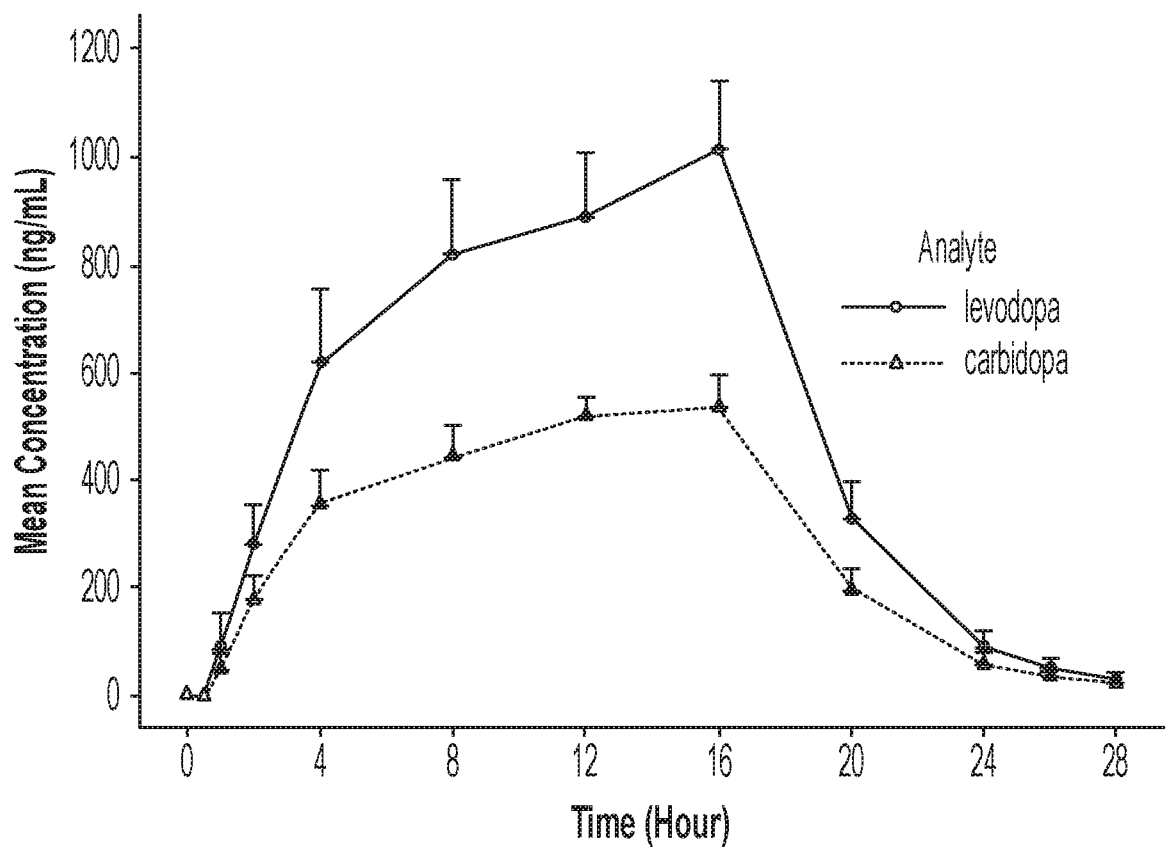
FIG. 1 is a plasma time-concentration profile of levodopa and carbidopa levels in healthy human volunteers after subcutaneous administration of a pharmaceutical composition of levodopa 4'-monophosphate and carbidopa 4'-monophosphate at a ratio of 4:1.

The present disclosure describes the unexpected discovery that subcutaneous administration to a human of a pharmaceutical composition having a dosing ratio of about 20:1 w/w of levodopa phosphate prodrug to carbidopa phosphate prodrug provides an effective level of levodopa to carbidopa exposure. Such compositions incorporate a surprisingly lower than expected, but still therapeutically relevant, amount of carbidopa. The reduction in carbidopa drug load in the composition is beneficial for the patient, in that it reduces any by-products associated with carbidopa degradation and therefore results in increased stability and an improved safety profile of the composition. Accordingly, the present disclosure provides stable aqueous pharmaceutical formulations of levodopa and carbidopa phosphate prodrugs for subcutaneous administration.

As previously noted, the inherently low aqueous solubility of levodopa at physiologically acceptable pH for subcutaneous infusion presents a significant technical challenge to the development of improved pharmaceutical compositions and methods of treatment. Such challenges include, for example, difficulties in achieving appropriate dosing volume and formulation stability within the required pH limitations. These challenges are further complicated by the requirement that the pharmaceutical compositions and methods of treatment provide pharmacokinetically-appropriate and pharmacokinetically-consistent control of dopamine levels in the human patient's brain.

The pharmaceutical compositions of the present disclosure have overcome the challenges of previous approaches for administering levodopa with or without carbidopa. Such pharmaceutical compositions can be administered to patients suffering from Parkinson's disease and associated conditions.

In various embodiments of the present disclosure, the pharmaceutical compositions comprise levodopa and carbidopa prodrugs that convert to levodopa and carbidopa in vivo. The pharmaceutical compositions of the present disclosure allows for delivery by continuous subcutaneous administration. Such subcutaneous administration can maintain continuous levodopa steady state plasma concentrations similar to the commercially available intestinal gel formulation that is a 4:1 ratio of levodopa to carbidopa, currently marketed under the tradename Duodopa®/Duopa®. Moreover, this continuous administration provides an advantage of essentially eliminating the significant fluctuation in levodopa steady-state plasma drug concentration ($C_{ss}$) with administration of oral tablets that are a 4:1 ratio of levodopa to carbidopa, sold as Sinemet®. The present pharmaceutical formulations also have reduced relative concentrations of carbidopa compared to intraduodenally administered gel and oral therapy. The pharmaceutical compositions and methods of the present disclosure represent an advancement in the treatment of Parkinson's disease and other related conditions.

The pharmaceutical compositions of the present disclosure achieve continuous levodopa steady state concentration ($C_{ss}$) similar to currently marketed intraduodenal gel therapy and without the significant fluctuation in levodopa $C_{ss}$ seen with oral therapy. In addition, such continuous levodopa steady state plasma concentrations are achieved with the pharmaceutical compositions of the present disclosure without the need for surgical implantation of percutaneous endoscopic gastrostomy port as required for intraduodenal administration. Furthermore, the pharmaceutical compositions of the present disclosure achieve low levels of hydrazine and DHPPA-P degradants at about neutral pH levels while being substantially free of antioxidants. For example, the pharmaceutical composition releases less than about 15 micrograms/mL of hydrazine after storage for about 5 days at 25° C. and about 30 days at 5° C. Such pharmaceutical compositions are advantageous over compositions which use antioxidants and have pH levels above 9.1 as described in WO 2018/15447.

The levodopa phosphate prodrug is:

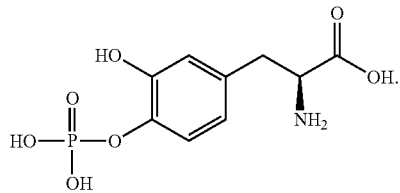

(A-1)

The compound (A-1) has a chemical name levodopa-4'-monophophate, which has been assigned the CAS registry number 97321-87-4. The International Nonproprietary Name for levodopa-4'-monophosphate is foslevodopa.

The carbidopa phosphate prodrug is

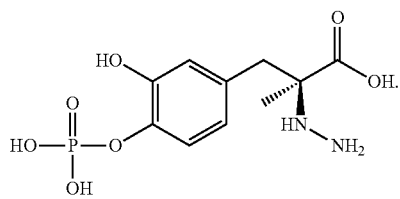

(B-1)

The compound (B-1) has a chemical name carbidopa-4'-monophophate, which has been assigned the CAS registry number 28860-95-9. The International Nonproprietary Name for carbidopa-4'-monophosphate is foscarbidopa.

As used herein, certain terms may be used in this disclosure.

Where a numeric range is recited herein, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated.

The singular forms "a," "an" and "the" include plural referents unless the context clearly dictates otherwise.

The term "and/or" as used in a phrase such as "A and/or B" herein is intended to mean "A and B", "A or B", "A" or "B".

The term "about" generally refers to a range of numbers that one of skill in the art would consider equivalent to the recited value (i.e., having the same function or result). In many instances, the term "about" may include numbers that are rounded to the nearest significant figure. In certain instances, the term "about" may be used to denote values falling within ±20% of the recited values, e.g. within ±15%, ±10%, ±7.5%, ±5%, ±4%, ±3%, ±2% or ±1% of the recited values.

The term "substantially free" means not added as an excipient.

The term "pH neutral conditions" means between about pH 6.8 and about 7.8.

The term "stable" means the pharmaceutical composition comprises less than about 15 micrograms/mL of hydrazine following storage for 5 days at 25° C. followed by 30 days at 5° C. at pH neutral conditions.

The term "baseline" means the first measurement of the targeted variable just before the administration of the studied therapy.

The term "container" means any coated or uncoated suitable container made using any suitable material, and includes, but is not limited to vials, cartridges, syringes, bottles, and materials such as glass, plastic, and/or any combinations thereof.

Unless the context requires otherwise, the terms "comprise," "comprises," and "comprising" are used on the basis and clear understanding that they are to be interpreted inclusively, rather than exclusively, such that they indicate the inclusion of the recited feature but without excluding one or more other such features.

The term "patient", "subject", "individual" and the like refers to humans.

The term "carrier" used in connection with a pharmaceutical excipient refers to any and all solvents, dispersion media, preservatives, coatings, isotonic and absorption delaying agents, and the like, that are compatible with pharmaceutical administration.

The term "pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methyl-bicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like. Such salts are disclosed in WO 2016/065019 A1.

In one embodiment, the pharmaceutical composition comprises the levodopa phosphate prodrug and the carbidopa phosphate in an aqueous carrier and the pharmaceutical composition is suitable for subcutaneous administration. The pharmaceutical composition comprises a ratio of levodopa 4'-monophosphate to carbidopa 4'-monophosphate of about 20 to about 1. In one embodiment the pharmaceutical composition comprises about 240 mg/mL of levodopa 4'-monophosphate and about 12 mg/mL of carbidopa 4'-monophosphate. In another embodiment the pharmaceutical composition comprises about 360 mg/mL of levodopa 4'-monophosphate and about 18 mg/mL of carbidopa 4'-monophosphate. In another embodiment the pharmaceutical composition comprises about 60 mg/mL of 4'-monophosphate and about 3 mg/mL of carbidopa 4'-monophosphate.

In one embodiment, the concentration of compound (A-1) in the composition is between 216 mg/mL and 264 mg/mL. In another embodiment, the concentration of compound (A-1) is about 240 mg/mL. In one embodiment, the concentration of compound (B-1) in the composition is between 9.6 mg/mL and 13.2 mg/mL. In another embodiment, the concentration of compound (B-1) is about 12 mg/mL. In one embodiment, the concentration of compound (A-1) in the composition is between 216 mg/mL and 264 mg/mL, and the concentration of compound (B-1) in the composition is between 9.6 mg/mL and 13.2 mg/mL. In another embodiment, the concentration of compound (A-1) is about 240 mg/mL, and the concentration of compound (B-1) is about 12 mg/mL. Accordingly, in one embodiment, the concentration of compound (A-1) in the composition is between 216 mg/mL and 264 mg/mL. In another embodiment, the concentration of compound (A-1) is about 240 mg/mL. In one embodiment, the concentration of compound (B-1) in the composition is between 9.6 mg/mL and 13.2 mg/mL. In another embodiment, the concentration of compound (B-1) is about 12 mg/mL. In one embodiment, the concentration of compound (A-1) in the composition is between 216 mg/mL and 264 mg/mL, and the concentration of compound (B-1) in the composition is between 9.6 mg/mL and 13.2 mg/mL. In another embodiment, the concentration of compound (A-1) is about 240 mg/mL, and the concentration of compound (B-1) is about 12 mg/mL. Accordingly, in one embodiment the pharmaceutical composition comprises about 240 mg/mL of levodopa 4'-monophosphate and about 12 mg/mL of carbidopa 4'-monophosphate. In one embodiment, the concentration of compound (A-1) in the composition is between 324 mg/mL and 396 mg/mL. In another embodiment, the concentration of compound (A-1) is about 360 mg/mL. In one embodiment, the concentration of compound (B-1) in the composition is between 16.2 mg/mL and 19.8 mg/mL. In another embodiment, the concentration of compound (B-1) is about 18 mg/mL. In one embodiment, the concentration of compound (A-1) in the composition is between 324 mg/mL and 396 mg/mL, and the concentration of compound (B-1) in the composition is between 16.2 mg/mL and 19.8 mg/mL. In another embodiment, the concentration of compound (A-1) is about 360 mg/mL, and the concentration of compound (B-1) is about 18 mg/mL. Accordingly, in one embodiment the pharmaceutical composition comprises about 360 mg/mL of levodopa 4'-monophosphate and about 18 mg/mL of carbidopa 4'-monophosphate.

In one embodiment, the concentration of compound (A-1) is about 60 mg/mL, and the concentration of compound (B-1) is about 3 mg/mL. Accordingly, in another embodiment, the pharmaceutical composition comprises about 60 mg/mL of 4'-monophosphate and about 3 mg/mL of carbidopa 4'-monophosphate.

In one embodiment, the pharmaceutical composition is manufactured using a neutralizing agent. In one embodiment the neutralizing agent is sodium hydroxide. In another embodiment the neutralizing agent is potassium hydroxide. As described herein, the pharmaceutical composition can have a final pH of about 6.5 to about pH 9.2, including pH values increasing in increments of 0.1 in between 6.5 and 9.2. In one embodiment, the pharmaceutical composition has final pH (e.g. after reconstitution with water) of between about 6.8 and about 7.8. Thus, the pharmaceutical composition may have a final pH selected from about 6.8, 6.9, 7.0, 7.1, 7.2, 7.3, 7.4, 7.5, 7.6, 7.7, or 7.8. In one embodiment, the pharmaceutical composition has final pH of between about 7.0 and about 7.5. Thus, the pharmaceutical composition may have a final pH selected from about 7.0, 7.1, 7.2, 7.3, 7.4, or 7.5.

Formulations comprising the levodopa and carbidopa phosphate prodrugs may undergo oxidation and/or degradation resulting in release of various degradants such as hydrazine and/or 2-methyl-3-(3,4-dihydroxyphenyl)-propionic acid (DHPPA-P). For example, hydrazine may result from oxidative degradation of a carbidopa-4'-monophosphate. Hydrazine is considered an impurity and the release of hydrazine in the pharmaceutical composition should be controlled. In one embodiment, the pharmaceutical composition is stable, releasing less than about 0.50 mg/mL of DHPPA-P after storage for about 5 days at room temperature, for example, 25° C. and about 30 days at refrigerated conditions, for example, at 5° C.

In another embodiment, the pharmaceutical composition comprises less than about 5.4% w/w DHPPA-P at a pH between 6.5 and 9.0 after storage for 5 days at 25° C. followed by 30 days at 5° C. In one embodiment, the pharmaceutical composition releases less than about 15 micrograms/mL of hydrazine after storage for about 5 days at room temperature, for example, 25° C. and about 30 days at refrigerated conditions, for example, at 5° C. Thus, for example, the pharmaceutical composition may comprise less than about 15 micrograms/mL hydrazine following storage for 5 days at 25° C. followed by 30 days at 5° C. at pH neutral conditions.

In some embodiments, the composition is stable (e.g. under the measures set out above) for at least three months at refrigerated conditions, for example, at temperatures between 2° C. to 8° C. and equivalent conditions as established in a 10-cc vial having less than about 9% oxygen in the headspace at 1 atmospheric pressure (e.g. using a 15 cc or 20 cc vial). Preferably the vial (e.g. a 15 cc or 20 cc vial) contains less than about 5.5% oxygen at 1 atmospheric pressure. The oxygen in the vial or other suitable container for storing the composition may be purged to less than about 9% oxygen by purging with nitrogen or any suitable inert gas.

The pharmaceutical compositions of the disclosure exhibit desirable pharmacokinetics following administration to human subjects. In one embodiment, the pharmaceutical composition provides a mean plasma exposure ratio of levodopa to carbidopa as measured by $AUC_{(0-t)}$ to $AUC_{(0-t)}$ between 6.57 and 8.03 levodopa to about 1 carbidopa when administered to adult humans. In another embodiment, the pharmaceutical composition provides a mean plasma exposure ratio of levodopa to carbidopa as measured by $AUC_{(0-t)}$ to $AUC_{(0-t)}$ of about 7.30 levodopa to about 1 carbidopa when administered to adult humans. In particular, the pharmaceutical compositions of the disclosure can provide highly stable steady state plasma levels of levodopa (e.g. following continuous subcutaneous administration). Thus, in one embodiment, the continuous subcutaneous administration of the pharmaceutical composition to a population of adult humans achieves a mean plasma concentration of levodopa having a degree of fluctuation of about 0.3 or less over 2-16 hours following administration, wherein the degree of fluctuation is defined as the $([C_{max}-C_{min}]/C_{ave})$ for the given time period. In another embodiment, the continuous subcutaneous administration of the composition to a population of adult humans achieves a mean plasma concentration of levodopa having a degree of fluctuation of about 0.40 over 2-72 hours following administration, wherein the degree of fluctuation is defined as the $([C_{max}-C_{min}]/C_{ave})$ for the given time period.

In one embodiment, the pharmaceutical composition of the disclosure is substantially antioxidant free. In another embodiment, the composition is substantially arginine free. In another embodiment, the composition is substantially free of ascorbic acid or a pharmaceutically acceptable salt of ascorbic acid. In another embodiment, the composition is substantially free of L-cysteine or a pharmaceutically acceptable salt thereof; N-acetylcysteine (NAC) or a pharmaceutically acceptable salt thereof; glutathione or a pharmaceutically acceptable salt thereof; diacetyl cysteine or a pharmaceutically acceptable salt thereof; and sodium bisulfite, or any combination thereof.

This disclosure also relates to therapeutic methods in which the present pharmaceutical compositions are used. Viewed from this aspect, the disclosure provides a pharmaceutical composition as disclosed herein for use as a medicament. Also provided is the use of a pharmaceutical composition as disclosed herein in therapy. In particular, the disclosure provides methods for the treatment of conditions responsive to levodopa and carbidopa, such as Parkinson's disease, using compositions disclosed herein. In one aspect, the disclosure provides a method of treating Parkinson's disease in a subject, comprising subcutaneously administering a pharmaceutical composition as disclosed herein to a patient in need thereof. Also provided is a pharmaceutical composition as disclosed herein for use in the treatment of Parkinson's disease. Further provided is the use of a compound of formula (A-1) and a compound of formula (B-1) in the preparation of a pharmaceutical composition as disclosed herein for use in the treatment of Parkinson's disease. In one embodiment, the treatment comprises administering the pharmaceutical composition to an adult human patient, wherein the administration provides a plasma exposure ratio of levodopa to carbidopa as measured by $AUC_{(0-t)}$ to $AUC_{(0-t)}$ of about 7.30 to 1. In other aspects and embodiments, the disclosure provides methods in which specific measures of Parkinson's disease are improved. Thus, the disclosure provides a method of improving "off" time of parkinsonian symptoms in a subject, the method comprising subcutaneously administering a pharmaceutical composition as disclosed herein to a patient in need of treatment for Parkinson's disease in an amount effective for reducing parkinsonian symptoms by at least 46% from baseline. The disclosure also provides a method of treating Parkinson's disease in a subject, comprising subcutaneously administering a pharmaceutical composition as disclosed herein to a subject in need of treatment for Parkinson's disease with a baseline Movement Disorder Society-Unified Parkinson's disease Rating Scale (MDS-UPDRS) total score in an amount effective for reducing the baseline MDS-UPDRS total score by at least 9 units. The disclosure also provides a method of treating Parkinson's disease in a subject, comprising subcutaneously administering a pharmaceutical composition as disclosed herein to a subject in need of treatment for Parkinson's disease with a baseline Parkinson's disease Questionnaire-39 items (PDQ-39) summary index score in an amount effective for reducing the baseline PDQ-39 score by at least 6.9 units. The disclosure also provides a method of treating Parkinson's disease in a subject, comprising subcutaneously administering a pharmaceutical composition as disclosed herein to a subject in need of treatment for Parkinson's disease with a baseline Parkinson's disease Sleep Scale-2 (PDSS-2) total score in an amount effective for reducing the baseline PDSS-2 total score by at least 2 units. In embodiments, the treatments disclosed herein can be continued for at least 10 days with no incidence of the subject developing skin nodules. The disclosure also provides a method of reducing incidences of "off" time of parkinsonian symptoms in a subject compared with the subject receiving oral administration of tablets containing levodopa and carbidopa, comprising subcutaneously administering a pharmaceutical composition as disclosed herein to a patient in need of treatment for Parkinson's disease.

The present disclosure also relates to a ready-to-use vial or cartridge or container or enclosure suitable for liquid pharmaceutical dosage formulation containment. Such containment may serve the function of holding a liquid formulation containing one or more of the levodopa phosphate prodrug and carbidopa phosphate prodrug (e.g. in a pharmaceutical composition as disclosed herein). The vials can also serve as storage for powder forms of a levodopa phosphate prodrug and/or a carbidopa phosphate prodrug such that the vial can be in a ready to use format wherein reconstitution with an aqueous vehicle results in a ready to withdraw or load to inject container. A stable pharmaceutical compositions comprises a concentration of levodopa-4'-monophosphate between about 216 mg/mL and about 264 mg/mL, a concentration of carbidopa-4'-monophosphate between about 9.6 mg/mL and about 13.2 mg/m L.

The present disclosure also relates to a ready-to-use vial or cartridge or container or enclosure suitable for liquid pharmaceutical dosage formulation containment. Such containment may serve the function of holding a liquid formulation containing one or more of the levodopa phosphate prodrug and carbidopa phosphate prodrug. The vials can also serve as storage for powder forms of a levodopa phosphate prodrug and/or a carbidopa phosphate prodrug such that the vial can be in a ready to use format wherein reconstitution with an aqueous vehicle results in a ready to withdraw or load to inject container.

As noted above, carbidopa is dosed with levodopa to improve the levodopa exposure by inhibiting the aromatic-L-amino acid decarboxylase (DDC) enzyme, which metabolizes levodopa. Orally dosing levodopa to carbidopa at a 4:1 ratio has been used in the past to inhibit the DDC enzyme. An improved ratio for the composition comprising levodopa phosphate prodrug and carbidopa phosphate prodrug for subcutaneous administration was discovered to be about 20:1 based on the levodopa to carbidopa plasma exposure ratio observed in humans. An advantage of using a 20:1 weight by weight ratio of compositions comprising levodopa phosphate prodrug and carbidopa phosphate prodrug is that excess carbidopa prodrug dosing is reduced.

Example 1A

Safety, Tolerability, and Pharmacokinetics in Healthy Subjects

This example demonstrates that the pharmaceutical composition of levodopa 4'-monophosphate and carbidopa 4'-monophosphate at a ratio of 20:1 is safe and also evaluates its pharmacokinetics.

Methodology

To assess safety, tolerability, and pharmacokinetics of the levodopa 4'-monophosphate and carbidopa 4'-monophosphate delivered as a single continuous subcutaneous infusion (CSCI) over 16 hours, a total of 8 healthy older (45-75-year-old) human subjects participated in a single-blind, placebo-controlled, 3 period cross-over design clinical study. Each dose of the levodopa 4'-monophosphate and carbidopa 4'-monophosphate composition or placebo was administered in a single blind manner as a single CSCI to the abdomen delivered at a constant rate over a 16-hour period via an infusion set connected to an ambulatory pump. Regimens A, B, C, and D consisted of 640/160 mg levodopa 4'-monophosphate/carbidopa 4'-monophosphate, 640/64 mg levodopa 4'-monophosphate/carbidopa 4'-monophosphate CSCI, 640/32 mg levodopa 4'-monophosphate/carbidopa 4'-monophosphate CSCI, or placebo CSCI, respectively, delivered in the abdomen at a constant rate over 16 hours. Blood samples were collected for pharmacokinetic analysis prior to priming of catheter, prior to infusion (0 hour), and at 0.5, 1, 2, 4, 8, 12, 16, 20, 24, 26 and 28 hours after start of infusion from each of the of 8 healthy older (45-75-year-old) human subjects.

Population

Qualified subjects were healthy male and female volunteers whose ages were between 45 and 75 years, inclusive. If female, subject must be postmenopausal for at least 1 year or surgically sterile. Exclusion criteria included a history of significant skin conditions or disorders (e.g., psoriasis, atopic dermatitis, etc.) or evidence of recent sunburn, acne, scar tissue, tattoo, open wound, branding, or colorations.

Safety Results

No pattern was evident with regard to the nature or frequency of treatment-emergent adverse events following CSCI infusion or bolus injection of the levodopa 4'-monophosphate and carbidopa 4'-monophosphate composition compared to subjects who received placebo. All regimens tested were well tolerated by the subjects. No concerning patterns of adverse events or laboratory findings were reported. There were no notable observations on individual measurements for blood pressure or pulse rate, nor from quantitative measurements from the ECGs.

Pharmacokinetic Results

Figure 2:
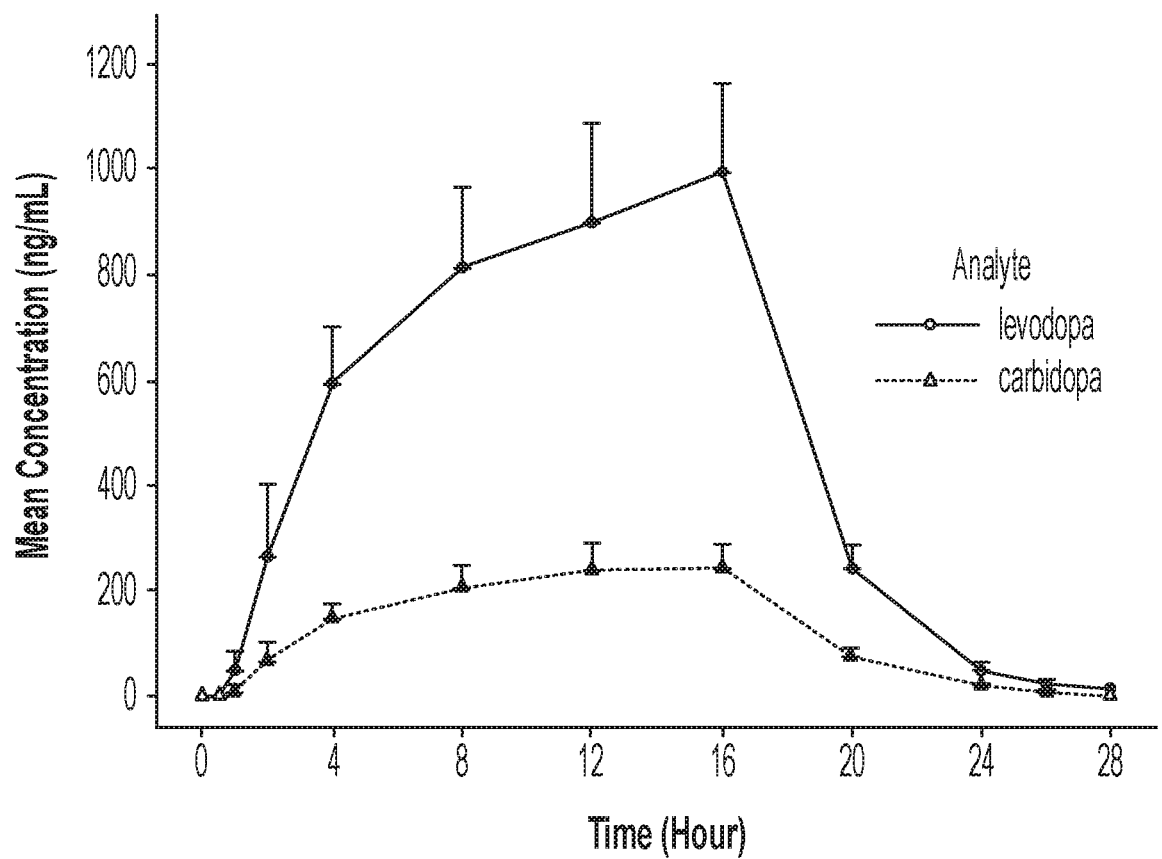
FIG. 2 is a plasma time-concentration profile of levodopa and carbidopa levels in healthy human volunteers after subcutaneous administration of a pharmaceutical composition of levodopa 4'-monophosphate and carbidopa 4'-monophosphate at a ratio of 10:1.
Figure 3:
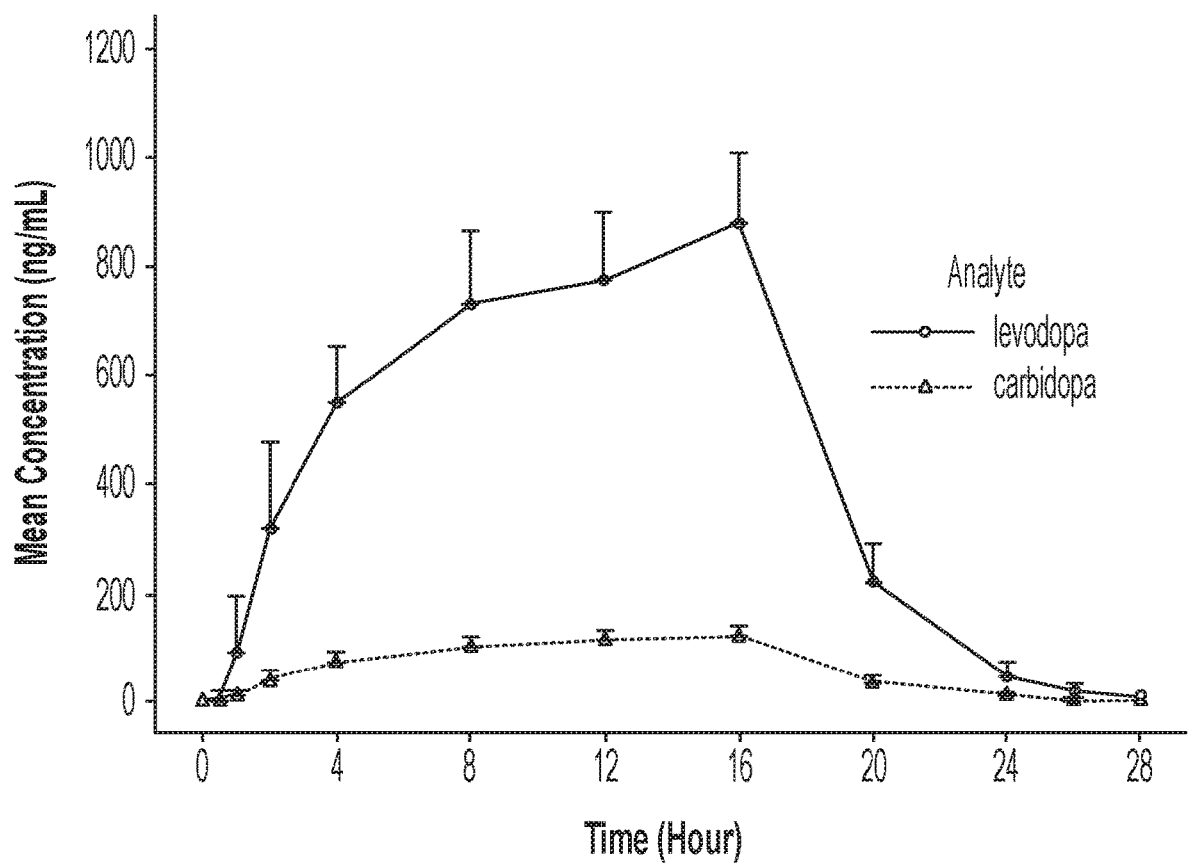
FIG. 3 is a plasma time-concentration profile of levodopa and carbidopa levels in healthy human volunteers after subcutaneous administration of a pharmaceutical composition of levodopa 4'-monophosphate and carbidopa 4'-monophosphate at a ratio of 20:1.
Figure 4:
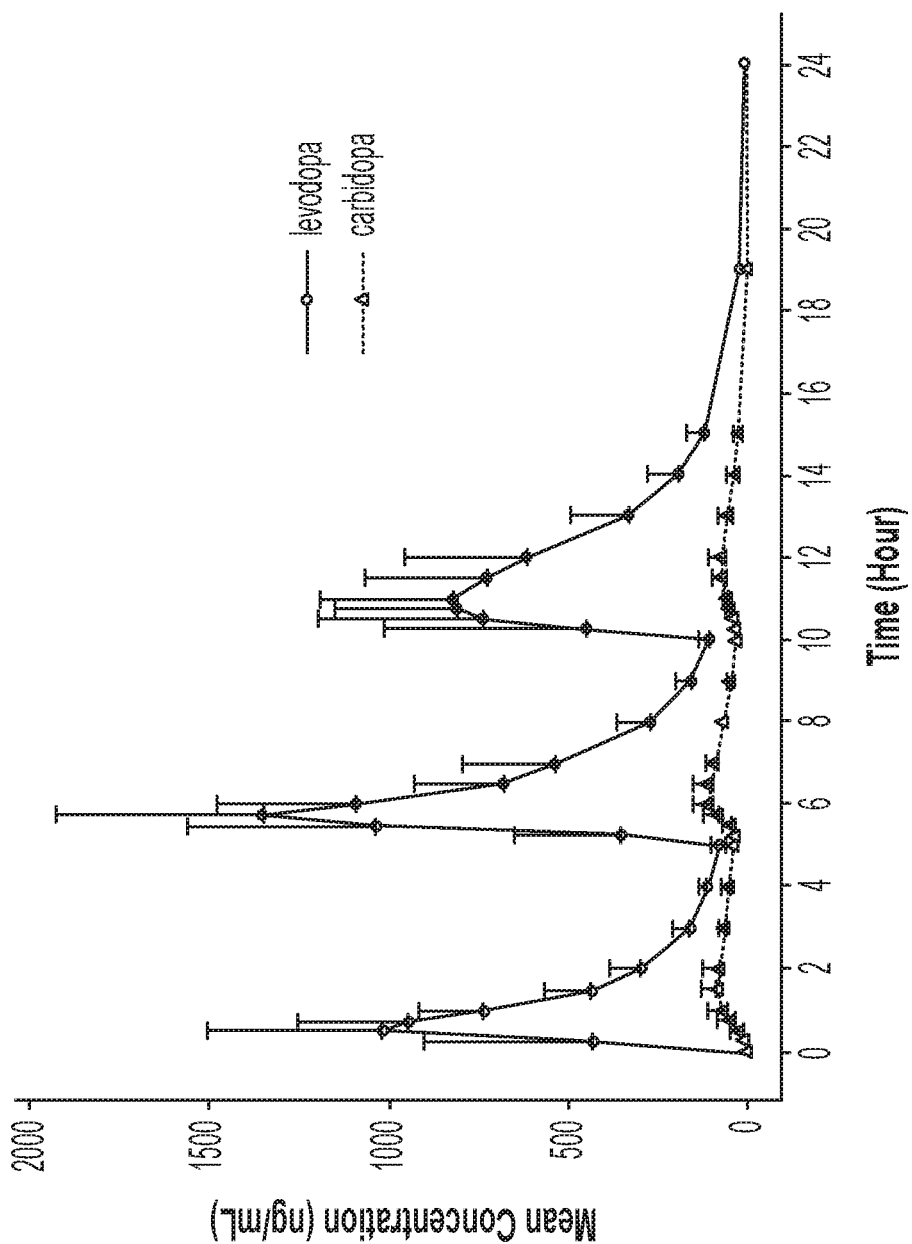
FIG. 4 is a plasma time-concentration profile of levodopa and carbidopa levels in healthy human volunteers after oral administration of a pharmaceutical composition of levodopa and carbidopa at a ratio of 4:1.
Figure 6:
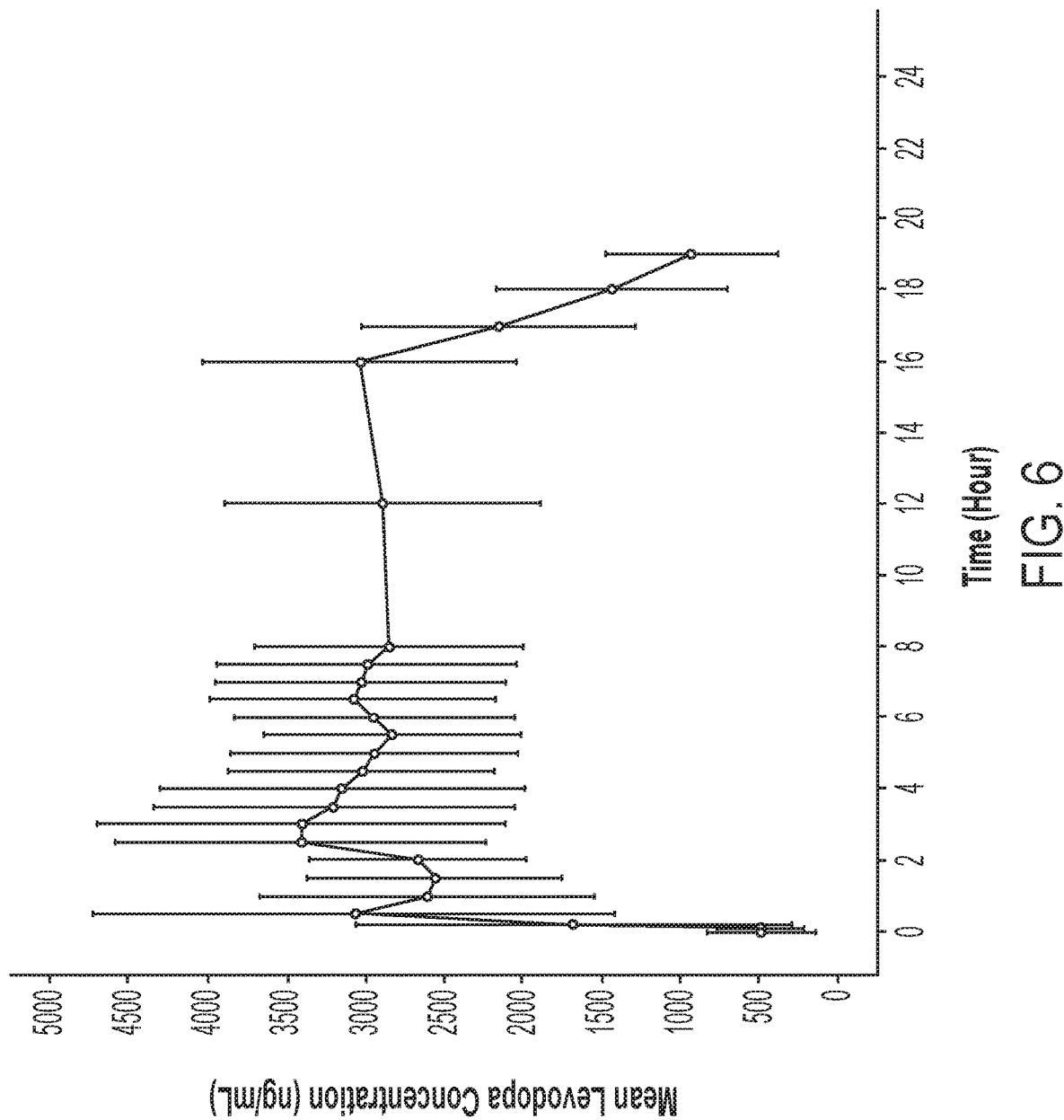
FIG. 6 is a plasma time-concentration profile of levodopa levels in human patients after intestinal administration of Duodopa® at a ratio of levodopa to carbidopa of 4:1.
Figure 7:
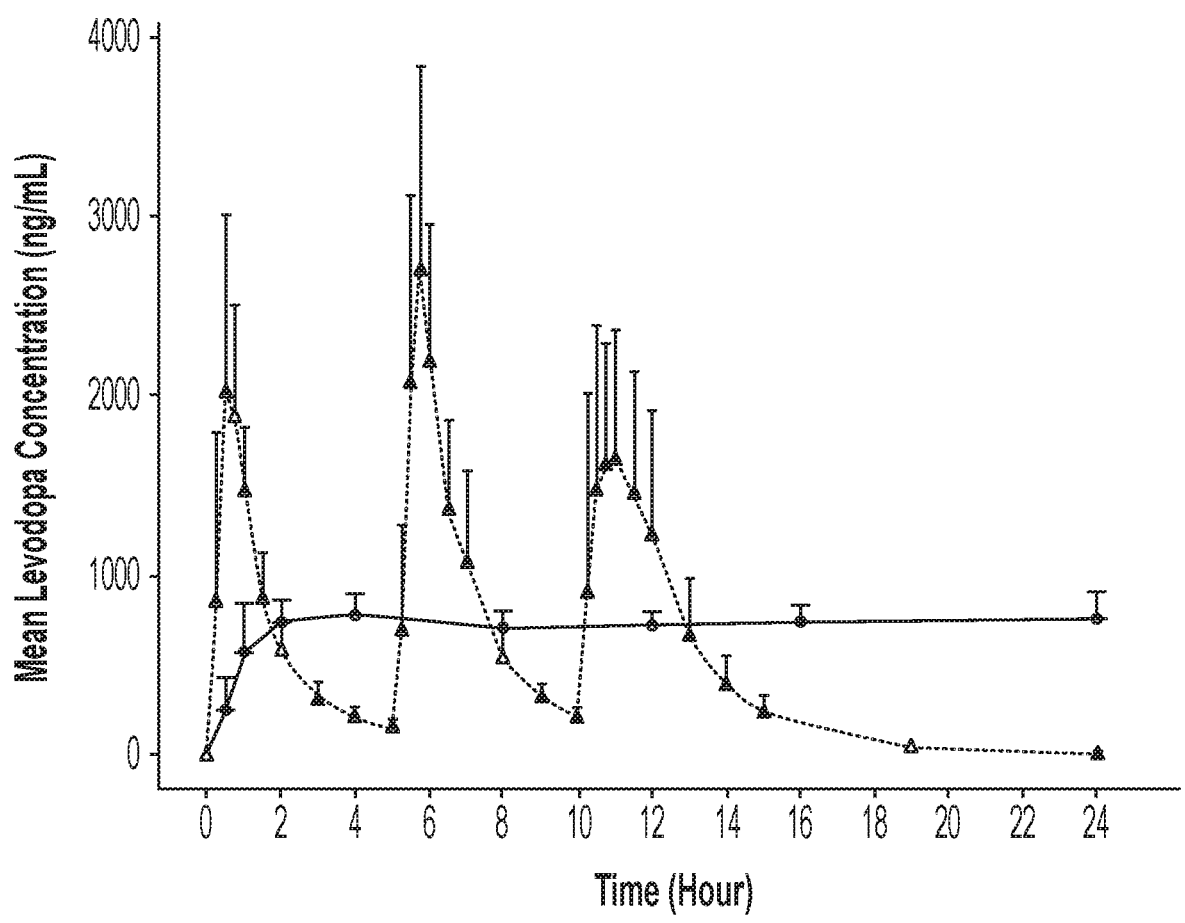
FIG. 7 is a comparison of plasma time-concentration profiles of levodopa levels in healthy human volunteers of levodopa 4'-monophosphate and carbidopa 4'-monophosphate at a 20:1 ratio administered subcutaneously and levodopa and carbidopa at a ratio 4:1 administered orally. Oral levodopa plasma concentrations were scaled up by a factor of 2.

As shown in FIGS. 1-3, compositions of the levodopa 4'-monophosphate and carbidopa 4'-monophosphate were delivered to the healthy human volunteers subcutaneously at the w/w various ratios of 4:1 (regimen A, FIG. 1); 10:1 (regimen B, FIG. 2); and 20:1 (regimen C, FIG. 3), respectively of levodopa 4'-monophosphate to carbidopa 4'-monophosphate. The time-concentration plasma level profiles for each of the ratios of the levodopa 4'-monophosphate to carbidopa 4'-monophosphate delivered subcutaneously (FIGS. 1-3) were compared to the time-concentration profiles of levodopa and carbidopa plasma levels obtained from oral administration to the same humans of levodopa and carbidopa at a weight by weight ratio of 4:1 levodopa:carbidopa (FIG. 4). In addition, the time-concentration profile in healthy human volunteers of levodopa plasma levels obtained via subcutaneous administration of levodopa 4'-monophosphate and carbidopa 4'-monophosphate at a 20:1 ratio (FIG. 5) was compared with the time-concentration profile in patients of levodopa plasma levels obtained via intraduodenal administration of Duodopa® at a w/w ratio of 4:1 levodopa to carbidopa (FIG. 6). Furthermore, the time-concentration profile in healthy human volunteers of levodopa plasma levels obtained via subcutaneous administration of levodopa 4'-monophosphate and carbidopa 4'-monophosphate at a 20:1 w/w ratio was compared to the time-concentration profile in patients of levodopa plasma levels obtained via oral administration of levodopa and carbidopa at a w/w ratio of 4:1 levodopa to carbidopa (FIG. 7).

FIG. 1 provides a time-concentration profile of levodopa and carbidopa plasma levels in healthy human volunteers after subcutaneous administration CSCI of a composition comprising levodopa 4'-monophosphate and carbidopa 4'-monophosphate at a w/w ratio of 4:1 (640 mg levodopa 4'-monophosphate/160 mg carbidopa 4'-monophosphate). Healthy older volunteers were dosed in a 4:1 ratio of levodopa 4'-monophosphate to carbidopa 4'-monophosphate. As shown in FIG. 1, the plasma exposure ratio of levodopa $AUC_{(0-t)}$/carbidopa $AUC_{(0-t)}$ was 1.79 to 1 compared with 7.39 to 1 for oral levodopa and carbidopa administered at a w/w ratio of 4:1 (FIG. 4).

FIG. 2 provides a time-concentration profile of levodopa and carbidopa plasma levels in healthy older human volunteers after continuous subcutaneous infusion of a composition comprising levodopa 4'-monophosphate and carbidopa 4'-monophosphate at a w/w ratio of 10:1 (640 mg levodopa 4'-monophosphate/64 mg carbidopa 4'-monophosphate). Results from the exposure ratio analysis shows that the levodopa:carbidopa plasma exposure ratios were $AUC_{(0-t)}$/carbidopa $AUC_{(0-t)}$ was 3.94 to 1 compared with 7.39 to 1 for oral levodopa and carbidopa administered at a w/w ratio of 4:1 (FIG. 4).

Surprisingly, it was discovered that a 20:1 dosing ratio (640 mg levodopa 4'-monophosphate/32 mg carbidopa 4'-monophosphate) could produce a levodopa to carbidopa exposure ratio for subcutaneously administered levodopa 4'-monophosphate and carbidopa 4'-monophosphate similar to oral levodopa and carbidopa dosed at a ratio of 4:1 (e.g. Sinemet®). FIG. 3 provides a time-concentration profile of levodopa and carbidopa plasma levels in healthy human volunteers after continuous subcutaneous infusion dosing of a pharmaceutical composition comprising levodopa-4'-monophosphate and carbidopa-4'-monophosphate in humans. As shown in FIG. 3, the CSCI dosing of the composition led to the unexpected finding that at a w/w ratio of 20:1 (640 mg levodopa 4'-monophosphate to 32 mg carbidopa 4'-monophosphate) results in comparable levodopa/carbidopa exposure ratios to dosing 4:1 oral levodopa to carbidopa (FIG. 4). The exposure ratio was calculated as levodopa AUCo-t/carbidopa AUCo-t. Results from the exposure ratio analysis unexpectedly shows that the levodopa:carbidopa plasma exposure ratio was 7.30 to 1 ng*h/mL for the composition comprising levodopa 4'-monophosphate and carbidopa 4'-monophosphate administered subcutaneously at a w/w ratio of 20:1, which is within about 99% or 0.09 (units) of the 7.39 to 1 value for oral levodopa and carbidopa administered at a w/w ratio of 4:1 (e.g. Sinemet®) (FIG. 4). Furthermore, the 20:1 levodopa 4'-monophosphate and carbidopa 4'-monophosphate composition results in an overall theoretical reduction in hydrazine exposure of about 80% compared to the 4:1 levodopa 4'-monophosphate to carbidopa 4'-monophosphate ratio, which beneficially in addition allows for more levodopa 4'-monophosphate in a fixed volume composition of levodopa 4'-monophosphate and carbidopa 4'-monophosphate.

FIG. 4 provides a time-concentration profile of levodopa and carbidopa plasma levels in healthy older human volunteers after oral administration of a combination of levodopa and carbidopa at a w/w ratio of 4:1. A total of 300/75 mg levodopa/carbidopa was administered orally to 8 healthy older (45-75 years old) human subjects in an open label study as 3 divided doses of 100/25 mg levodopa/carbidopa. Doses were administered at 0, 5, and 10 hours. Blood samples were collected for pharmacokinetic analysis prior to first dose (0 hour) and at 0.25, 0.5, 0.75, 1, 1.5, 2, 3, 4, prior to second dose (5 hour), 5.25, 5.5, 5.75, 6, 6.5, 7, 8, 9, prior to third dose (10 hour), 10.25, 10.5, 10.75, 11, 11.5, 12, 13, 14, 15, 19, and 24 hours after initial dosing on Day 1.

Results

Figure 5:
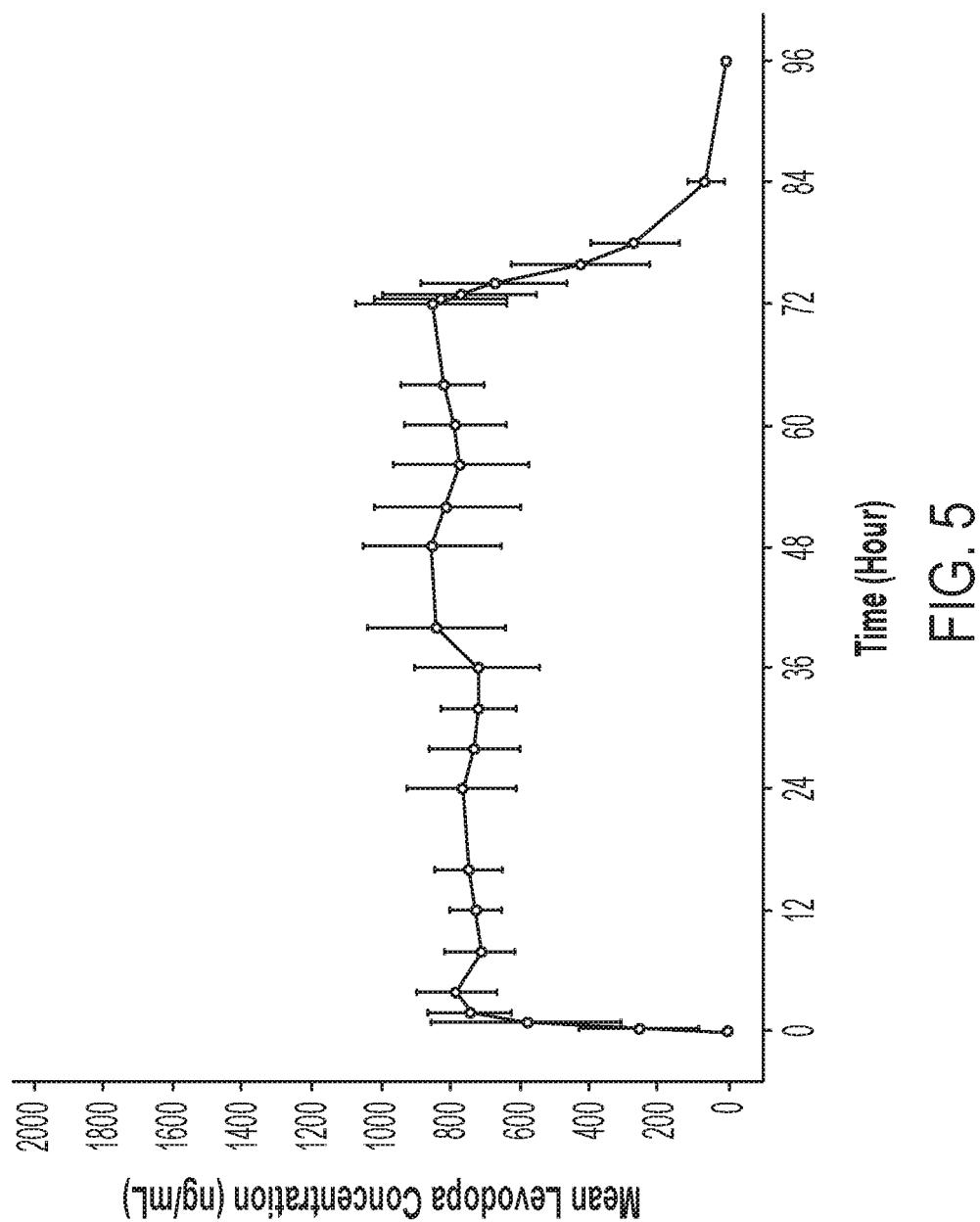
FIG. 5 is a plasma time-concentration profile of levodopa plasma levels (±standard deviation) in healthy human volunteers during subcutaneous administration of a bolus dose of a pharmaceutical composition of levodopa 4'-monophosphate and carbidopa 4'-monophosphate at a ratio of 20:1 followed by a 72-hour dose of a continuous subcutaneous infusion of the pharmaceutical composition.

FIG. 5 provides a time-concentration profile and Table 1 provides the pharmacokinetic parameters of levodopa and carbidopa plasma levels in healthy older human volunteers after subcutaneous administration of a pharmaceutical composition of levodopa 4'-monophosphate and carbidopa 4'-monophosphate at a w/w ratio of 20:1 as an initial bolus infusion over 5 minutes followed by a continuous subcutaneous infusion over 72 hours (960 mg/48 mg levodopa 4'-monophosphate/carbidopa 4'-monophosphate).

TABLE 1

Geometric Mean (Mean, % CV) Pharmacokinetic Parameters of the Composition Delivered as Initial Bolus Infusion Followed by CSCI in Healthy Human Volunteers
N = 5[a]

| Pharmacokinetic Parameters (units) | | Carbidopa | Levodopa |
|---|---|---|---|
| $C_{max}$ | ng/mL | 121 (123 | 931 (941, 17) |
| $T_{max}$[b] | h | 48.0 (1.0-64.0) | 52.0 (1.0-72.0) |
| $AUC_t$ | ng · h/mL | 7930 (8100, 23) | 59100 (59900, 20) |
| $AUC_{inf}$ | ng · h/mL | 8070 (8240, 23) | 59200 (60100, 20) |
| $t_{1/2}$[c] | h | 3.41 (0.498) | 2.53 (0.525) |
| DFL (2-16)[b] | (ng · h/mL)/mg | 0.246 (0.219-0.379) | 0.202 (0.098-0.417) |
| DFL (2-72)[b] | (ng · h/mL)/mg | 0.356 (0.337-0.441) | 0.412 (0.205-0.431) |

[a]10/200 mg levodopa 4'-monophosphate/carbidopa 4'-monophosphate delivered as an initial bolus infusion followed by 48/960 mg levodopa 4'-monophosphate/carbidopa 4'-monophosphate per 24 hours (total infusion time 72 hours).
[b]Median (minimum through maximum).
[c]Harmonic mean (pseudo-standard deviation).

As shown in Table 2, the continuous subcutaneous infusion over 72 hours of the composition (960 mg/48 mg levodopa 4'-monophosphate/carbidopa 4'-monophosphate) achieves a mean plasma concentration of levodopa having a degree of fluctuation of about 0.3 or less over 2-16 hours, wherein the degree of fluctuation is calculated as the ($[C_{max}-C_{min}]/C_{ave}$) for the given time period of 2 hours to 72 hours. The $C_{max}$ is the maximum (or peak) blood plasma concentration of levodopa achieved after continuous subcutaneous infusion of the composition (960 mg/48 mg levodopa 4'-monophosphate/carbidopa 4'-monophosphate). $C_{min}$ is the minimum observed blood plasma concentration from 2 hours to 72 hours of levodopa during continuous subcutaneous infusion of the composition (960 mg/48 mg levodopa 4'-monophosphate/carbidopa 4'-monophosphate). $C_{ave}$ is the average blood plasma concentration of levodopa observed during continuous subcutaneous infusion of the composition (960 mg/48 mg levodopa 4'-monophosphate/carbidopa 4'-monophosphate).

The continuous subcutaneous infusion over 72 hours of the composition (960 mg/48 mg levodopa 4'-monophosphate/carbidopa 4'-monophosphate) achieves a stable plasma concentration of levodopa having a degree of fluctuation of about 0.4 or less over 2-72 hours during administration wherein the degree of fluctuation is defined as the ($[C_{max}-C_{min}]/C_{ave}$) for the given time period. The low levodopa concentration steady state ($C_{ss}$) exposure fluctuation (ng/mL) was similar to that seen with Duodopa® (4:1 ratio of levodopa to carbidopa monohydrate), the current standard of care requiring intraduodenal administration.

TABLE 2

Pharmacokinetic parameters of levodopa and carbidopa plasma levels in Healthy Human Volunteers

| | Pharmacokinetic Parameters | | |
|---|---|---|---|
| | Composition (N = 5) | Duodopa (N = 18) | Oral levodopa/ carbidopa (N = 8) |
| Levodopa degree of fluctuation (2-16 hours) | 0.24* ± 0.12 | 0.52 ± 0.20 | 4.1 ± 1.4 |

*p < 0.001 compared to oral degree of fluctuation

FIG. 6 provides the time-concentration profile in patients of levodopa plasma levels obtained via intraduodenal administration of Duodopa® at a ratio of 4:1 levodopa to carbidopa. A comparison of the FIGS. 5 and 6 shows that the time-concentration profile of levodopa and carbidopa plasma levels in healthy older human volunteers after subcutaneous administration of a pharmaceutical composition comprising levodopa 4'-monophosphate and carbidopa 4'-monophosphate at a w/w ratio of 20:1 provides a more steady concentration of levodopa in plasma over time versus Duodopa®.

FIG. 7 is a comparison of time-concentration profiles of levodopa plasma levels in healthy older human volunteers following administration of continuous subcutaneous infusion of a pharmaceutical composition of levodopa 4'-monophosphate and carbidopa 4'-monophosphate at a 20:1 ratio w/w and a pharmaceutical composition comprising a combination of levodopa and carbidopa at a w/w ratio of 4:1 administered orally. The oral levodopa exposure data was scaled up (multiplied by 2) to match the average levodopa exposure achieved by the levodopa 4'-monophosphate and carbidopa 4'-monophosphate pharmaceutical composition. As shown in FIG. 7, the subcutaneously administered pharmaceutical composition of levodopa 4'-monophosphate and carbidopa 4'-monophosphate at a 20:1 ratio (solid line) demonstrated the ability to maintain levodopa plasma concentration at steady state exposure within minimal steady state fluctuation and maintain levodopa plasma exposure for 24 hours, whereas the oral levodopa plasma concentration (dotted line) fluctuated over time.

Example 1B

Safety, Tolerability, and Pharmacokinetics of 72-Hour Subcutaneous Infusions in Subjects with Parkinson's disease This example demonstrates that the pharmaceutical composition of levodopa 4'-monophosphate and carbidopa 4'-monophosphate at a ratio of 20:1 is safe and also evaluates its pharmacokinetics over 72 hours.

Methodology

To assess safety, tolerability, and pharmacokinetics of the levodopa 4'-monophosphate and carbidopa 4'-monophosphate delivered as a single continuous subcutaneous infusion (CSCI) over 72 hours a single-blind, single-dose escalation study evaluated subcutaneous infusions of the pharmaceutical composition of levodopa 4'-monophosphate and carbidopa 4'-monophosphate and placebo in approximately 16 subjects having Parkinson's disease.

Four treatment groups with up to four subjects in each group received a bolus dose of the pharmaceutical composition of levodopa 4'-monophosphate and carbidopa 4'-monophosphate at a ratio of 20:1 (200 mg/10 mg) followed by a 72-hour dose of the pharmaceutical composition of levodopa 4'-monophosphate and carbidopa 4'-monophosphate at a ratio of 20:1 by CSCI via an infusion pump. A first group received 960/48 mg, a second group received 2400/120 mg, a third group received 3600/180 mg, and a fourth group received 4800/240 mg of the pharmaceutical composition of levodopa 4'-monophosphate and carbidopa 4'-monophosphate by CSCI via an infusion pump.

Population

Qualified subjects were adult male and female subjects, ages 45 to 85, with a diagnosis of idiopathic Parkinson's disease, who are levodopa responsive, in general good health, and are on a stable oral levodopa regimen receiving at least three doses per day.

Figure 16A:
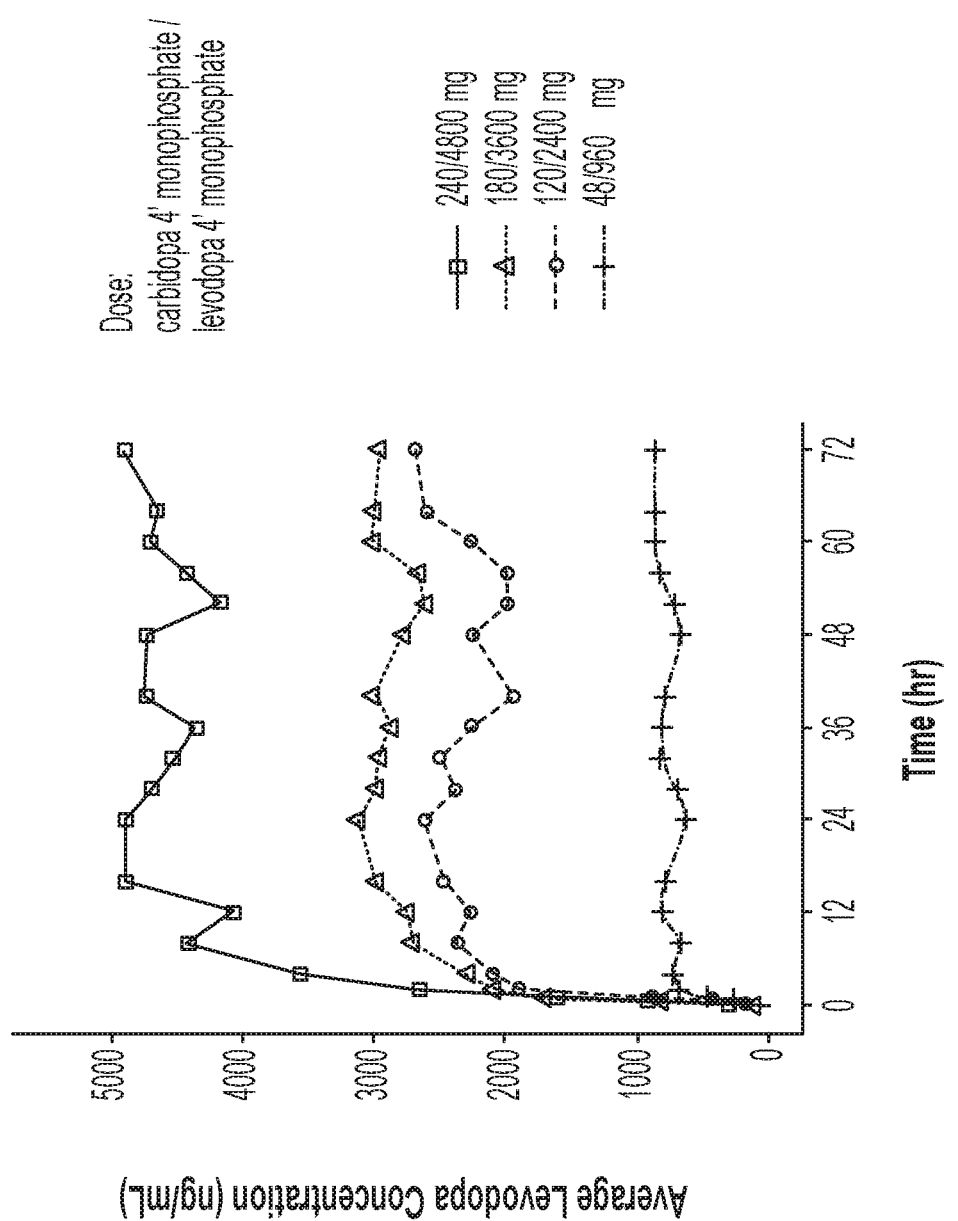
FIG. 16A is a plasma time-concentration profile of levodopa plasma levels in Parkinson's Disease patients after subcutaneous administration of an initial bolus dose, followed by a continuous subcutaneous administration over 72 hours of various doses of the pharmaceutical composition having a ratio of 20:1 levodopa 4' monophosphate to carbidopa 4' monophosphate.
Figure 16B:
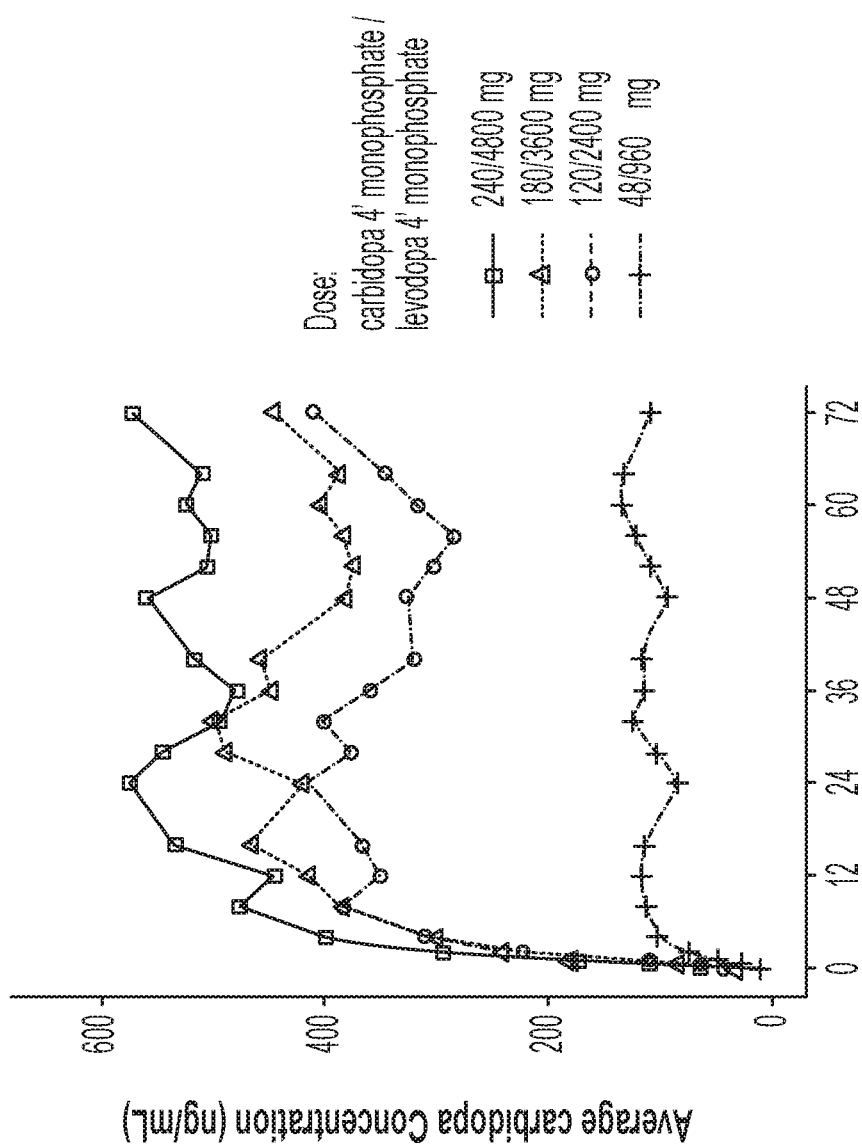
FIG. 16B is a plasma time-concentration profile of carbidopa plasma levels in Parkinson's Disease patients after subcutaneous administration of an initial bolus dose, followed by a continuous subcutaneous administration over 72 hours of various doses of the pharmaceutical composition having a ratio of 20:1 levodopa 4' monophosphate to carbidopa 4' monophosphate.

As shown in FIG. 16A and FIG. 16B, the average measured concentration of each of levodopa and carbidopa from various doses of the pharmaceutical composition having a ratio of 20:1 levodopa 4' monophosphate to carbidopa 4' monophosphate remained constant over 72 hours.

Example 2

Stability

This example demonstrates that the pharmaceutical composition of levodopa 4'-monophoshate and carbidopa 4'-monophosphate at a ratio of 20:1 is stable over time.

Methodology

Various aqueous pharmaceutical compositions comprising levodopa 4'-monophosphate prodrug corresponding in structure to formula (A-1) and carbidopa 4'-monophosphate prodrug corresponding in structure to formula (B-1), water, and sufficient neutralizing agent to obtain the final measured pH were prepared as shown in Table 3. The pharmaceutical compositions having the formulations as shown in Table 3 were prepared and filled in a 10-cc vial (having a maximum fill volume of about 13.5 mL) for a total liquid volume of about 11 mL and the rest of the vial volume was purged with nitrogen to leave about a 5.5% oxygen headspace.

TABLE 3

Exemplary Formulations

| Formulation | Nominal carbidopa 4'-mono-phosphate Conc. (mg/mL) | Nominal levodopa 4'-mono-phosphate Conc. (mg/mL) | Neutral-izing Agent | pH | Temp. (° C.) |
| --- | --- | --- | --- | --- | --- |
| 1 | 12 | 240 | NaOH | 6.59 | 23.8 |
| 2 | 12 | 240 | NaOH | 7.13 | 23.3 |
| 3 | 12 | 240 | NaOH | 7.72 | 23.9 |
| 4 | 12 | 240 | NaOH | 8.54 | 23.8 |
| 5 | 12 | 240 | NaOH | 9.13 | 23.6 |
| 6 | 18 | 360 | NaOH | 6.62 | 23.3 |
| 7 | 18 | 360 | NaOH | 7.12 | 23.9 |
| 8 | 18 | 360 | NaOH | 7.95 | 24.0 |
| 9 | 18 | 360 | NaOH | 8.63 | 23.1 |
| 10 | 18 | 360 | NaOH | 9.23 | 23.1 |
| 11 | 3 | 60 | NaOH | 6.62 | 23.8 |
| 12 | 3 | 60 | NaOH | 6.97 | 23.8 |
| 13 | 3 | 60 | NaOH | 7.45 | 23.3 |
| 14 | 3 | 60 | NaOH | 8.04 | 23.4 |
| 15 | 3 | 60 | NaOH | 8.68 | 23.0 |
| 16 | 12 | 240 | KOH | 7.45 | 23.6 |

The amounts of DHPPA-P and hydrazine were separately measured. The measurement of hydrazine levels was based on the derivatization of hydrazine to benzalazine and the method included gradient reversed phase high performance liquid chromatography (HPLC) with ultraviolet (UV) detection to measure hydrazine and DHPPA-P.

Stability Results

Tables 4-7 show the measured DHPPA-P and hydrazine release respectively over time for formulations 1-16 in Table 3. DHPPA-P was measured as mg/mL and % w/w. The % w/w was calculated as the amount of DHPPA-P per amount of carbidopa 4'-monophosphate times 100. Hydrazine was measured as micrograms/mL and % w/w. The % w/w was calculated as the amount of hydrazine per amount of carbidopa 4'-monophosphate times 100.

TABLE 4

DHPPA-P mg/mL over time

| Nominal carbidopa 4'-monophosphate Conc. (mg/mL) | Nominal levodopa 4'-monophosphate Conc. (mg/mL) | Neutralizing Agent | pH | DHPPA-P after 5 days at 25° C. plus 30 days at 5° C. | DHPPA-P after 5 days at 25° C. plus 65 days at 5° C. |
|---|---|---|---|---|---|
| 12 | 240 | NaOH | 6.59 | 0.08 | 0.09 |
| 12 | 240 | NaOH | 7.13 | 0.15 | 0.18 |
| 12 | 240 | NaOH | 7.72 | 0.22 | 0.23 |
| 12 | 240 | NaOH | 8.54 | 0.21 | 0.22 |
| 12 | 240 | NaOH | 9.13 | 0.23 | 0.23 |
| 18 | 360 | NaOH | 6.62 | 0.04 | 0.05 |
| 18 | 360 | NaOH | 7.12 | 0.09 | 0.10 |
| 18 | 360 | NaOH | 7.95 | 0.15 | 0.17 |
| 18 | 360 | NaOH | 8.63 | 0.19 | 0.22 |
| 18 | 360 | NaOH | 9.23 | 0.23 | 0.28 |
| 3 | 60 | NaOH | 6.62 | 0.08 | 0.09 |
| 3 | 60 | NaOH | 6.97 | 0.12 | 0.14 |
| 3 | 60 | NaOH | 7.45 | 0.14 | 0.15 |
| 3 | 60 | NaOH | 8.04 | 0.15 | 0.14 |
| 3 | 60 | NaOH | 8.68 | 0.14 | 0.14 |
| 12 | 240 | KOH | 7.45 | 0.16 | 0.18 |

TABLE 5

DHPPA-P % w/w (DHPPA-P/carbidopa 4'-monophosphate) over time

| Nominal carbidopa 4'-monophosphate Conc. (mg/mL) | Nominal levodopa 4'-monophosphate Conc. (mg/mL) | Neutralizing Agent | pH | DHPPA-P after 5 days at 25° C. plus 30 days at 5° C. | DHPPA-P after 5 days at 25° C. plus 65 days at 5° C. |
|---|---|---|---|---|---|
| 12 | 240 | NaOH | 6.59 | 0.63 | 0.75 |
| 12 | 240 | NaOH | 7.13 | 1.26 | 1.51 |
| 12 | 240 | NaOH | 7.72 | 1.8 | 1.93 |
| 12 | 240 | NaOH | 8.54 | 1.73 | 1.84 |
| 12 | 240 | NaOH | 9.13 | 1.88 | 1.93 |
| 18 | 360 | NaOH | 6.62 | 0.24 | 0.28 |
| 18 | 360 | NaOH | 7.12 | 0.49 | 0.54 |
| 18 | 360 | NaOH | 7.95 | 0.82 | 0.95 |
| 18 | 360 | NaOH | 8.63 | 1.08 | 1.22 |
| 18 | 360 | NaOH | 9.23 | 1.28 | 1.57 |
| 3 | 60 | NaOH | 6.62 | 2.77 | 3.10 |
| 3 | 60 | NaOH | 6.97 | 4.07 | 4.57 |
| 3 | 60 | NaOH | 7.45 | 4.70 | 5.03 |
| 3 | 60 | NaOH | 8.04 | 4.87 | 4.83 |
| 3 | 60 | NaOH | 8.68 | 4.53 | 4.80 |
| 12 | 240 | KOH | 7.45 | 1.36 | 1.53 |

TABLE 6

Hydrazine µg/mL over time

| Nominal carbidopa 4'-monophosphate Conc. (mg/mL) | Nominal levodopa 4'-monophosphate Conc. (mg/mL) | Neutralizing Agent | pH | Hydrazine after 5 days at 25° C. plus 30 days at 5° C. | Hydrazine after 5 days at 25° C. plus 65 days at 5° C. |
|---|---|---|---|---|---|
| 12 | 240 | NaOH | 6.59 | 13.7 | 18.8 |
| 12 | 240 | NaOH | 7.13 | 9.8 | 12.5 |
| 12 | 240 | NaOH | 7.72 | 5.6 | 5.5 |
| 12 | 240 | NaOH | 8.54 | 3.3 | 5.1 |
| 12 | 240 | NaOH | 9.13 | 2.9 | 3.9 |
| 18 | 360 | NaOH | 6.62 | 13.2 | 16.8 |
| 18 | 360 | NaOH | 7.12 | 9.6 | 17.7 |
| 18 | 360 | NaOH | 7.95 | 6.0 | 9.4 |
| 18 | 360 | NaOH | 8.63 | 6.5 | 5.8 |
| 18 | 360 | NaOH | 9.23 | 4.0 | 5.6 |
| 3 | 60 | NaOH | 6.62 | 6.5 | 7.8 |
| 3 | 60 | NaOH | 6.97 | 4.1 | 4.1 |
| 3 | 60 | NaOH | 7.45 | 1.7 | 2.3 |
| 3 | 60 | NaOH | 8.04 | 1.0 | 1.3 |
| 3 | 60 | NaOH | 8.68 | 1.0 | 1.2 |
| 12 | 240 | KOH | 7.45 | 6.3 | 8.5 |

TABLE 7

Hydrazine levels % w/w (hydrazine/carbidopa 4'-monophosphate) over time

| Nominal carbidopa 4'-monophosphate Conc. (mg/mL) | Nominal levodopa 4'-monophosphate Conc. (mg/mL) | Neutralizing Agent | pH | Hydrazine 5 days at 25° C. plus 30 days at 5° C. | Hydrazine 5 days at 25° C. plus 65 days at 5° C. |
|---|---|---|---|---|---|
| 12 | 240 | NaOH | 6.59 | 0.11 | 0.16 |
| 12 | 240 | NaOH | 7.13 | 0.08 | 0.10 |
| 12 | 240 | NaOH | 7.72 | 0.05 | 0.05 |
| 12 | 240 | NaOH | 8.54 | 0.03 | 0.04 |
| 12 | 240 | NaOH | 9.13 | 0.02 | 0.03 |
| 18 | 360 | NaOH | 6.62 | 0.07 | 0.09 |
| 18 | 360 | NaOH | 7.12 | 0.05 | 0.10 |
| 18 | 360 | NaOH | 7.95 | 0.03 | 0.05 |
| 18 | 360 | NaOH | 8.63 | 0.04 | 0.03 |
| 18 | 360 | NaOH | 9.23 | 0.02 | 0.03 |
| 3 | 60 | NaOH | 6.62 | 0.22 | 0.26 |
| 3 | 60 | NaOH | 6.97 | 0.14 | 0.14 |
| 3 | 60 | NaOH | 7.45 | 0.06 | 0.08 |
| 3 | 60 | NaOH | 8.04 | 0.03 | 0.04 |
| 3 | 60 | NaOH | 8.68 | 0.03 | 0.04 |
| 12 | 240 | KOH | 7.45 | 0.05 | 0.07 |

Figure 8:
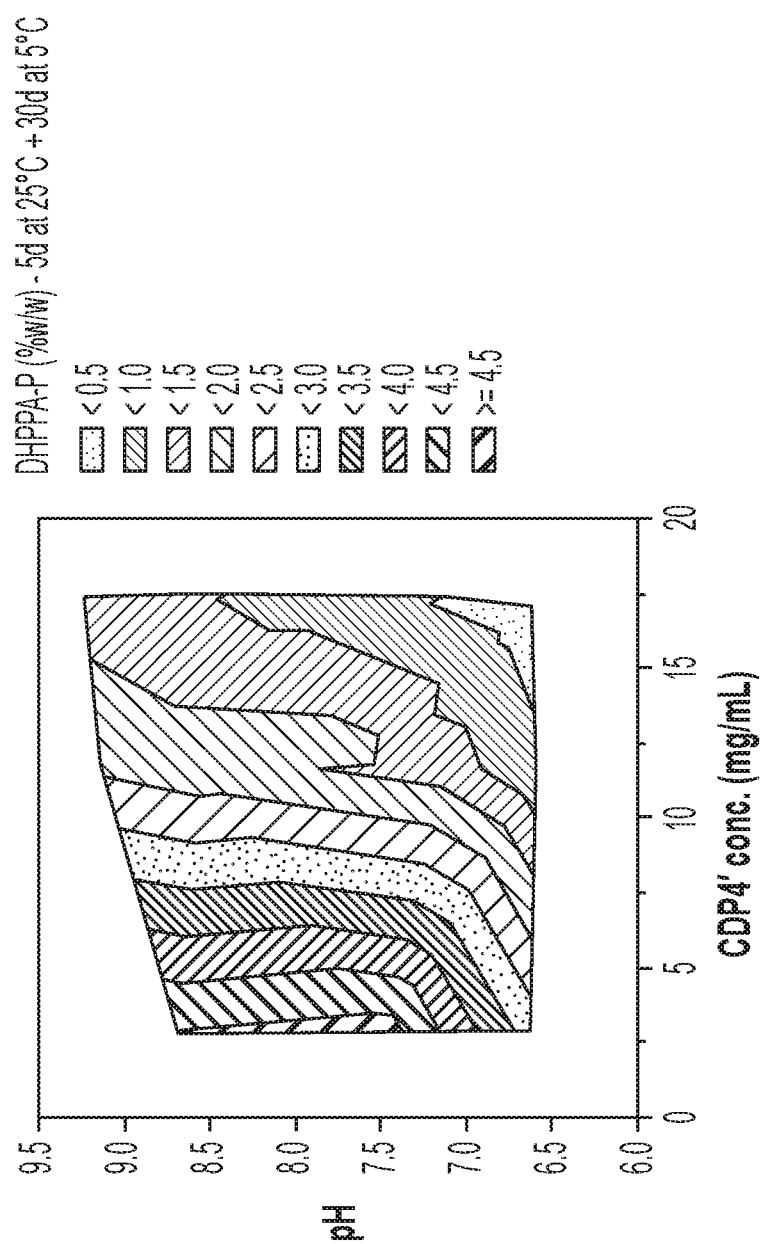
FIG. 8 is a graphical representation of DHPPA-P levels (% w/w) relative to carbidopa 4'-monophosphate concentration by pH after 5 days at 25° C. plus 30 days at 5° C. where % w/w is the amount of DHPPA-P relative to the amount of carbidopa 4'-monophosphate times 100.

The results shown in Table 4-7 were plotted as contour plots as shown in FIGS. 8-11. FIG. 8 is a graphical representation of DHPPA-P levels (% w/w) relative to carbidopa 4'-monophosphate amount by pH after 5 days at 25° C. plus 30 days at 5° C.

Figure 9:
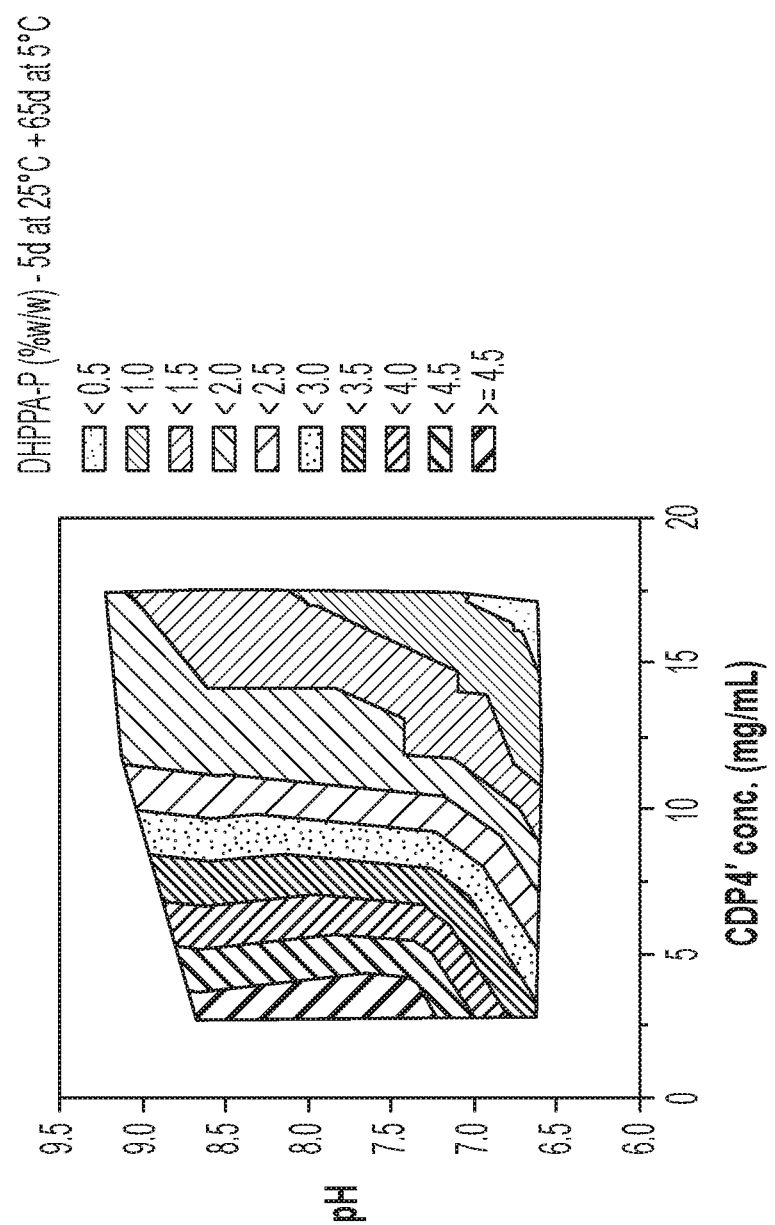
FIG. 9 is a graphical representation of DHPPA-P levels (% w/w) relative to carbidopa 4'-monophosphate concentration by pH after 5 days at 25° C. followed by 65 days at 5° C. where % w/w is the amount of hydrazine per amount of carbidopa 4'-monophosphate times 100.

FIG. 9 is a graphical representation of DHPPA-P levels (% w/w) relative to carbidopa 4'-monophosphate amount by pH after 5 days at 25° C. plus 65 days at 5° C.

Figure 10:
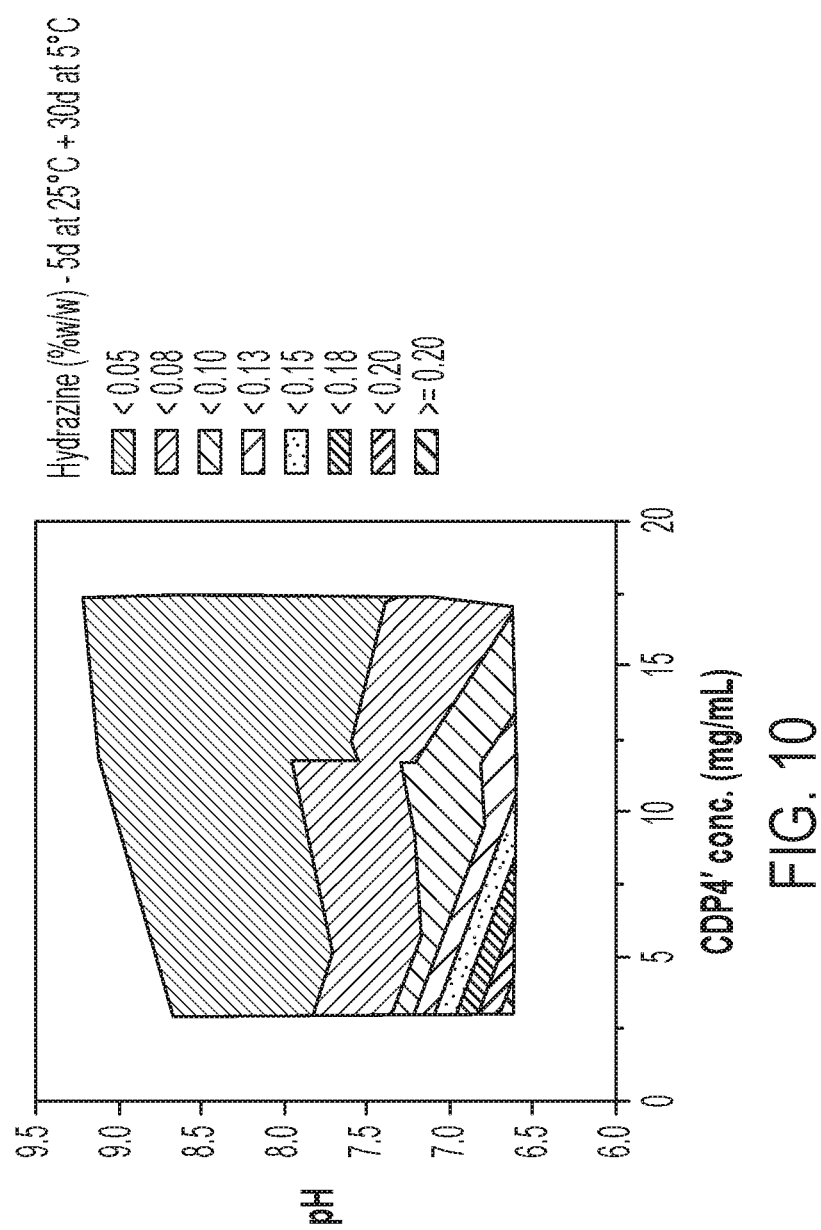
FIG. 10 is a graphical representation of hydrazine levels (% w/w) relative to carbidopa 4'-monophosphate concentration by pH after 5 days at 25° C. followed by 30 days at 5° C.

FIG. 10 is a graphical representation of hydrazine levels (% w/w) relative to carbidopa 4'-monophosphate amount by pH after 5 days at 25° C. followed by 30 days at 5° C.

Figure 11:
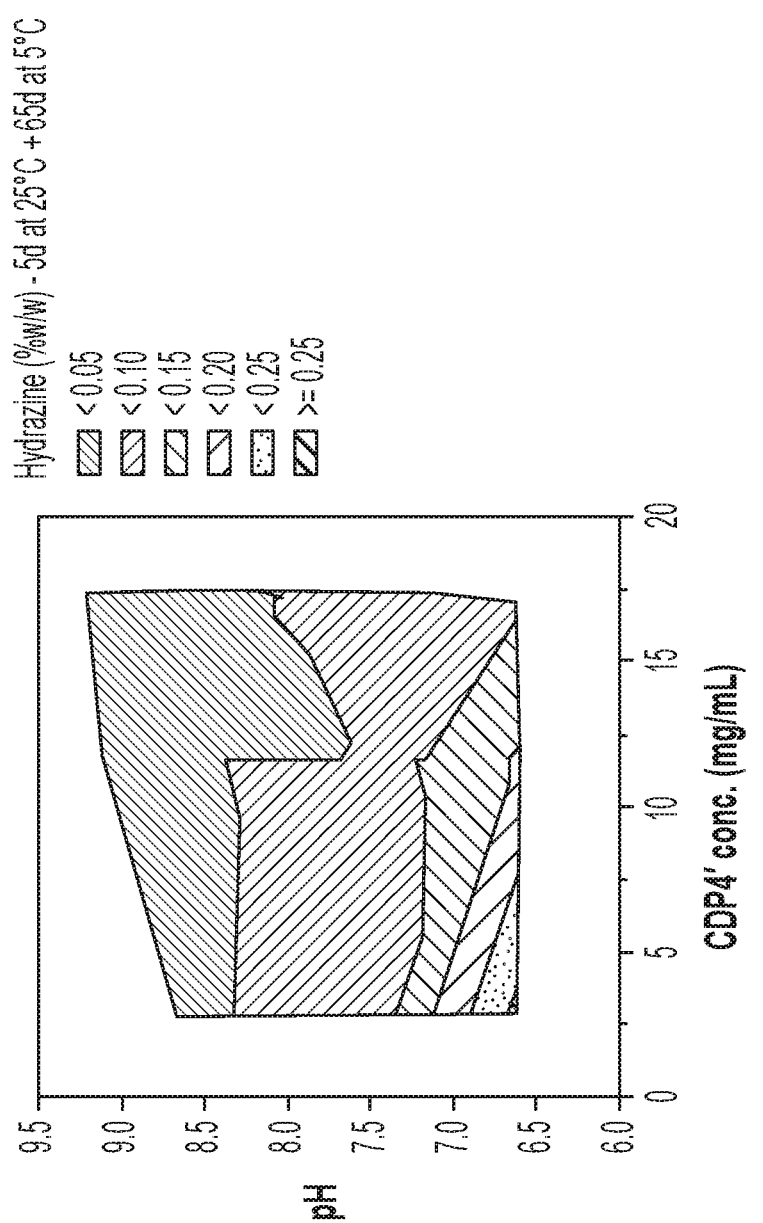
FIG. 11 is a graphical representation of hydrazine levels (% w/w) relative to carbidopa 4'-monophosphate concentration by pH after 5 days at 25° C. followed by 65 days at 5° C.

FIG. 11 is a graphical representation of hydrazine levels (% w/w) relative to carbidopa 4'-monophosphate amount by pH after 5 days at 25° C. followed by 65 days at 5° C.

As shown in FIGS. 8 and 9, at higher concentrations of carbidopa 4'-monophosphate and lower pH, the DHPPA-P levels are lower.

As shown in FIGS. 10 and 11, hydrazine levels are lower at higher pH values. Formulations having a concentration of about 240 mg/mL of levodopa 4'-monophosphate and 12 mg/mL of carbidopa 4'-monophosphate (about 170 mg levodopa by molecular weight) at final pH values between about 6.5 and 9.0 showed low levels of DHPPA-P and hydrazine.

Example 3

Continuous Subcutaneous Infusion of Levodopa and Carbidopa Prodrugs in Healthy Volunteers for 24 hours: Safety and Tolerability over 10 days to Simulate 1 year of Exposure This study was designed to assess the safety and local tolerability of 24 hour continuous subcutaneous infusion of an aqueous pharmaceutical composition comprising levodopa 4'-monophosphate prodrug corresponding in structure to formula (A-1) and carbidopa 4'-monophosphate prodrug corresponding in structure to formula (B-1) (the prodrug combination). The study simulated one-year of exposure by administering the pharmaceutical composition for 10 consecutive days in a confined area of the abdomen of healthy volunteers.

Methodology

The study was a phase 1, randomized, placebo-controlled, study of healthy volunteers receiving the pharmaceutical composition sufficient to provide 600 mg of levodopa and an equal volume of saline via 24-hour continuous subcutaneous infusion for 10 days simultaneously on opposite sides of the abdomen. The study consisted of 3 periods as shown in Table 8.

TABLE 8

Study Design Schematic of Safety and Tolerability Study over 10 days to Simulate 1 year of Exposure

| Screening (28 days) | Confinement Period Co-administration of the Pharmaceutical Composition and Placebo | Follow-up (28 ± 3 days) |
|---|---|---|
| DAY −1 | ↓ ↓ ↓ ↓ ↓ ↓ ↓ ↓ ↓ ↓<br>1 2 3 4 5 6 7 8 9 10  11  12<br>↑ ↑ ↑ ↑ ↑ ↑ ↑ ↑ ↑ ↑ | |

Middle row DAY indicates required confinement or clinical visit
Top and bottom row boxes indicate day with blinded infusion site evaluation
↓ 24-hour subcutaneous infusion of placebo to infusion site
↑ 24-hour subcutaneous infusion of the pharmaceutical composition to infusion site As shown in Table 8, the screening period lasted for 28 days and was conducted to ensure patients met eligibility and criteria and also to collect medical history and baseline clinical assessments. The next period was a confinement period during which patients were confined to the study site for 13 days (Day −1 to Day 12). During the confinement period, the infusion was started at Day 1 where each patient was simultaneously administered the pharmaceutical composition and equal volumes of placebo (saline). This infusion was administered in two 5 cm diameter areas on opposite sides of the abdomen. Subjects and infusion site raters were blinded as to which treatment was administered on each side of the abdomen. Infusion sets were changed daily, and the catheter of each infusion set was placed within a 5-cm diameter area of the site used on the previous day. Infusion was continuous for 24 hours/day over a 10 days period in which subjects received a levodopa equivalent dose of about 600 to about 700 mg/day. Next, the follow up period of 28 days was conducted to allow ad hoc reporting of any adverse events. Infusion sets were changed and reapplied daily on the same skin surface.

Infusion Site Rotation

Good clinical practice and anecdotal data recommended rotating injection sites regularly, keeping them at least 2.5 cm apart, to reduce risk of infection or irritation, fatty tissue build up (hypertrophy) and scar formation (fibrosis). The infusion set selected for this study (Smith Cleo 90) recommended changing the set every 3 days to preserve set sterility. In clinical practice, it is expected that patients will adopt a rotation scheme such as a clock that allows a rotation that allows using the same infusion site after 11 alternative sites have been used. Individuals adopt a rotation schedule for infusion sites around the navel (center). If rotation begins at the 12 o'clock position and proceeds clockwise, assuming that each infusion site is used of 3 days, patients will return to the infusion site at the 12 o'clock position after approximately 36 days—(12*3=) 36 days, with an average use of the same site of infusion 10 times/year. This study provided an accelerated simulation of longer-term use for assessment of local tolerability in healthy human volunteers for the number of repeat infusion sites that a patient would use over the course of a year.

Population

The key inclusion criteria for the study were:
Adult male or female healthy human volunteers 45 to 75 years of age;
Body Mass Index (BMI) from 18.0 kg/m2 to 32.0 kg/m2, inclusive;
A condition of general good health, based upon medical history, physical examination, and no clinically significant laboratory values, Electrocardiogram (ECG), or vital parameters; and
No history of significant skin conditions or disorders the study investigator determines might interfere with study assessments.

Assessments and Analysis

Systemic and local safety and tolerability were assessed daily. Notable skin reactions were defined a priori as events normally not associated with predictable reactions from the use of infusion sets (grades or on the Infusion Site Evaluation Scales). Both subjects and raters were blinded to the sides of the abdomen in which the aqueous pharmaceutical composition comprising the levodopa 4'-monophosphate and carbidopa 4'-monophosphate, and placebo were infused. Specifically, the local skin tolerability of 24-hours continuous subcutaneous infusion of the pharmaceutical composition in the abdomen for 10 days in 33 healthy human volunteers who completed the 10-day dosing period was assessed. Local skin tolerability was assessed by a blinded rater using the Infusion Site Evaluation 2-part scale (Table 9). This evaluation included numeric grading (0-7) and letter grading (A-G) scales. Notable skin reactions were defined a-priori as events normally not associated with predictable reactions from the use of infusion sets (grades or The primary endpoint was the number of healthy human volunteers who had a notable skin reaction at the pharmaceutical composition infusion site on >2 days of the 10-day infusion. A 95% upper confidence bound for the proportion of the population who would have a notable skin reaction on >2 days of a 10-day infusion was obtained by the Clopper- Pearson method. For each infusion site evaluation scale, a one-sided sign test was performed to test the hypothesis of no difference between the pharmaceutical composition and placebo at the final evaluation against the alternative hypothesis that the pharmaceutical composition is more likely to have a higher grade.

TABLE 9

Infusion Site Assessment Grading Scales

| Grade | Description |
|---|---|
| | Numeric Grading (Part 1) |
| 0 | No evidence of irritation |
| 1 | Minimal erythema, barely perceptible |
| 2 | Moderate erythema, readily visible; or minimal edema; or minimal papular response |
| 3 | Erythema and papules |
| 4 | Definite erythema |
| 5 | Erythema, edema, and papules |
| 6 | Vesicular eruption |
| 7 | Strong reaction spreading beyond the test site |
| | Letter Grading (Part 2) |
| A | No finding |
| B | Slight glazed appearance |
| C | Marked glazing |
| D | Glazing with peeling and cracking |
| E | Glazing with fissures |
| F | Film of dried serous exudates covering all or portion of the patch site |
| G | Small petechial erosions and/or scabs |

Safety assessments included the following in addition to the infusion site evaluation: The percentage of subjects with treatment-emergent AEs and serious adverse events (SAEs); Change from baseline to end of study in clinical laboratory values, vital sign measurements, electrocardiograms (ECGs), and physical examination findings.

Results

The safety dataset included 34 subjects as presented in Table 10.

TABLE 10

Baseline demographics

| Characteristic | Safety Population (N = 34) |
|---|---|
| Gender, n (%) | |
| Female | 9 (26.5) |
| Male | 25 (73.5) |
| Ethnicity, n (%) | |
| Hispanic or Latino | 5 (14.7) |
| Not Hispanic or Latino | 29 (85.3) |
| Race, n (%) | |
| White | 24 (70.6) |
| Black or African American | 7 (20.6) |
| Multiple | 3 (8.8) |
| Age, years, | |
| mean (SD) | 56.1 (7.2) |
| range | 45-69 |
| Weight (kg), mean (SD) | 81.6 (10.1) |
| BMI (kg/m$^2$), mean (SD) | 27.0 (2.7) |

BMI = body mass index; SD = standard deviation.

Tolerability

Figure 12:
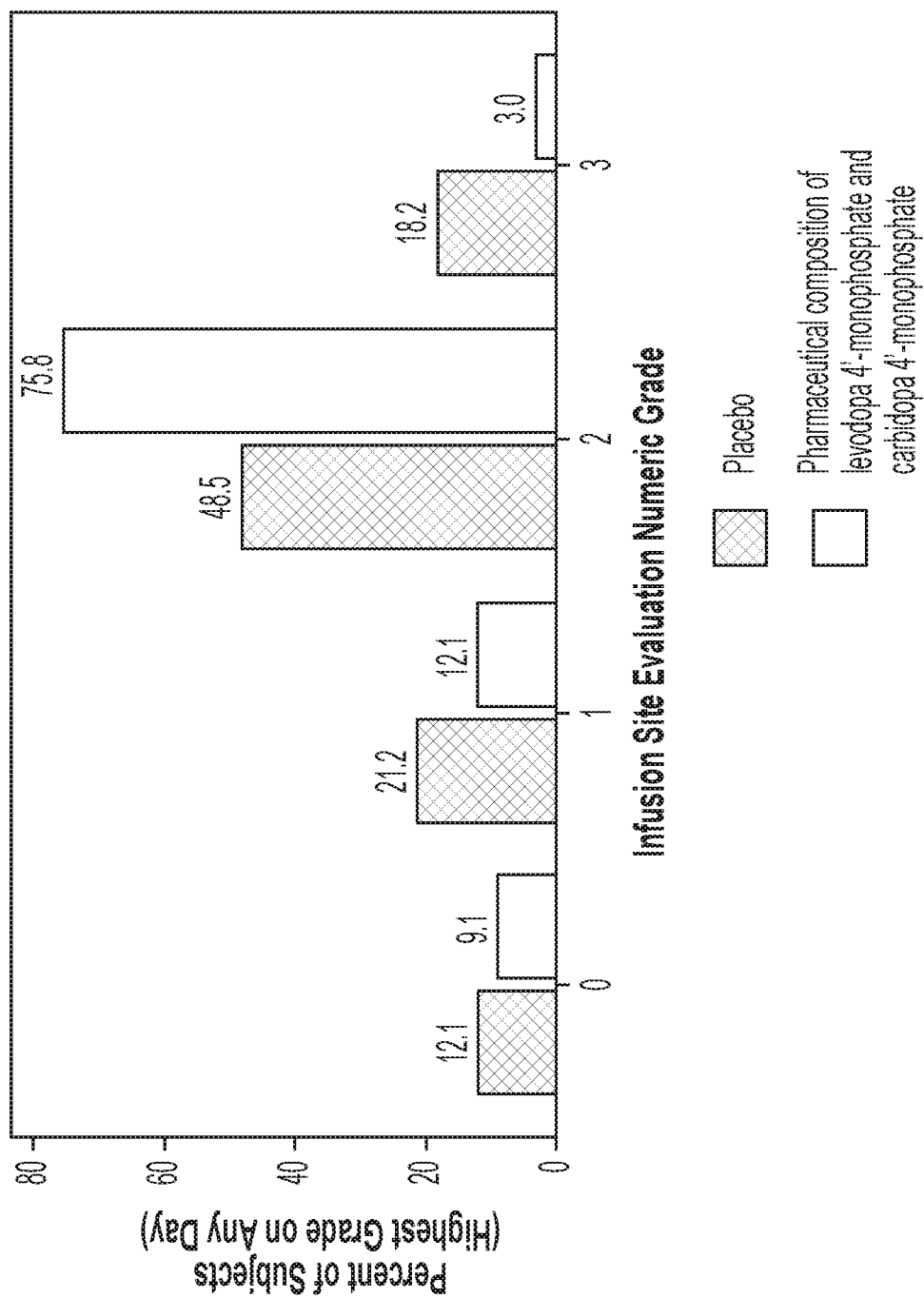
FIG. 12 is a graphical representation of the percentage of subjects by the highest grade received on any of the 10 Days for the pharmaceutical composition (levodopa 4'-monophosphate and carbidopa 4'-monophosphate at a 20:1 ratio) and placebo on the Infusion Site Evaluation Numeric Scale.
Figure 13:
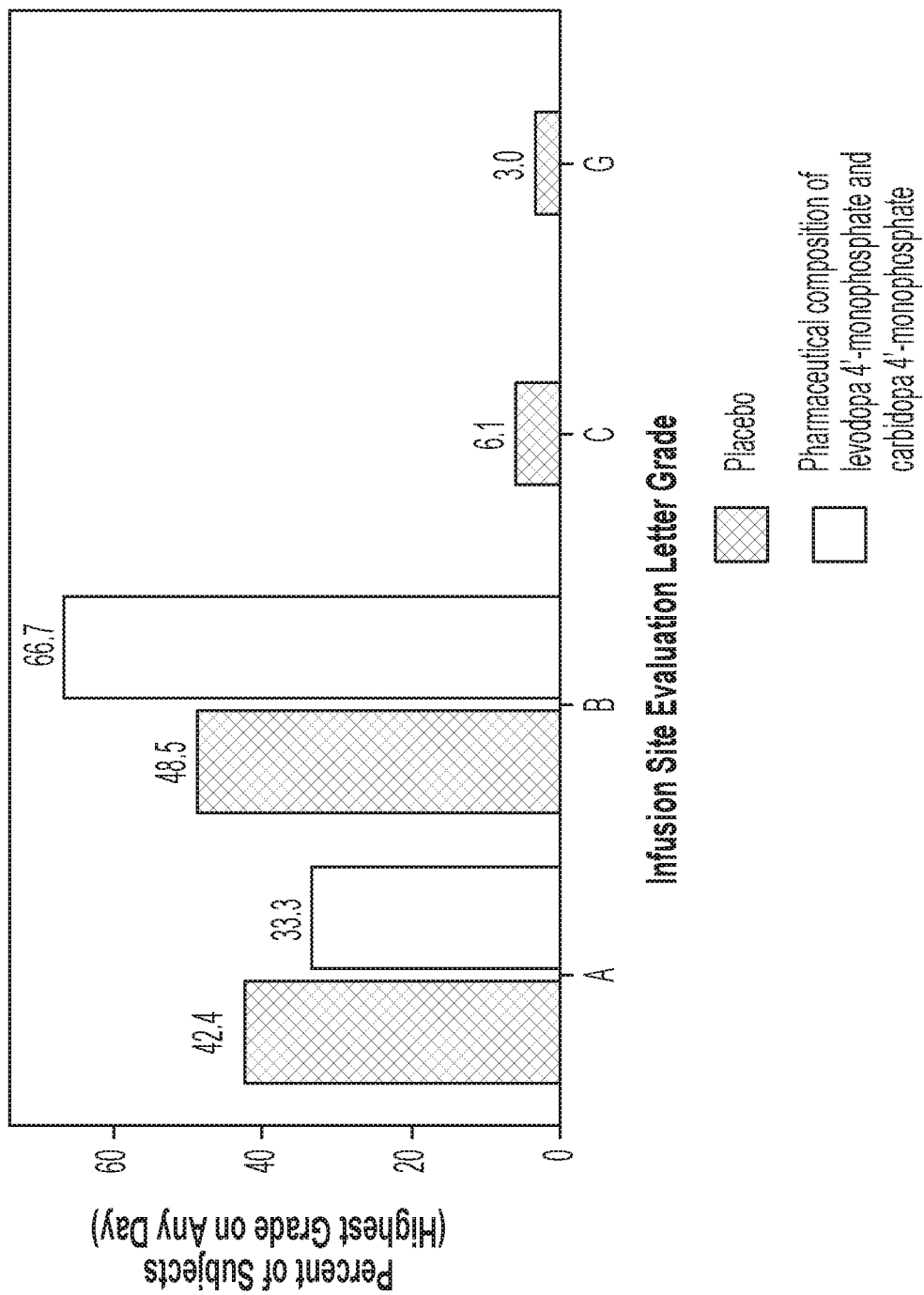
FIG. 13 is a graphical representation of the percentage of subjects by the highest grade received on any of the 10 Days for a pharmaceutical composition of levodopa 4'-monophosphate and carbidopa 4'-monophosphate at a 20:1 ratio and placebo on the Infusion Site Evaluation Letter Grade Scale.

The highest grade reported for each healthy human volunteer subject (the pharmaceutical composition vs placebo sites) from Day 1 to Day 10 of the study is summarized graphically for the respective infusion site assessment scales in FIG. 12 and FIG. 13. Out of the subjects who completed the 10-day dosing, the percent of subjects who reported notable skin reactions was 0% (0/33) at the pharmaceutical composition infusion site and 3.0% (1/33) at the placebo infusion site. The difference between the pharmaceutical composition and placebo with respect to dermatologic assessment on Day 10 of infusion was not statistically significant for the numeric (P=0.828) or letter (P=0.363) grading scales. The 95% upper confidence bound for the proportion of the population that would have a notable skin reaction on more than 2 days of a 10-day infusion of the pharmaceutical composition as administered in this study is 0.087 (8.7% of the population). The 95% upper confidence bound for the proportion of the population that would have a notable skin reaction on more than 2 days of a 10-day placebo infusion as administered in this study is also 0.087 (8.7% of the population).

Safety

There were no clinically significant laboratory values, vital signs, or ECG findings. Overall, 97% of subjects reported at least one adverse event (AE). There was one serious AE reported 4 days after study completion, which was considered not potentially related to study drug. There were no discontinuations due to an AE (Table 11). The most frequently reported adverse events were infusion site erythema (91%), infusion site reaction (44%), and infusion site pain (32%) (Table 12). All infusion site AEs were mild or moderate in severity and resolved quickly.

TABLE 11

Treatment- Emergent Adverse Events in Healthy Human Volunteer Subjects

| Subjects with Any Adverse Events | Overall N = 34 N (%) |
|---|---|
| Adverse Event | 33 (97.1) |
| AE with reasonable possibility of being drug-related | 17 (50.0) |
| Severe AE | 1 (2.9)* |
| Serious AE | 1 (2.9)* |
| AE leading to discontinuation of study drug | 0 |

*Musculoskeletal pain judged as not potentially related to study drug.
AE = adverse event

TABLE 12

Infusion Site Treatment-Emergent Adverse Events in Healthy Human Volunteer Subjects

| | Overall N = 34 n (%) | Prodrug Combination N = 34 n (%) | Placebo N = 34 n (%) |
|---|---|---|---|
| Infusion site AEs of interest | 31 (91.2) | 30 (88.2) | 30 (88.2) |
| Bruising | 4 (11.8) | 2 (5.9) | 2 (5.9) |
| Erosion | 1 (2.9) | 0 | 1 (2.9) |
| Erythema | 31 (91.2) | 28 (82.4) | 30 (88.2) |
| Hemorrhage | 1 (2.9) | 1 (2.9) | 1 (2.9) |
| Edema | 9 (26.5) | 9 (26.5) | 0 |
| Pain | 11 (32.4) | 11 (32.4) | 2 (5.9) |
| Reaction | 15 (44.1) | 14 (41.2) | 13 (38.2) |

The pharmaceutical composition comprising levodopa 4'-monophosphate prodrug corresponding in structure to formula (A-1) and carbidopa 4'-monophosphate prodrug corresponding in structure to formula (B-1) has the potential to provide the broad range of levodopa exposure required to adequately control motor symptoms and to be an alternative therapeutic option for Parkinson's disease patients. This study demonstrated that the pharmaceutical composition was generally well tolerated and did not cause notable skin reactions at low, yet clinically relevant, doses administered subcutaneously in a confined area of the abdomen continuously for 10 consecutive days.

Example 4

Design for a Phase 1b Study Evaluating the Safety and Tolerability of a 4-Week Continuous Subcutaneous Infusion of Levodopa and Carbidopa Prodrugs in Parkinson's Disease Patients.

This study was designed to evaluate the safety and tolerability of a 4-week continuous subcutaneous infusion of an aqueous pharmaceutical composition comprising levodopa 4'-monophosphate prodrug corresponding in structure to formula (A-1) and carbidopa 4'-monophosphate prodrug corresponding in structure to formula (B-1) in a w/w 20:1 ratio. In addition, the steady-state plasma levodopa levels achieved by the continuous subcutaneous infusion of the pharmaceutical composition were assessed and the exploratory efficacy were evaluated by the change from baseline in the endpoints listed in Table 18A.

Method

Figure 14A:
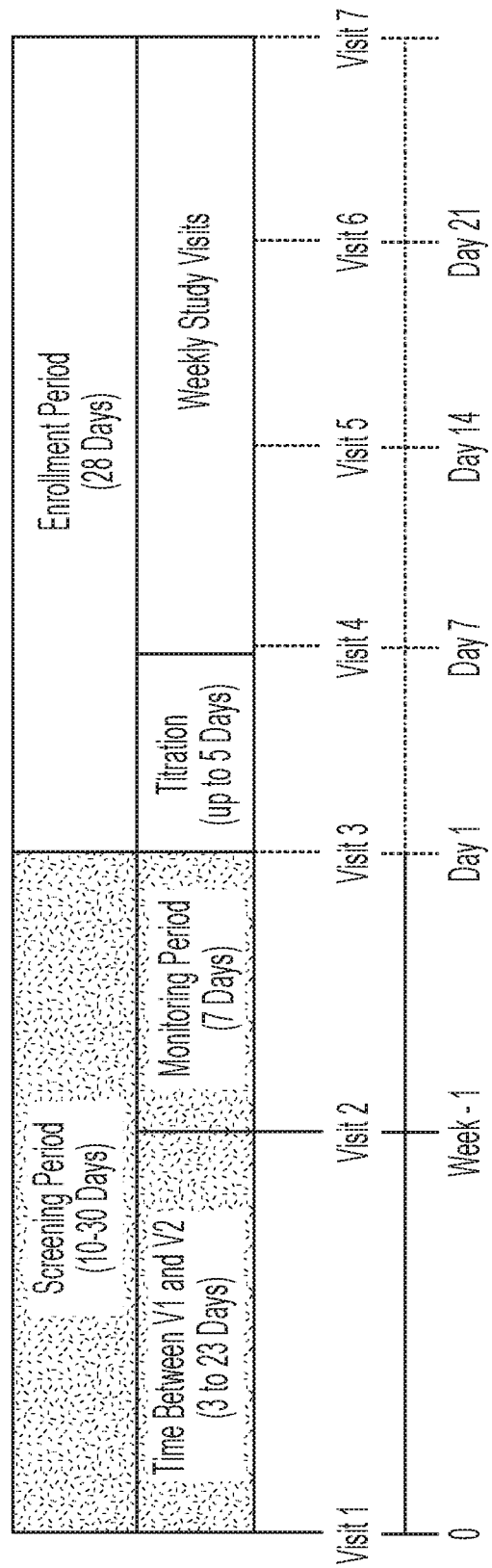
FIG. 14A is a graphical representation of the study design for Clinical Study A to evaluate the safety and tolerability of a 4-week continuous subcutaneous infusion of a pharmaceutical composition of levodopa 4'-monophosphate and carbidopa 4'-monophosphate at a 20:1 ratio in patients.

A single-arm, open-label, phase 1 b study of patients with Parkinson's disease treated with personalized therapeutic doses of the pharmaceutical composition via 24-hour continuous subcutaneous infusion for 28 days was designed. Patients were recruited from sites in the United States. The study consisted of 4 periods and is graphically represented in FIG. 14A. The Screening period included 2 visits including the monitoring period to establish eligibility and to confirm that the patient's current Parkinson's disease therapy has been stable for 30 days. The Screening Period also included a Monitoring period for the 7 days immediately following visit 2. Patients recorded Parkinson's disease medications using a subject dosing diary and monitored motor symptoms using a wearable device The titration period was part of the Enrollment Period and followed the Screening period. On day 1 of the titration period, patients received a bolus dose of the pharmaceutical composition followed by a continuous infusion at a constant rate, with subsequent dose adjustments at the investigator's discretion based on the patient's clinical response. The therapeutic dose is defined as the dose able to elicit an adequate control of motor symptoms by minimizing the number of "Off" episodes and maximizing the functional "On" time while minimizing troublesome dyskinesia. Patients continued receiving the therapeutic dose of the pharmaceutical composition established during the titration period until day 28—the Treatment period. The key inclusion criteria for the study are summarized in Table 13.

TABLE 13

Table 1. Key Inclusion and Exclusion Criteria in Patients

| Inclusion | Exclusion |
|---|---|
| Adult male or female patients 30 to 85 years of age with a clinical diagnosis of levodopa-responsive idiopathic Parkinson's disease | Previous exposure to the pharmaceutical composition |
| Patients whose symptoms are judged by the investigator to be inadequately controlled by current stable therapy | History of significant skin conditions or disorders the study investigator determines might interfere with study assessments |
| Have a recognizable/identifiable "Off" and "On" state | MMSE score < 24 |
| Have a minimum of 2.5 hours of "Off" time/day | Abnormal laboratory values, ECG, or vital parameters at screening |

ECG = electrocardiogram; MMSE = mini-mental state examination; PD = Parkinson's disease.

Systemic safety and tolerability were assessed by adverse event monitoring, laboratory values, vital signs, electrocardiogram, and safety scales, including the Columbia-Suicide Rating Scale. The infusion site grading scales (Table 14A) and the exploratory efficacy assessments (Table 14B) were used to assess the outcome of the study.

Subjects recorded Parkinsonian symptoms based on the questionnaire in the Parkinson's Disease Diary. Each subject recorded whether he/she was "On", "Off", or "Asleep" and the severity of his/her dyskinesias (troublesome or not troublesome). Statistical significance for change from baseline was shown at each visit for normalized "Off" time, normalized "On" time without dyskinesia, and normalized "On" time without troublesome dyskinesia. Statistical significance was not shown at any visit for normalized "On" time with non-troublesome dyskinesia and normalized "On" time with troublesome dyskinesia.

Evaluation of the subject MDS-UPDRS consisted of the following sections:
Part 1: Non-Motor Aspects of Experiences of Daily Living (nM-EDL)
Part 2: Motor Aspects of Experiences of Daily Living (M-EDL)
Part 3: Motor Examination (including Hoehn and Yahr stage)
Part 4: Motor Complications The MDS-UPDRS Total Score ranges from 0 to 176, with 176 representing the worst (total) disability and 0 as no disability. Mean Total Baseline Scores ranged from approximately 45 to 47 for all visits and Mean Visit Total Scores ranged from approximately 34 to 45 for all visits. Statistically significant changes from baseline were shown on Day 7, Day 28, and Final Visit for Total Score, Part 1 Score, and Part 2 Score, and on Day 28 and Final Visit for Part 4 Score. There was no statistically significant change at any visit for Part 3 "On" Score.

The PDQ-39 measured aspects of health that are relevant to subjects with Parkinson's Disease. Each item was scored on the following 5-point scale: 0=never, 1=occasionally, 2=sometimes, 3=often, 4=always (or cannot do at all, when applicable). Higher scores are consistently associated with more severe symptoms of the disease such as tremors and stiffness. The majority of subjects responded with "never" or "occasionally", while seven subjects responded with "always" or "cannot do at all." The results are presented as a summary index. The PDQ-39 summary index ranged from 0 to 100 where lower scores indicated a better perceived health status. The domains and indices used for evaluation are as follows:

Summary Index
Mobility Domain Score
Activities of Daily Living Domain
Emotional Well-being Domain Score
Stigma Domain Score
Social Support Domain Score
Cognition Domain Score
Communication Domain Score
Bodily Discomfort Domain Score Statistically significant changes from baseline were shown for all visits for Summary Index.

The PDSS-2 scale characterizes the various aspects of nocturnal sleep problems in subjects with Parkinson's disease. The PDSS-2 consisted of 15 questions that evaluated motor and non-motor symptoms at night and upon wakening, as well as disturbed sleep grouped into 3 domains: motor symptoms at night, PD symptoms at night, and disturbed sleep. Scores were calculated for each domain as well as a total score. The frequency was assessed for the sleep problems based on a 5-point Likert-type scale ranging from 0 (never) to 4 (very often). The majority of subjects responded with "never" or "occasionally", while seven subjects responded with "always" or "cannot do at all."

The KPPS assessed pain among subjects with Parkinson's disease. The scale measured the frequency and severity of seven domains of pain: musculoskeletal, chronic, fluctuation related, nocturnal, orofacial, local limb pain/edema/swelling, and radicular pain. The Total Score was also assessed. Statistically significant changes from baseline were shown for the Total Score on Day 28 and at the Final Visit, and for Fluctuated Related Pain Score on Day 28.

The PAS measured the severity of anxiety in subjects with Parkinson's disease. Scores for persistent anxiety, episodic anxiety, and avoidance behavior, as well as Total Score were assessed. Statistically significant changes from baseline were shown for Day 28 and Final Visit for Total Score and Avoidance Behavior.

All subjects wore a Kinesia 360 device that continuously recorded data for the assessment of tremor, dyskinesia, and mobility. There was no statistically significant change from baseline at any visit for tremor, dyskinesia, and slowness.

Infusion site assessment grading scales and exploratory efficacy assessments conducted and shown in Tables 14A and 14B below.

TABLE 14A

Infusion Site Assessment Grading Scales

| Grade | Description |
|---|---|
| | Numeric Grading (Part 1) |
| 0 | No evidence of irritation |
| 1 | Minimal erythema, barely perceptible |
| 2 | Moderate erythema, readily visible; or minimal edema; or minimal papular response |
| 3 | Erythema and papules |
| 4 | Definite erythema |
| 5 | Erythema, edema, and papules |
| 6 | Vesicular eruption |
| 7 | Strong reaction spreading beyond the test site |
| | Letter Grading (Part 2) |
| A | No finding |
| B | Slight glazed appearance |
| C | Marked glazing |
| D | Glazing with peeling and cracking |
| E | Glazing with fissures |

TABLE 14A-continued

Infusion Site Assessment Grading Scales

| Grade | Description |
|---|---|
| F | Film of dried serious exudates covering all or portion of the patch side |
| G | Small petechial erosions and/or scabs |

TABLE 14B

Exploratory Efficacy Assessments

| Endpoint | Assessment |
|---|---|
| Average daily "Off" and "On" times | Parkinson's Disease diaries |
| Parkinson's Disease symptoms | Movement Disorder Society-Unified Parkinson's Disease Rating Scale (UPDRS) |
| Motor symptoms | Kinesia 360 wearable device |
| Sleep symptoms | Parkinson's Disease Sleep Scale-2 (PDSS-2) |
| Quality of life | Parkinson's Disease Questionnaire-39 item (PDQ-39) |
| Anxiety symptoms | Parkinson's Anxiety Scale (PAS) |
| Pain symptoms | King's Parkinson's Disease Pain Scale (KPPS) |

Exploratory analyses were conducted to assess the efficacy of the pharmaceutical composition on Parkinson's disease symptoms in reducing "Off" time as well as motor and non-motor symptoms.

Results

Twenty-one patients were enrolled. The study population was primarily male (61.9%) and White (100%); 1 (4.8%) subject was Hispanic or Latino. Mean (SD) age was 61.6 (10.3) years. The mean (SD) Parkinson's disease duration since diagnosis was 9.0 (4.0) years and the mean (SD) duration of motor fluctuation was 6.0 (4.1) years. The average "Off" time/day at baseline was 6.54 hours, ranging from 3.77 to 9.46 hours. Seven subjects (33%) prematurely discontinued. Two subjects discontinued due to adverse events.

Baseline demographics and disease characteristics of the subjects are shown in Table 15.

TABLE 15

Baseline Demographics and Disease Characteristics in Patients

| | | Overall N = 21 |
|---|---|---|
| Gender, n (%) | Female | 8 (38) |
| | Male | 13 (62) |
| Race, n (%) | White | 21 (100) |
| Age, years, mean (SD) | | 61.6 (10.3) |
| Parkinson's Disease duration, year, n (%) | <10 years | 12 (57.1) |
| | ≥10 years | 9 (42.9) |
| Age at onset of Parkinson's Disease, years, mean (SD) | | 52.0 (10.6) |
| Time since onset of Parkinson's Disease, years, mean (SD) | | 10.1 (4.0) |
| Age at Parkinson's Disease diagnosis, years, mean (SD) | | 53.2 (10.9) |
| Time since Parkinson's Disease diagnosis, years, mean (SD) | | 9.0 (4.0) |
| Age at onset of motor fluctuations, years, mean (SD) | | 56.2 (10.5) |
| Time since onset of motor fluctuations, years, mean (SD) | | 6.0 (4.1) |
| MMSE total score* mean (SD) | | 28.8 (1.4) |

*Patient must have an MMSE score ≥24 for inclusion in the study.
MMSE = Mini-Mental State Examination; SD = standard deviation.

Figure 14B:
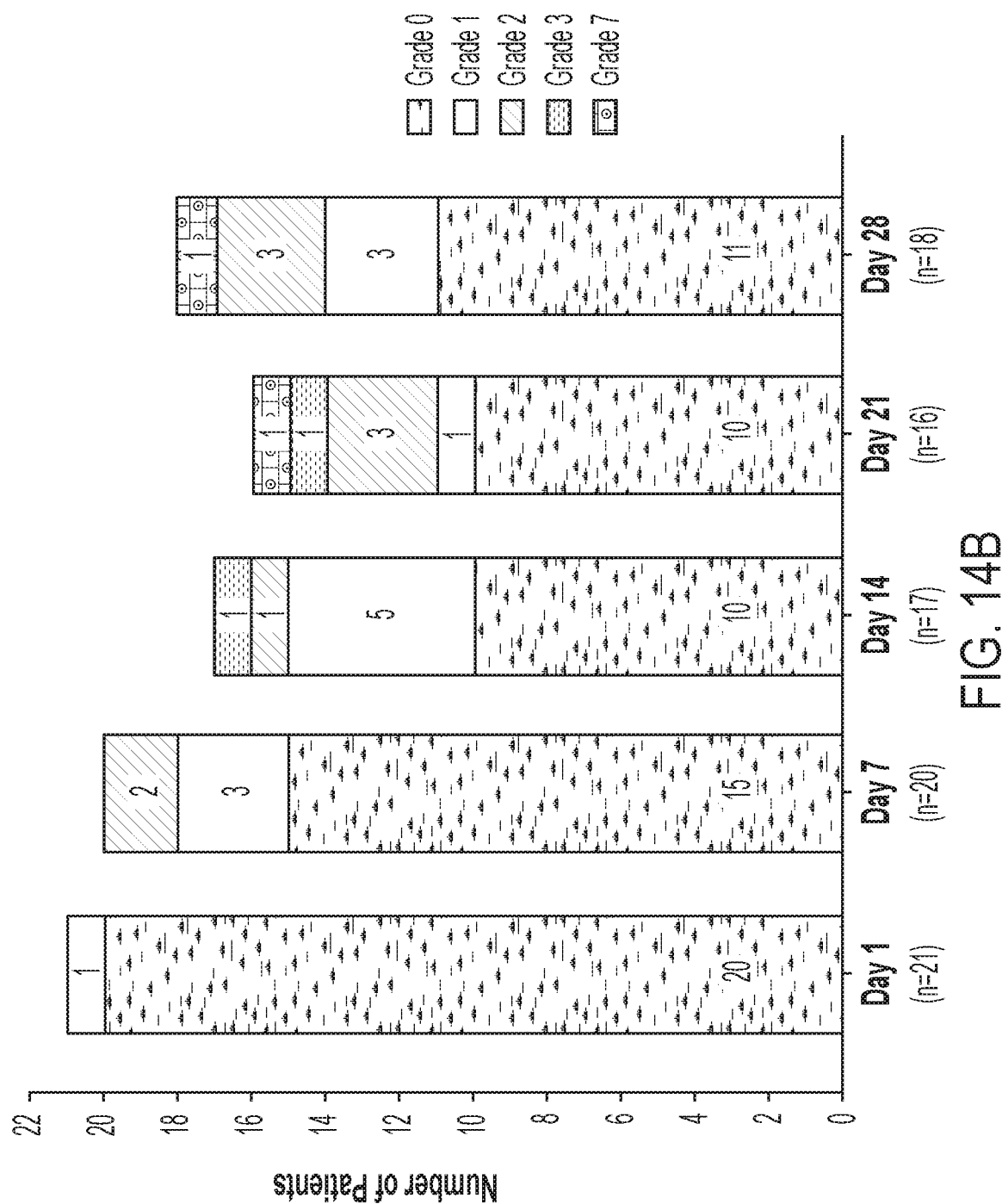
FIG. 14B is a graph showing the results for Clinical Study A of the infusion site grading using the numeric scale in patients.
Figure 14C:
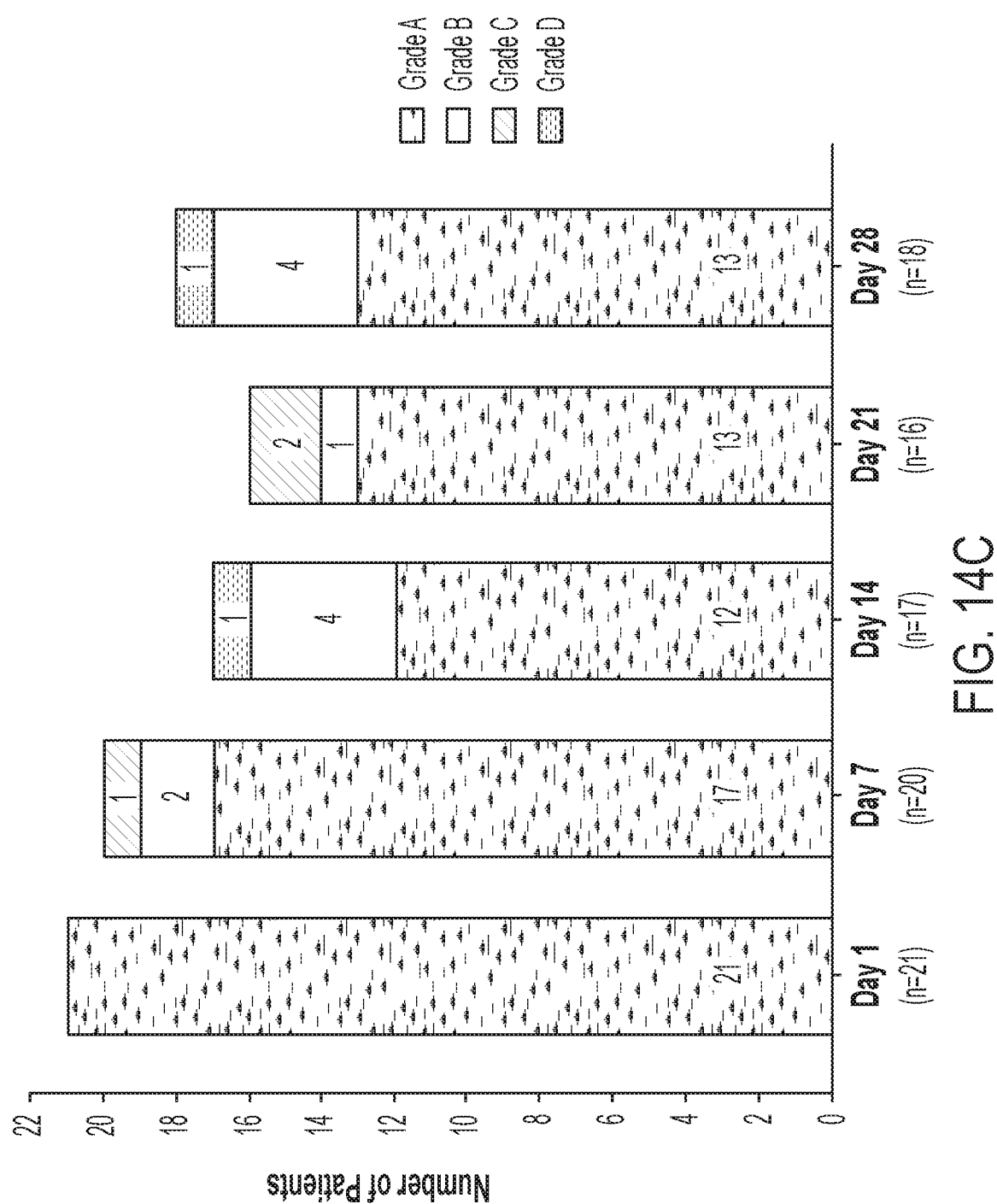
FIG. 14C is a graph showing the results for Clinical Study A of the infusion site grading using the letter scale in patients.

The results of the infusion site grading are shown in FIGS. 14B and 14C and Table 16, below.

TABLE 16

Infusion Site Treatment-Emergent Adverse Events (AEs) in Patients

| | Mild n (%) | Moderate n (%) | Severe (n %) | Total n (%) |
|---|---|---|---|---|
| Infusion site AEs of interest | 12 (57.1%) | 1 (4.8%) | 1 (4.8%) | 14 (66.7%) |
| Discomfort | 1 (4.8%) | 0 | 0 | 1 (4.8%) |
| Erythema | 5 (23.8%) | 1 (4.8%) | 0 | 6 (28.6%) |
| Irritation | 2 (9.5%) | 1 (4.8%) | 0 | 3 (14.3%) |
| Nodule | 2 (9.5%) | 0 | 0 | 2 (9.5%) |
| Pain | 6 (28.6%) | 1 (4.8%) | 0 | 7 (33.3%) |
| Pallor | 1 (4.8%) | 0 | 0 | 1 (4.8%) |
| Papule | 0 | 1 (4.8%) | 0 | 1 (4.8%) |
| Rash | 1 (4.8%) | 0 | 0 | 1 (4.8%) |
| Reaction | 0 | 0 | 1 (4.8%) | 1 (4.8%) |
| Warmth | 0 | 1 (4.8%) | 0 | 1 (4.8%) |

Table depicts the most severe AE for each preferred term as assessed for each patient; patients are counted once in each row; therefore, the sum is greater than the total in each column.
AE = adverse event.

In Parkinson's disease "Off"-time refers to periods of the day when the medications are not working well, causing reappearance or worsening of parkinsonian symptoms (tremor, rigidity, bradykinesia, as well as non-motor symptoms such as depression, pain, anxiety). In contrast, the term "on"-time refers to periods of adequate control of symptoms. "Off"-time can sometimes occur predictably and gradually ("wearing off"), or it may emerge suddenly and unexpectedly ("sudden Off", "yo-yo episodes"). The frequency and timing of wearing-off periods and the number of hours in "Off" time significantly correlate with a worsening in quality of life for Parkinson's patients.

Quality of life in Parkinson's disease can be assessed using tools and questionnaires, such as the Parkinson's Disease Questionnaire—39 items (PDQ-39), a self-report questionnaire which assesses the impact of Parkinson's disease on specific dimensions of functioning and well-being, and the PDSS-2, a revised version of the Parkinson's Disease Sleep Scale, designed to characterize and quantify the various aspects of nocturnal sleep problems in Parkinson's disease. The disease severity was instead evaluated via the Unified Parkinson's Disease Rating Scale (UPDRS) or via the Movement Disorders Society revised version (MDS-UPDRS), a tool comprised of a rater-based interview and clinical assessment designed to provide a quantifiable score for longitudinal assessment and follow-up of the disease.

Figure 14D:
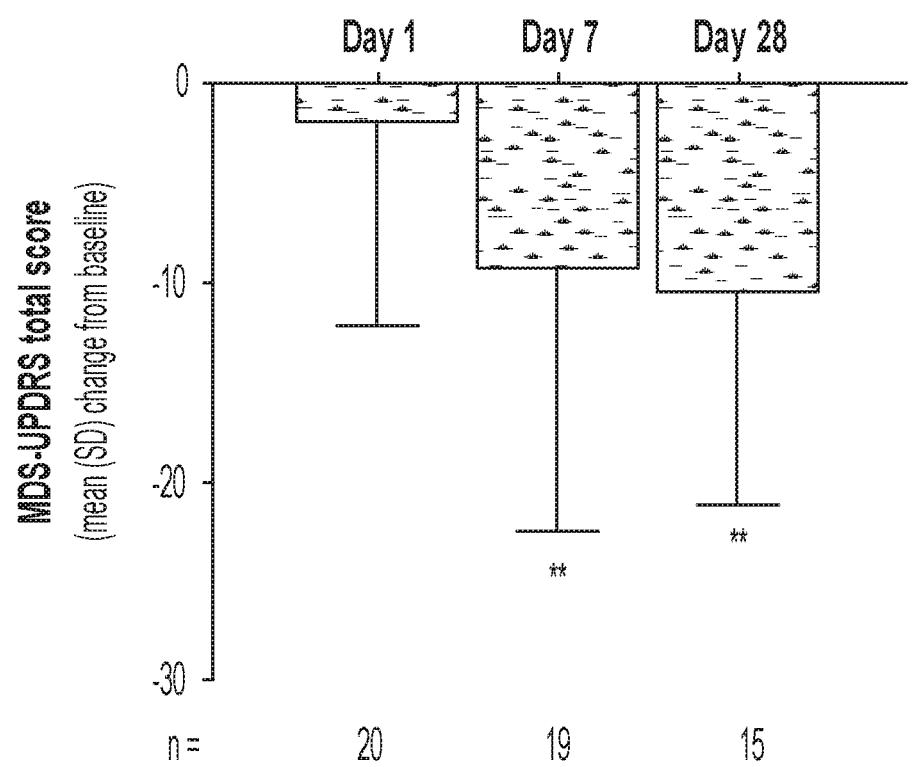
FIG. 14D is a graph showing Mean (SD) Change from Baseline in MDS-UPDRS Total Scores for Clinical Study A in patients.
Figure 14E:
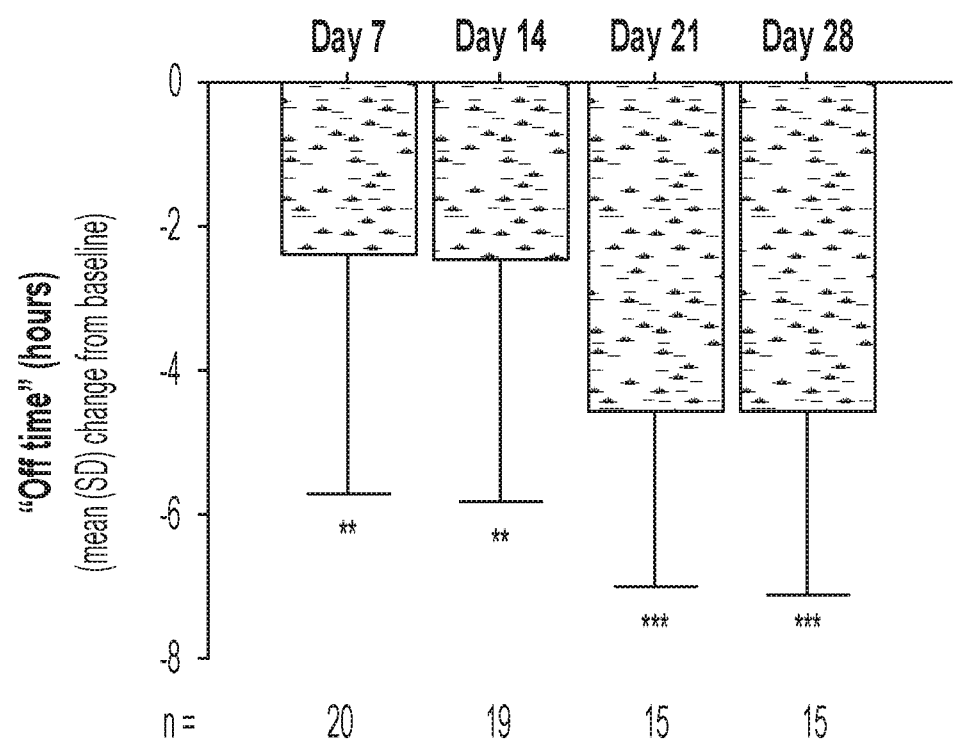
FIG. 14E is a graph showing Mean (SD) Change from Baseline in "Off" time at Regularly Scheduled Visits for Clinical Study A in patients.

Patient changes from baseline normalized "Off" time were measured as shown in Table 17 and shown in FIG. 14E. A summary of pre-specified efficacy endpoints is provided in Table 18A and efficacy assessments are shown in Table 18B.

TABLE 17

Patient changes from baseline normalized "Off" time

| Subject | Average Normalized "Off" Time (hours) at; Baseline[a] | Average Normalized "Off" Time (hours) at End of Study[b] | Improvement (hours) | Percent Improvement |
|---|---|---|---|---|
| 17-1 | 6.51 | 2.64 | 3.87 | 59.40 |
| 17-2 | 7.25 | 4.63 | 2.62 | 36.17 |
| 17-3 | 4.77 | 0.18 | 4.59 | 96.27 |
| 17-4[c,e] | 4.87 | 11.22 | −6.36[d] | −130.64[d] |
| 17-5 | 4.85 | 5.01 | −0.17[d] | −3.41[d] |
| 17-6 | 8.89 | 0.37 | 8.51 | 95.79 |
| 17-7 | 9.46 | 0.60 | 8.86 | 93.70 |
| 17-8[c] | 8.67 | 8.01 | 0.66 | 7.60 |
| 17-9[c] | 7.93 | 4.00 | 3.93 | 49.59 |
| 17-10[c,f] | 5.80 | 9.41 | −3.61[d] | −62.25[d] |
| 17-11 | 7.33 | 2.51 | 4.82 | 65.79 |
| 17-12 | 6.91 | 1.19 | 5.72 | 82.77 |
| 17-13[c] | 5.96 | 4.29 | 1.67 | 27.98 |
| 17-14 | 8.80 | 1.45 | 7.35 | 83.48 |
| 17-15 | 6.18 | 2.47 | 3.71 | 60.07 |
| 17.16 | 6.37 | 3.62 | 2.75 | 43.15 |
| 17-17 | 3.99 | 0 | 3.99 | 100 |
| 17-18 | 3.77 | 1.16 | 2.61 | 69.18 |
| 17-19 | 5.76 | 0.59 | 5.16 | 89.71 |
| 17-20[c] | 6.81 | 2.80 | 4.02 | 58.95 |
| Average | 6.54 | 3.31 | 3.24 | 46.17 |

[a]Average baseline "Off" time is calculated as the average "Off" time from Days −3 through Day −1.
[b]Average "Off" time at the end of the study is calculated as the average "Off" time prior to the last dose of study drug.
[c]Prematurely discontinued study drug.
[d]Worsening in normalized "Off" time.
[e]Subject not compliant with infusion set procedures.
[f]Subject discontinued the study drug but agreed to complete study visits.

TABLE 18A

Pre-specified efficacy endpoints in Patients

| Parameters | N | Baseline Mean (SD) | Final Mean (SD) | Change from Baseline to Final Mean (SD) |
|---|---|---|---|---|
| Normalized "Off" time (hours/day) | 20 | 6.54 (1.65) | 3.31 (3.14) | −3.24 (3.65) |
| Normalized "On" time without troublesome dyskinesia[a] (hours/day) | 20 | 8.57 (2.24) | 11.86 (4.34) | 3.30 (4.11) |
| Normalized "On" time without dyskinesia (hours/day) | 20 | 5.82 (3.29) | 9.81 (5.90) | 3.99 (5.37) |
| Normalized "On" time with non-troublesome dyskinesia (hours/day) | 20 | 2.75 (3.18) | 2.06 (3.62) | −0.69 (3.77) |
| Normalized "On" time with troublesome dyskinesia (hours/day) | 20 | 0.89 (1.92) | 0.83 (2.69) | −0.06 (3.05) |
| MDS-UPDRS Total Score (Parts I-III) | 20 | 46.7 (18.73) | 37.7 (18.01) | −9.0 (11.87) |

TABLE 18A-continued

Pre-specified efficacy endpoints in Patients

| Parameters | N | Baseline Mean (SD) | Final Mean (SD) | Change from Baseline to Final Mean (SD) |
|---|---|---|---|---|
| PDQ-39 Summary Index | 20 | 23.2 (8.99) | 16.3 (9.16) | −6.9 (8.39) |
| PDSS-2 Total Score | 20 | 22.7 (14.25) | 20.7 (17.67) | −2.0 (11.48) |
| KPPS | 18 | 17.7 (21.20) | 11.7 (13.78) | −6.0 (9.82) |
| PAS | 18 | 11.0 (5.37) | 8.1 (4.54) | −2.9 (5.39) |
| Kinesia 360 Daily Tremor Score | 21 | 0.060 (0.0984) | 0.075 (0.1993) | 0.015 (0.1674) |
| Kinesia 360 Daily Dyskinesia Score | 21 | 0.709 (0.2652) | 0.682 (0.2845) | −0.027 (0.1932) |
| Kinesia 360 Daily Slowness Score | 17 | 1.438 (0.5213) | 1.442 (0.5392) | 0.004 (0.3392) |

TABLE 18B

Efficacy Assessments

| Assessment | Tool |
|---|---|
| Normalized "Off" and "On" time | PD Diaries |
| PD Symptoms | MDS-UPDRS Parts I-IV* |
| Sleep Symptoms | PDSS-2 |
| Quality of Life | PDQ-39 |
| Health-related Quality of Life | EQ-5D-5L |

*Or the UPDRS Parts I-V where a validated translation of the MDS-UPDRS is not available.
EQ-5D-5L = EuroQoL 5 dimensions questionnaire; MDS-UPDRS = Movement Disorder Society-Unified Parkinson's Disease Rating Scale; PD = Parkinson's disease; PDQ-39 = 39-item PD Questionnaire; PDSS-2 = PD Sleepiness Scale-2.

Analysis of efficacy data showed that 17 of the 20 patients had improvement in "Off" time. The mean (SD) reduction of "Off" time from baseline to study end was 3.24 (3.65) hours across subjects (46.2% improvement). Four subjects reported >90% reduction of daily "Off" time at the end of the study. There was mean reduction in normalized "Off" time, "On" time with non-troublesome dyskinesia, and "On" time with troublesome dyskinesia which resulted in a mean (SD) improvement in normalized "On" time without dyskinesia of 3.99 (5.37) hours. As shown in FIG. 14D, the mean (SD) reduction from baseline was 9.0 (11.87) for Movement Disorder Society-Unified Parkinson's Disease Rating Scale (MDS-UPDRS) total score, 6.9 (8.39) for Parkinson's Disease Questionnaire-39 items (PDQ-39) summary index, and 2.0 (11.48) for Parkinson's Disease Sleep Scale-2 (PDSS-2) total score. Following continuous subcutaneous infusion of the pharmaceutical composition, statistically significant changes from baseline were observed for: Parkinson's Disease "On" and "Off" times for dyskinesia, MDS-UPDRS Total Score, Non-Motor Aspects of Experiences of Daily Living, Motor Aspects of Experiences of Daily Living, and Motor Complications, and PDQ-39 Summary Index, and domains for Activities of Daily Living, Emotional Well-being, Cognition, Communication, Mobility, Stigma, and Bodily Discomfort.

Figure 21:
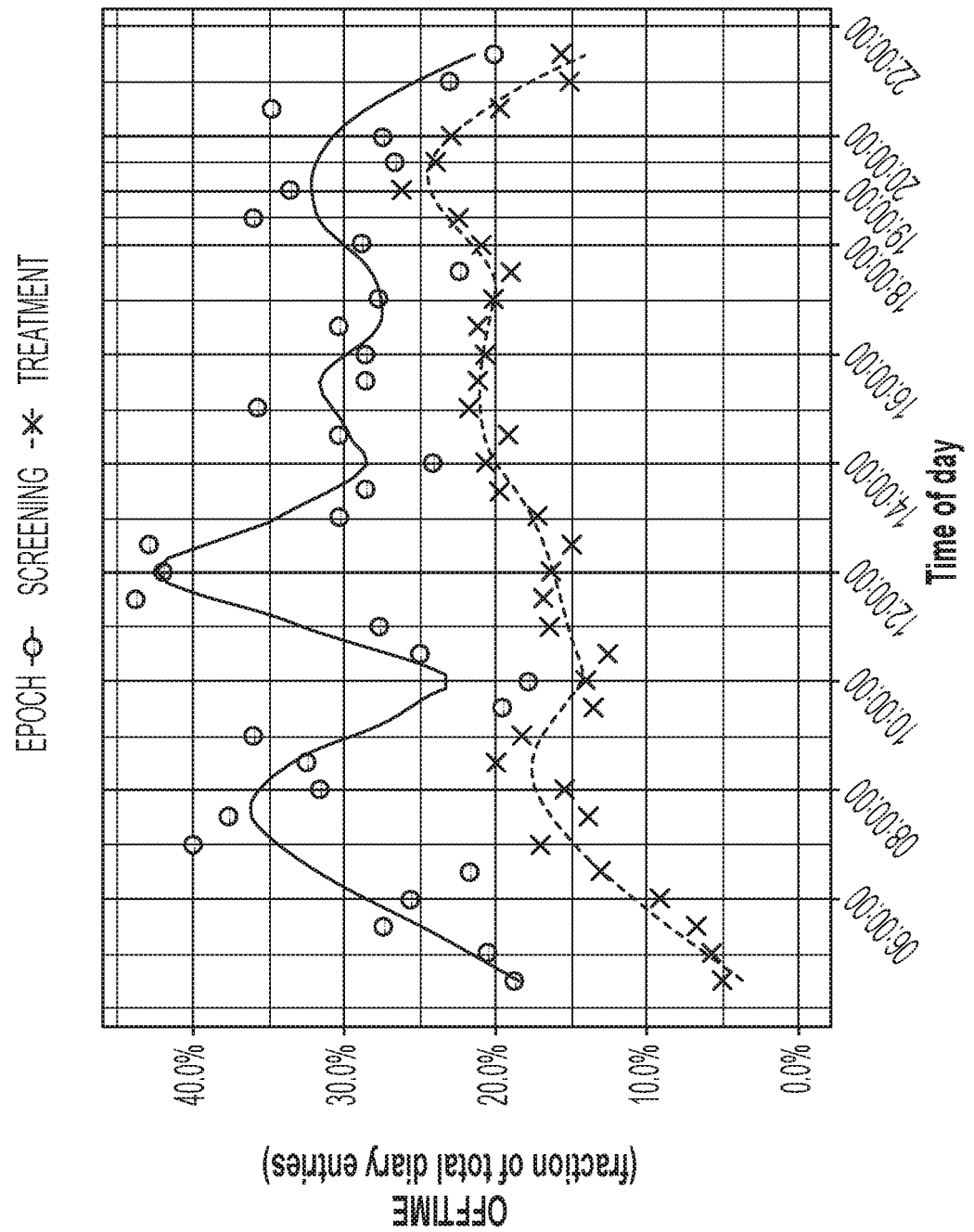
FIG. 21 shows the percent of patients experiencing "off" time during a day receiving the pharmaceutical composition compared with patients receiving oral Sinemet® (Clinical Study B).

FIG. 21 and Table 18C show the percent of patients experiencing "off" time receiving the pharmaceutical composition compared with patients receiving oral Sinemet®. As shown in FIG. 21, patients receiving oral Sinemet® treatment show undesirable spikes in "off" time in the morning and around meal times compared with patients receiving the CSCI pharmaceutical composition. Table 18C shows about 86.7% of the time the first morning symptom upon waking up was "Off" at baseline for patients receiving oral Sinemet®. Whereas, about 84.2% of the time the first morning symptom was "On" without dyskinesia at the end of the 28-day study for patients receiving the CSCI pharmaceutical composition.

TABLE 18C

Efficacy Assessments Early Morning First Non-Sleep Symptom in Parkinson's disease Diary

| Non-Sleep Symptom | | | OFF | | On Without Dyskinesia | | On With Non-Troublesome Dyskinesia | | On With Troublesome Dyskinesia | |
|---|---|---|---|---|---|---|---|---|---|---|
| Visit | Day* | N | n | (%) | n | (%) | n | (%) | n | (%) |
| Baseline | 1 | 20 | 18 | (90.0) | 1 | (5.0) | 0 | | 1 | (5.0) |
| | 2 | 20 | 18 | (90.0) | 1 | (5.0) | 0 | | 1 | (5.0) |
| | 3 | 20 | 16 | (80.0) | 4 | (20.0) | 0 | | 0 | |
| | Average # | | | 86.7 | | 10.0 | | | | 3.3 |
| Day 7 | 1 | 20 | 4 | (20.0) | 14 | (70.0) | 1 | (5.0) | 1 | (5.0) |
| | 2 | 17 | 2 | (11.8) | 10 | (58.8) | 5 | (29.4) | 0 | |
| | 3 | 18 | 5 | (27.8) | 8 | (44.4) | 5 | (27.8) | 0 | |
| | Average # | | | 19.9 | | 57.7 | | 20.7 | | 1.7 |
| Day 14 | 1 | 15 | 3 | (20.0) | 12 | (80.0) | 0 | | 0 | |
| | 2 | 15 | 3 | (20.0) | 10 | (66.7) | 2 | (13.3) | 0 | |
| | 3 | 16 | 3 | (18.8) | 13 | (81.3) | 0 | | 0 | |
| | Average # | | | 19.6 | | 76.0 | | 4.4 | | |
| Day 21 | 1 | 15 | 1 | (6.7) | 14 | (93.3) | 0 | | 0 | |
| | 2 | 15 | 1 | (6.7) | 14 | (93.3) | 0 | | 0 | |
| | 3 | 13 | 2 | (15.4) | 10 | (76.9) | 1 | (7.7) | 0 | |
| | Average # | | | 9.6 | | 87.8 | | 2.6 | | |

TABLE 18C-continued

Efficacy Assessments Early Morning First Non-Sleep Symptom in Parkinson's disease Diary

| Non-Sleep Symptom | | | OFF | | On Without Dyskinesia | | On With Non-Troublesome Dyskinesia | | On With Troublesome Dyskinesia | |
|---|---|---|---|---|---|---|---|---|---|---|
| Visit | Day* | N | n | (%) | n | (%) | n | (%) | n | (%) |
| Day 28 | 1 | 13 | 0 | | 12 | (92.) | 1 | (7.7) | 0 | |
| | 2 | 14 | 2 | (14.3) | 11 | (78.6) | 1 | (7.1) | 0 | |
| | 3 | 11 | 2 | (18.2) | 9 | (81.8) | 0 | | 0 | |
| | Average # | | | 10.8 | | 84.2 | | 4.9 | | |

Baseline is the last non-missing value prior to the beginning of the treatment period.
*Day is days prior to visit date. If Day is X, PD diary date is X day(s) prior to visit date, XX = 1, 2, 3.
: Average is the average percentage of 3 days.

Example 5

In order to facilitate physicians' determination of the most appropriate starting dose for the study described in Example 4, an algorithm to convert oral levodopa to the carbidopa 4'-monophosphate and levodopa 4'-monophosphate pharmaceutical composition was created. This algorithm takes into consideration the low variability and fluctuation of levodopa exposures when delivered continuously subcutaneously, the 24-hour exposure, the pharmacokinetic profile of levodopa from previous studies with the composition, and other clinical considerations.

Data from the patients who completed dosing were used in the evaluation of dose. All patients who completed the study (N=14) achieved desired dose range within 3 weeks after starting the pharmaceutical composition; 3 patients achieved desired a dose range on the same day after oral-to-the pharmaceutical composition conversion, 7 subjects required 1 week, 1 subject required 2 weeks, while the remaining 3 patients required 3 weeks. Adjustments at each time ranged from −0.04 mL/h to +0.08 mL/h (the equivalent of −136 mg levodopa/day to 273 mg levodopa/day) while the difference in infusion rates from Day 1 to Day 28 (all adjustments considered) ranged from −0.06 mL/h to +0.08 mL/h (the equivalent of −204 mg levodopa/day to +273 mg levodopa/day). Considering that at the time of enrollment all patient subjects were required to report motor fluctuations that were inadequately controlled by their best oral medications, these data suggest that the conversion algorithm is effective in guiding the starting dose of the pharmaceutical composition because the magnitude of change in the continuous infusion rate was considered small (within 20% for all but 1 subject) and the desired dose range was achieved within 3 weeks.

Levodopa dose levels by patient subject at the start and at the end of the study are provided in Table 19. The doses of the pharmaceutical composition delivered in a 24-hour treatment period ranged from approximately 28.8/576 mg to about 240/4800 mg of carbidopa 4'-monophosphate/levodopa 4'-monophosphate per day (equivalent to approximately 400 mg to 3400 mg of levodopa respectively, based on molecular weight). The average and median doses at study end were approximately 117.5/2350 mg and 96/1920 mg (equivalent to 1670 mg of and 1360 mg of levodopa, respectively, based on molecular weight).

TABLE 19

By-Patient Subject Listing of levodopa Dose Levels (mg/24 hours) at Study Start and Study End

| | Day 1 | | End of study | | |
|---|---|---|---|---|---|
| Subject | Levodopa 4'-monophosphate (mg/24 h) | Levodopa equivalents (mg/24 h) | Levodopa 4'-monophosphate (mg/24 h) | Levodopa equivalents (mg/24 h) | Difference between end of study and baseline (%) |
| 19-1 | 3936 | 2795 | 3648 | 2590 | −7.3 |
| 19-2 | 4800 | 3408 | 4800 | 3408 | 0.0 |
| 19-3 | 1536 | 1091 | 1824 | 1295 | 18.8 |
| 19-4[a] | 3840 | 2726 | 4032 | 2863 | 5.0 |
| 19-5 | 2112 | 1500 | 2304 | 1636 | 9.1 |
| 19-6 | 1920 | 1363 | 1920 | 1363 | 0.0 |
| 19-7[a] | 768 | 545 | 768 | 545 | 0.0 |
| 19-8 | 1152 | 818 | 1344 | 954 | 16.7 |
| 19-9[a] | 1248 | 886 | 1344 | 954 | 7.7 |
| 19-10[a] | 3264 | 2317 | 3264 | 2317 | 0.0 |
| 19-11[a] | 1344 | 954 | 1536 | 1091 | 14.3 |
| 19-12 | 1344 | 954 | 1536 | 1091 | 14.3 |
| 19-13 | 1728 | 1227 | 1728 | 1227 | 0.0 |
| 19-14[a] | 2880 | 2045 | 3072 | 2181 | 6.7 |
| 19-15 | 1152 | 818 | 1440 | 1022 | 25.0 |
| 19-16 | 2976 | 2113 | 3360 | 2386 | 12.9 |
| 19-17 | 576 | 409 | 768 | 545 | 33.3 |
| 19-18 | 2880 | 2045 | 2880 | 2045 | 0.0 |
| 19-19 | 3456 | 2454 | 3552 | 2522 | 2.8 |
| 19-20 | 3072 | 2181 | 3264 | 2317 | 6.3 |

[a]Prematurely discontinued study drug

As described, if a patient has a levodopa equivalent dose of 2000 mg prior to study entry, the recommended starting dose of the pharmaceutical composition of levodopa 4'-monophosphate prodrug corresponding in structure to formula (A-1) and carbidopa 4'-monophosphate prodrug corresponding in structure to formula (B-1) in a 20:1 w/w ratio is 4032 mg levodopa 4'-monophosphate delivered over 24 hours. As the levodopa dose for each patient is determined by individualized patient titration, patients in these studies start at doses of the pharmaceutical composition levodopa 4'-monophosphate prodrug corresponding in structure to formula (A-1) and carbidopa 4'-monophosphate prodrug corresponding in structure to formula (B-1), which are expected to result in exposure close to their previous regimen with the option of further dose modification to achieve optimal clinical response. In this manner, personalized, titratable dosing can be achieved across a dose range to address therapeutic needs.

Example 6

Pharmacokinetics of 24-hour Levodopa and Carbidopa Prodrugs Continuous Subcutaneous Infusion Treatment of Parkinson's Disease in Healthy Human Volunteers This study was designed to characterize the pharmacokinetics of aqueous pharmaceutical composition comprising a combination of levodopa 4'-monophosphate prodrug corresponding in structure to formula (A-1) and carbidopa 4'-monophosphate prodrug corresponding in structure to formula (B-1) (the prodrug combination) following continuous subcutaneous infusion to the abdomen.

Methods

Figure 15:
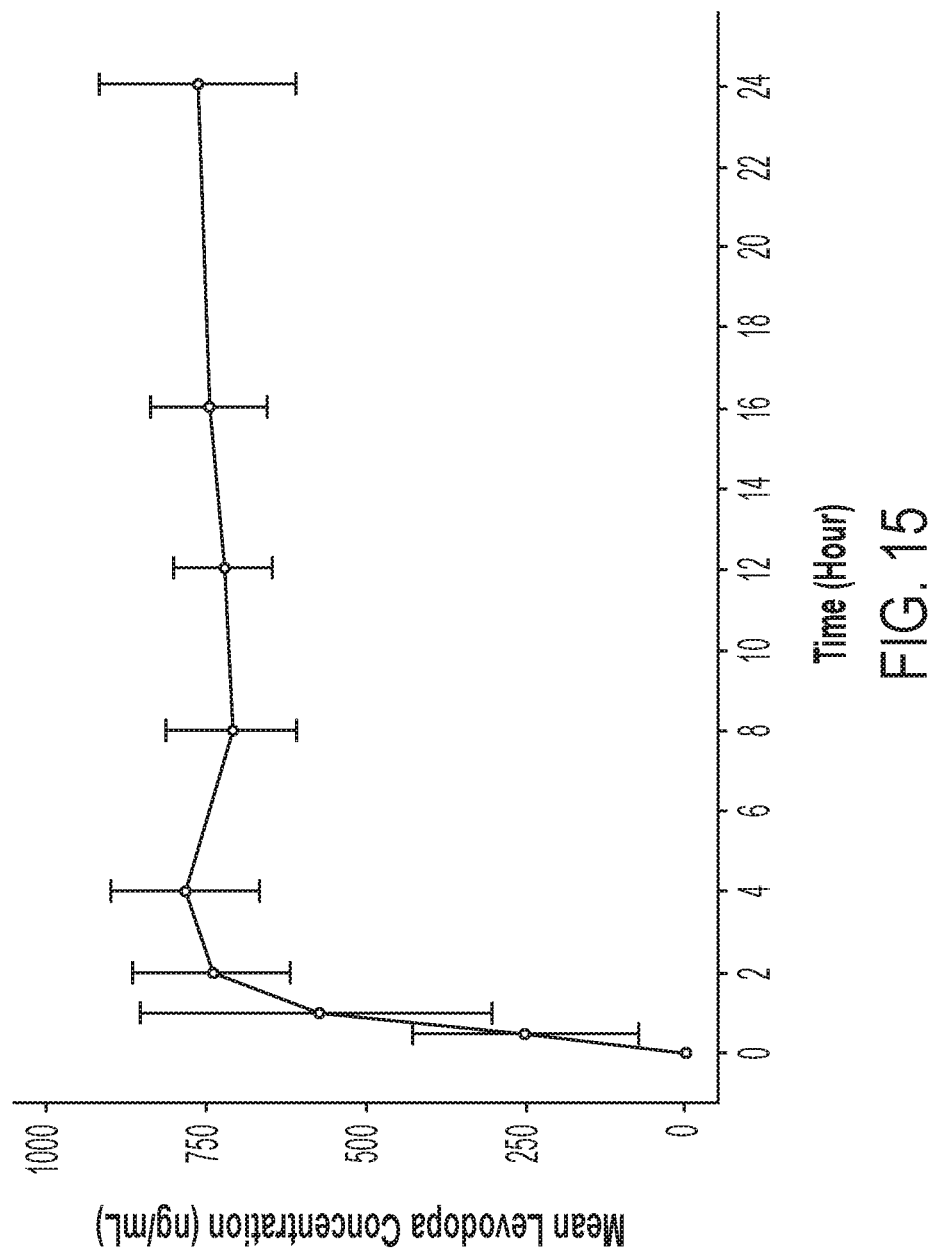
FIG. 15 is a plasma time-concentration profile of levodopa plasma levels (±standard deviation) in healthy human volunteers after subcutaneous administration of a bolus dose of a pharmaceutical composition of levodopa 4'-monophosphate and carbidopa 4'-monophosphate at a ratio of 20:1 followed by a continuous subcutaneous dose of the pharmaceutical composition for 24 hours (Clinical Study B).

The pharmaceutical composition prodrug was administered subcutaneously to 8 healthy volunteers (45-75 years) for 24 hours in an open label study. The dosing consisted of 100 mg levodopa phosphate loading dose followed by a continuous steady infusion of 850 mg levodopa phosphate over 24-hour period. All the infusions of the pharmaceutical composition were administered to the subcutaneous space in the abdomen. During and following infusion of the pharmaceutical composition, serial plasma samples were collected to assay for levodopa and carbidopa. Levodopa and carbidopa pharmacokinetic data from a previous Duopa phase 1 study (Nyholm, D., et al. AAPS Journal 2013; 15-2: 316-329) was used to compare pharmacokinetic data between the present pharmaceutical composition and Duopa. Safety and tolerability including local adverse events (AEs) related to the subcutaneous infusion site were assessed throughout the study. Following administration of the pharmaceutical composition, levodopa mean pharmacokinetic profile over initial 16 hours is similar to previous Duodopa phase 1 study (Nyholm, D., et al. AAPS Journal 2013; 15-2: 316-329) in Parkinson's Disease patients (FIGS. 15 and 16).

Results

Figure 17:
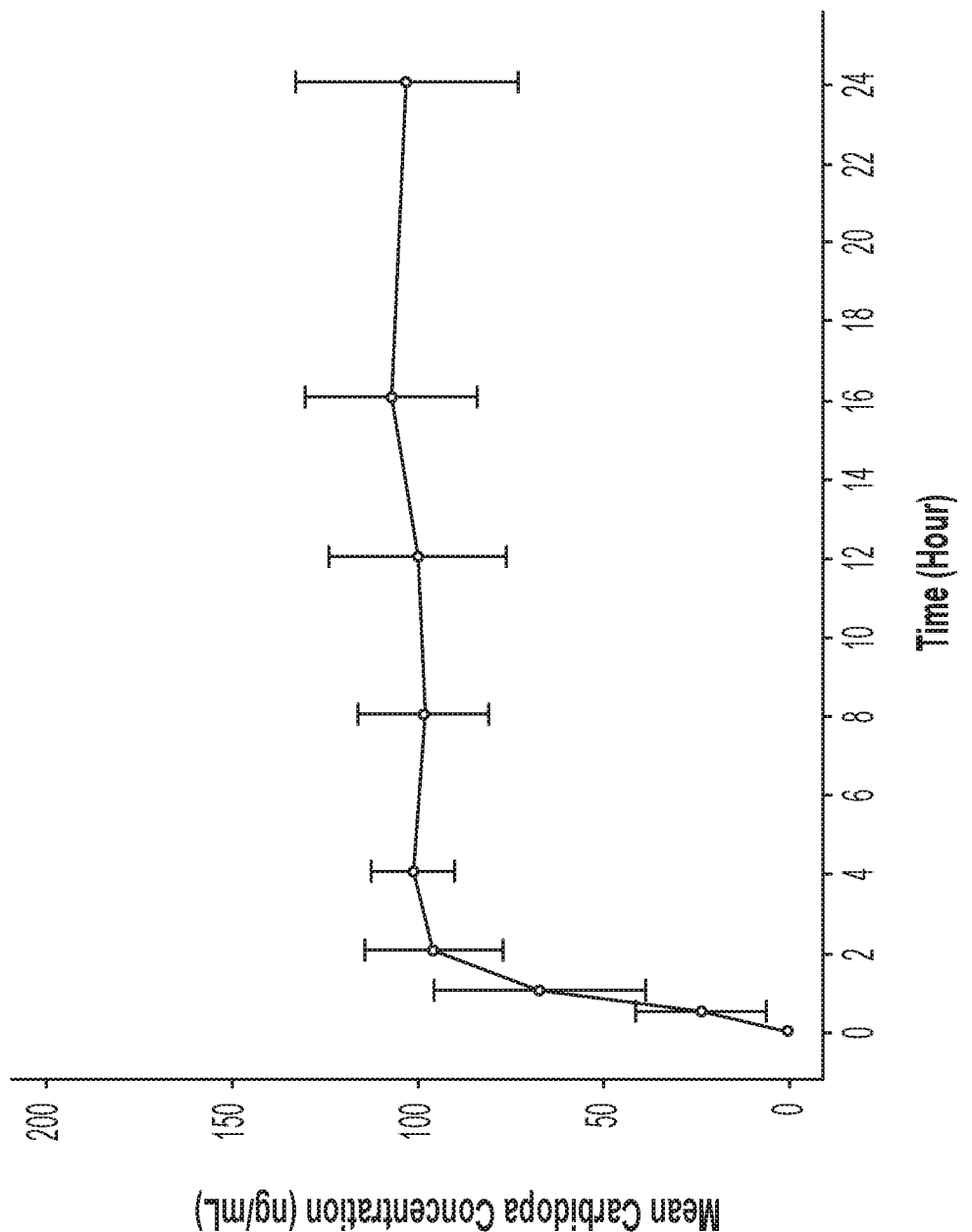
FIG. 17 is a plasma time-concentration profile of carbidopa plasma levels (±standard deviation) in healthy human volunteers after subcutaneous administration of a bolus dose of a pharmaceutical composition of levodopa 4'-monophosphate and carbidopa 4'-monophosphate at a ratio of 20:1 followed by a continuous subcutaneous dose of the pharmaceutical composition for 24 hours (Clinical Study B).
Figure 18:
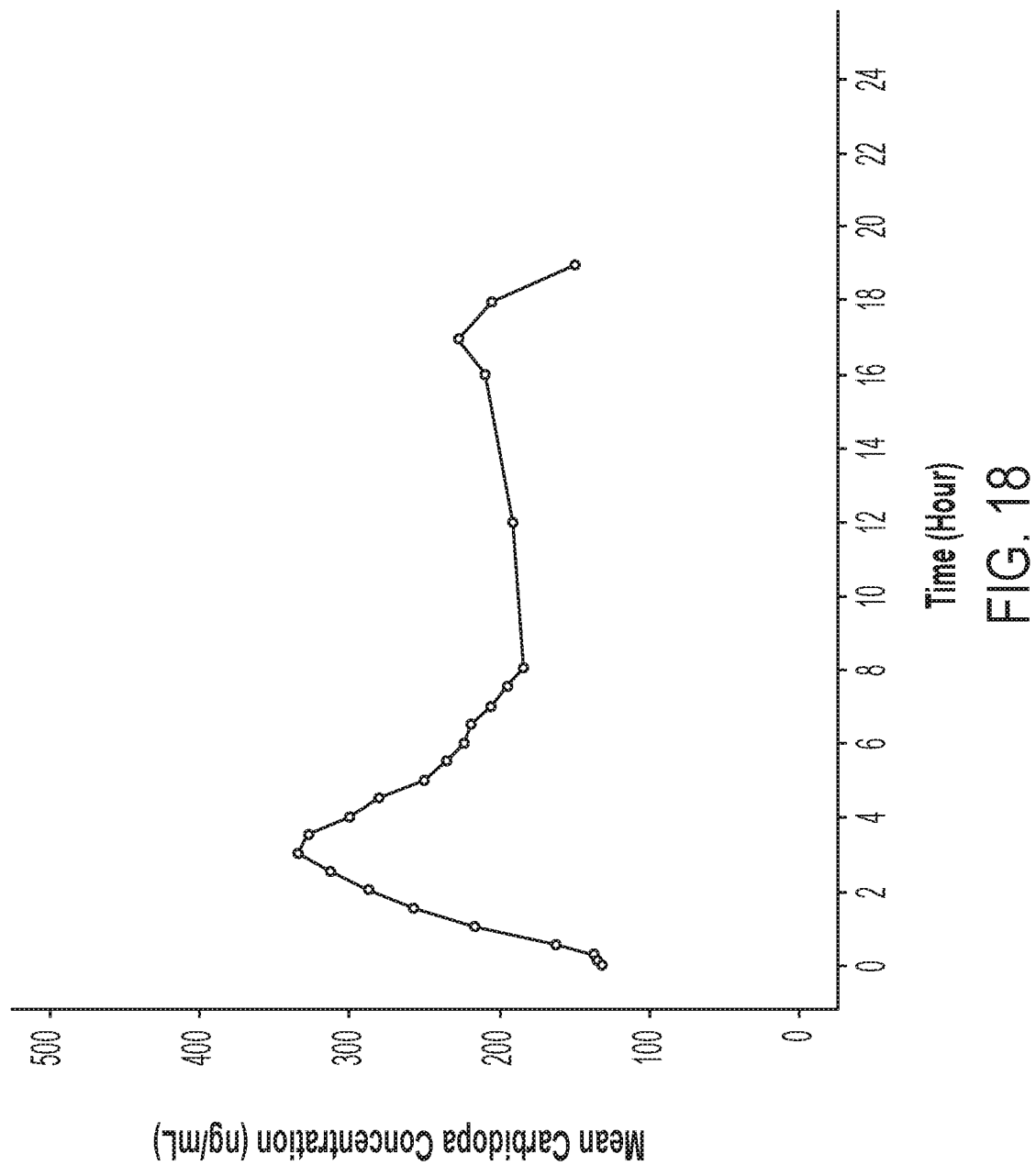
FIG. 18 is a plasma time-concentration profile of carbidopa levels in human patients after intestinal administration of Duodopa® at a ratio of levodopa to carbidopa of 4:1 over 24 hours.

During and following administration of the pharmaceutical composition, it was found that a carbidopa mean pharmacokinetic profile in healthy human volunteers over initial 16 hours provides a pharmacokinetic profile with less fluctuation than a previous Duodopa phase 1 study (Nyholm, D., et al. AAPS Journal 2013; 15-2: 316-329) in Parkinson' disease patients (FIGS. 17 and 18). Levodopa and carbidopa pharmacokinetic parameters following infusion of the pharmaceutical composition are presented in Table 20.

TABLE 20

Levodopa and carbidopa pharmacokinetic parameters following infusion of the aqueous pharmaceutical composition in healthy human volunteers

| | | Pharmacokinetic Parameter | |
|---|---|---|---|
| | Units | Levodopa Geometric Mean (% CV) | Carbidopa Geometric Mean (% CV) |
| $C_{max}$ | ng/mL | 836 (20) | 103 (15) |
| $T_{max}$[a] | hr | 20 [1-24] | 20 [1-24] |
| $t_{1/2}$[b] | hr | 1.7 (20) | 2.4 (29) |
| $AUC_t$ | ng*hr/mL | 19100 (16) | 2410 (15) |
| $AUC_{inf}$ | ng*hr/mL | 19200 (16) | 2500 (16) |

[a]Median [Minimum-Maximum]
[b]Harmonic mean (pseudo % CV)

Following infusion of the pharmaceutical composition, due to low variability in levodopa concentration level, the $T_{max}$ range was 1 to 24 hours demonstrating that the $C_{max}$ can occur at any point during the infusion. The degree of fluctuation ($[C_{max}-C_{min}]/C_{ave}$) is often used to quantify pharmacokinetic fluctuation. Following administration pharmaceutical composition appeared to have a lower degree of fluctuation to Duodopa data previously reported (Nyholm, D., et al. AAPS Journal 2013; 15-2: 316-329) for both levodopa and carbidopa (Table 21).

TABLE 21

Mean Levodopa and Carbidopa Degree of Fluctuation Parameter (±SD) following administration of Aqueous Pharmaceutical Composition and Duodopa

| | Pharmacokinetic Parameters | |
|---|---|---|
| | Composition A (N = 8) (healthy human volunteers) | Duopa (N = 18) (patients) |
| Levodopa Degree of fluctuation (2-16 hours) | 0.11 ± 0.02 | 0.52 ± 0.20 |
| Carbidopa Degree of fluctuation (2-16 hours) | 0.08 ± 0.05 | 0.96 ± 0.49 |

Following the study, the results were analyzed. Five subjects reported at least one adverse event. Mild infusion site reactions and injection site irritation were observed in a few subjects. All adverse events were transient and did not cause discontinuation from the study and there was no nodule formation at the infusion site.

The pharmaceutical composition was able to provide stable levodopa and carbidopa exposures over 24 hours via the subcutaneous route of delivery with very low fluctuation in levodopa concentration level. The pharmaceutical composition had a favorable safety profile.

Example 7

In order to characterize pharmacokinetics and safety and tolerability of an aqueous pharmaceutical composition comprising levodopa 4'-monophosphate prodrug corresponding in structure to formula (A-1) and carbidopa 4'-monophosphate prodrug corresponding in structure to formula (B-1) (the prodrug combination) administered at different sites, the pharmaceutical composition was administered at three infusion sites: the abdomen, arm and thigh of healthy volunteers.

Methods

The pharmaceutical composition was administered subcutaneously to 12 healthy volunteers (45-75 years) for 24 hours at the three subcutaneous infusion sites: abdomen, arm, and thigh in a randomized crossover design. The dosing consisted of 960 mg of the levodopa 4'-monophosphate prodrug corresponding in structure to formula (A-1) delivered at a steady rate over a 24-hours period at each infusion site. A minimum washout period of 24 hours between the end of the infusion of the pharmaceutical composition and the start of the next infusion of the pharmaceutical composition was incorporated. Following infusion of the pharmaceutical composition, serial plasma samples were collected to assay for levodopa and carbidopa. Safety and tolerability including local adverse events related to the subcutaneous infusion site were assessed throughout the study.

Results

Figure 19:
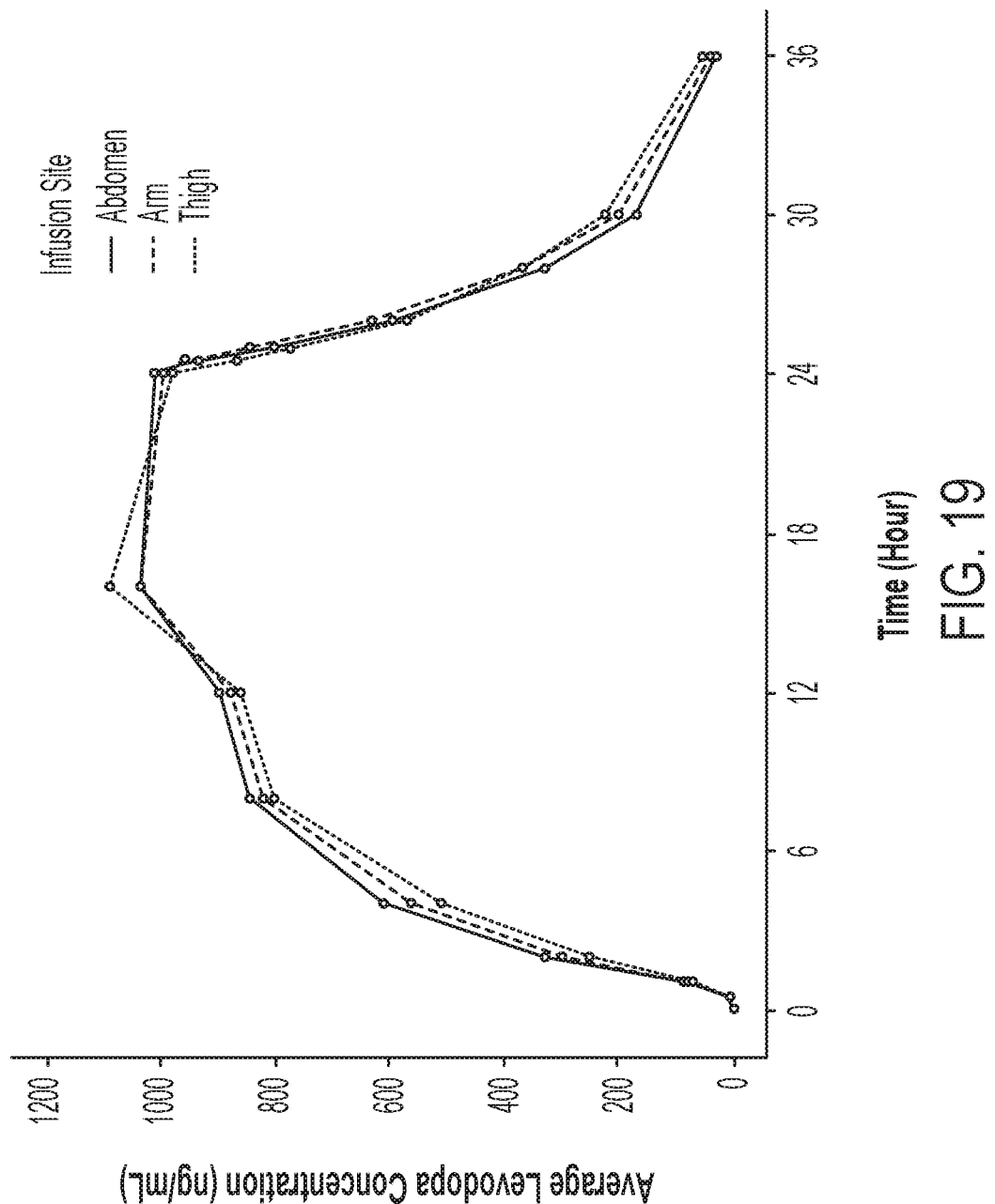
FIG. 19 is a graph comparing the mean levodopa pharmacokinetic profile following subcutaneous infusion to the abdomen, arm, and thigh (Clinical Study B) in healthy human volunteers.
Figure 20:
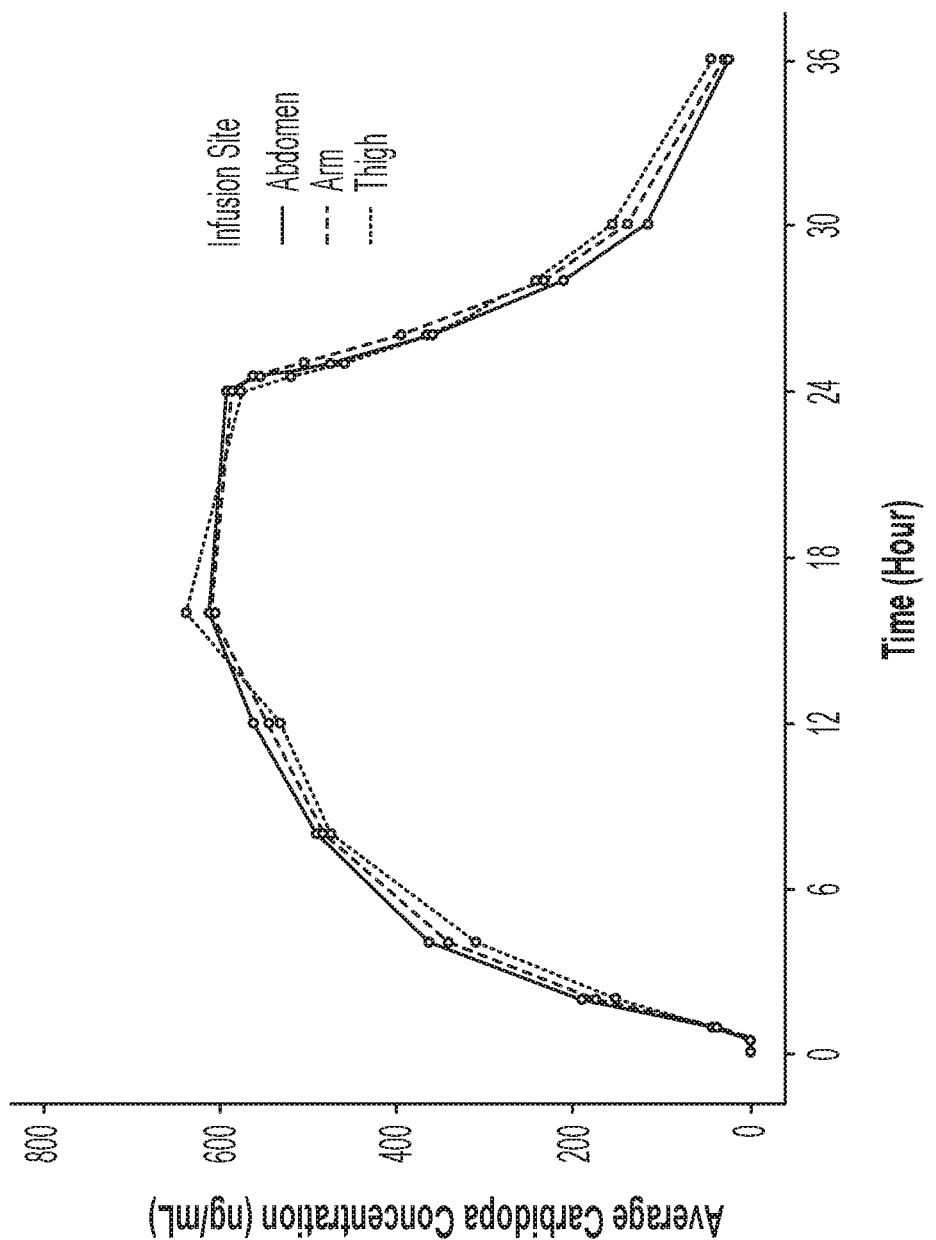
FIG. 20 is a graph comparing the mean carbidopa pharmacokinetic profile following subcutaneous infusion to the abdomen, arm, and thigh (Clinical Study B) in healthy human volunteers.

During and following administration of the pharmaceutical composition, both the levodopa and carbidopa mean PK profiles appeared to be similar between the three subcutaneous infusion sites (FIGS. 19 and 20). The levodopa and carbidopa PK parameters following infusion of the pharmaceutical composition at different subcutaneous infusion sites are presented in Table 22.

TABLE 22

Geometric Mean (% CV) Levodopa and Carbidopa PK Parameters Following 24-hour Subcutaneous Infusion of the Aqueous Pharmaceutical Composition in Healthy Human Volunteers

|  | Units | Abdomen | Arm | Thigh |
|---|---|---|---|---|
| Levodopa Pharmacokinetic Parameters |  |  |  |  |
| $C_{max}$ | ng/mL | 1030 (25) | 1030 (28) | 1080 (27) |
| $T_{max}{}^a$ | h | 16.0 (16.0-24.0) | 26.0 (12.0-24.5) | 16.0 (16.0-24.0) |
| $AUC_t$ | ng-h/mL | 22600 (25) | 22600 (25) | 22500 (23) |
| $AUC_\infty$ | ng-h/mL | 22700 (25) | 22800 (25) | 22800 (23) |
| $T_{1/2}{}^b$ | h | 2.30 (0.248) | 2.35 (0.343) | 2.70 (0.633) |
| Carbidopa Pharmacokinetic Parameters |  |  |  |  |
| $C_{max}$ | ng/mL | 611 (27) | 607 (27) | 629 (29) |
| $T_{max}{}^a$ | h | 16.0 (12.0-24.0) | 16.0 (12.0-24.5) | 16.0 (16.0-24.0) |
| $AUC_t$ | ng-h/mL | 13600 (26) | 13600 (26) | 13600 (26) |
| $AUC_\infty$ | ng-h/mL | 13700 (26) | 13700 (26) | 13800 (125) |
| $T_{1/2}{}^b$ | h | 2.52 (0.298) | 2.54 (0.345) | 3.02 (0.797) |

$^a$Median (minimum through maximum)
$^b$Harmonic mean (pseudo-standard deviation)

The results shown in Table 22 and FIG. 19 show that following administration of the pharmaceutical composition, the levodopa mean PK profile is similar between the three subcutaneous infusion sites (abdomen, arm, and thigh). In addition, the results shown in Table 22 and FIG. 20 show that following administration of pharmaceutical composition, the carbidopa mean PK profile is similar between the three subcutaneous infusion sites (abdomen, arm, and thigh). The results show that pharmaceutical composition has comparable levodopa and carbidopa exposures when infused to different infusion sites. In addition, it was observed that the infusion of the pharmaceutical composition was well tolerated with no notable pattern in adverse events profile across the three different infusion sites. All adverse events were mild and did not cause discontinuation from the study. Based on these results, patients have alternative subcutaneous infusion site option for administering the pharmaceutical composition. It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof

What is claimed is:

1. A method of treating Parkinson's disease in a subject, comprising continuously subcutaneously administering a therapeutically effective amount of an aqueous pharmaceutical composition comprising:
about 240 mg/mL of a compound of formula:

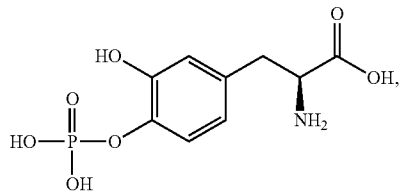

(A-1)

and about 12 mg/mL of a compound of formula:

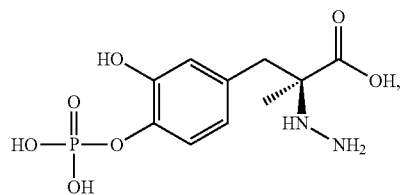

(B-1)

wherein the weight to weight ratio of compound (A-1) to compound (B-1) is about 20:1; and
wherein said therapeutically effective amount is an amount which, when continuously subcutaneously administered to a population of Parkinson's disease patients, achieves a mean plasma concentration of levodopa having a degree of fluctuation of about 0.3 or less over a time period of 2-16 hours following administration, wherein the degree of fluctuation is defined as the $([C_{max}-C_{min}/C_{ave}])$ for the given time period, and wherein said Parkinson's disease is treated.

2. The method of claim 1, wherein the pharmaceutical composition has a pH of between about 6.5 and about 9.2.

3. The method of claim 2, wherein the pharmaceutical composition has a pH of about 7.4.

4. The method of claim 3, wherein the pharmaceutical composition does not comprise an antioxidant.

5. The method of claim 3, wherein the mean plasma concentration of levodopa has a degree of fluctuation of about 0.40 over 2-72 hours following administration.

6. The method of claim 3, wherein the subject is treated for at least 10 days with no incidence of developing skin nodules.

7. The method of claim 3, wherein said therapeutically effective amount is an amount which, when continuously subcutaneously administered to the population of Parkinson's disease patients, provides a mean plasma exposure ratio of levodopa to carbidopa between 6.57 and 8.03 levodopa to about 1 carbidopa as measured by $AUC_{(0-t)}$ to $AUC_{(0-t)}$.

8. The method of claim 1, wherein said method improves a Movement Disorder Society-Unified Parkinson's Disease Rating Scale (MDS-UPDRS) total score in the subject, wherein the subject has a baseline MDS-UPDRS score, and said method reduces the baseline MDS-UPDRS total score by at least 9 units;

thereby improving the (MDS-UPDRS) total score.

9. The method of claim 8, wherein the pharmaceutical composition has a pH of between about 6.5 and about 9.2.

10. The method of claim 9, wherein the pharmaceutical composition has a pH of about 7.4.

11. The method of claim 10, wherein the pharmaceutical composition does not comprise an antioxidant.

12. The method of claim 10, wherein the subject is treated for at least 10 days with no incidence of developing skin nodules.

13. The method of claim 10, wherein said therapeutically effective amount is an amount which, when continuously subcutaneously administered to a population of Parkinson's disease patients, provides a mean plasma exposure ratio of levodopa to carbidopa between 6.57 and 8.03 levodopa to about 1 carbidopa as measured by $AUC_{(0-t)}$ to $AUC_{(0-t)}$.

14. The method of claim 1, wherein said method improves sleep in a subject having a baseline Parkinson's Disease Sleep Scale-2 (PDSS-2) total score by at least 2 units;

thereby improving said sleep.

15. The method of claim 14, wherein the pharmaceutical composition has a pH of between about 6.5 and about 9.2.

16. The method of claim 15, wherein the pharmaceutical composition has a pH of about 7.4.

17. The method of claim 16, wherein the pharmaceutical composition does not comprise an antioxidant.

18. The method of 16, wherein the subject is treated for at least 10 days with no incidence of developing skin nodules.

19. The method of claim 16, wherein said therapeutically effective amount is an amount which, when continuously subcutaneously administered to a population of Parkinson's disease patients, provides a mean plasma exposure ratio of levodopa to carbidopa between 6.57 and 8.03 levodopa to about 1 carbidopa as measured by $AUC_{(0-t)}$ to $AUC_{(0-t)}$.

20. A method of reducing motor fluctuations in a patient with Parkinson's disease comprising subcutaneously administering a therapeutically effective amount of an aqueous pharmaceutical composition comprising:

about 240 mg/mL of a compound of formula:

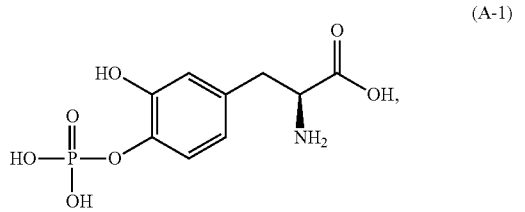 [SMILES: N[C@@H](Cc1ccc(OP(=O)(O)O)c(O)c1)C(=O)O]

(A-1)

and about 12 mg/mL of a compound of formula:

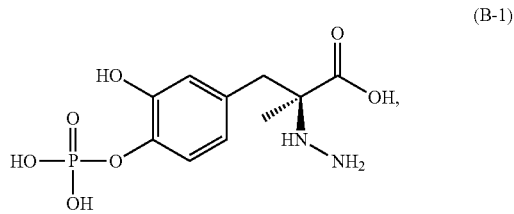 [SMILES: C[C@@](Cc1ccc(OP(=O)(O)O)c(O)c1)(NN)C(=O)O]

(B-1)

wherein the weight to weight ratio of compound (A-1) to compound (B-1) is about 20:1; and wherein said therapeutically effective amount is an amount which, when continuously administered to a population of Parkinson's disease patients, achieves an average percent improvement in off time from baseline of about 46%, thereby reducing the motor fluctuations.

21. The method of claim 20, wherein the pharmaceutical composition has a pH of between about 6.5 and about 9.2.

22. The method of claim 21, wherein the pharmaceutical composition has a pH of about 7.4.

23. The method of claim 22, wherein the pharmaceutical composition does not comprise an antioxidant.

24. The method of claim 22, wherein said effective amount is an amount which, when continuously subcutaneously administered to the population of Parkinson's disease patients, achieves a mean plasma concentration of levodopa having a degree of fluctuation of about 0.40 over a time period of 2-72 hours following administration, wherein the degree of fluctuation is defined as the $([C_{max}-C_{min}]/C_{ave})$ for the given time period.

25. The method of claim 22, wherein the subject is treated for at least 10 days with no incidence of developing skin nodules.

26. The method of claim 22, wherein said effective amount is an amount which, when continuously subcutaneously administered to the population of Parkinson's disease patients, provides a mean plasma exposure ratio of levodopa to carbidopa between 6.57 and 8.03 levodopa to about 1 carbidopa as measured by $AUC_{(0-t)}$ to $AUC_{(0-t)}$.

27. The method of claim 20, wherein said method improves quality of life in a subject having a baseline Parkinson's Disease Questionnaire-39 items (PDQ-39) summary index score by at least 6.9 units;

thereby reducing the baseline PDQ-39 score by at least 6.9 units.

28. The method of claim 27, wherein the pharmaceutical composition has a pH of between about 6.5 and about 9.2.

29. The method of claim 28, wherein the pharmaceutical composition has a pH of about 7.4.

30. The method of claim 29, wherein the pharmaceutical composition does not comprise an antioxidant.

31. The method of 29, wherein the subject is treated for at least 10 days with no incidence of developing skin nodules.

32. The method of claim 29, wherein said therapeutically effective amount is an amount which, when continuously subcutaneously administered to a population of Parkinson's disease patients, provides a mean plasma exposure ratio of levodopa to carbidopa between 6.57 and 8.03 levodopa to about 1 carbidopa as measured by $AUC_{(0-t)}$ to $AUC_{(0-t)}$ when administered to adult humans.

33. A method for treatment of motor fluctuations in patients with Parkinson's disease, comprising continuously subcutaneously administering to said patients a therapeutically effective amount of an aqueous pharmaceutical composition which comprises a combination of a compound of formula:

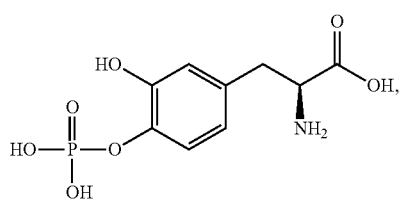

(A-1)

and a compound of formula:

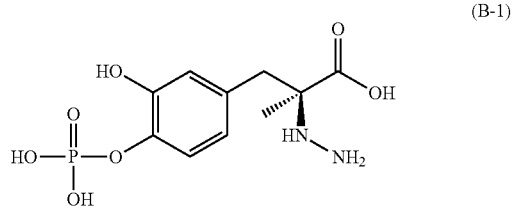 [SMILES: C[C@@](Cc1ccc(OP(=O)(O)O)c(O)c1)(NN)C(=O)O]

(B-1)

wherein the weight to weight ratio of compound (A-1) to compound (B-1) is about 20:1, thereby treating said motor fluctuations; and wherein the pharmaceutical composition has a pH of about 7.4.

34. The method of claim 33, wherein said treatment is safe.

35. The method of claim 34, wherein said treatment is a statistically significant treatment capable of generating statistically significant changes in clinical outcome from baseline in said patients.

36. The method of claim 33, wherein said pharmaceutical composition comprises about 240 mg of compound (A-1) and about 12 mg of compound (B-1).

* * * * *

UNITED STATES PATENT AND TRADEMARK OFFICE
CERTIFICATE OF CORRECTION

PATENT NO. : 12,251,365 B2
APPLICATION NO. : 16/684874
DATED : March 18, 2025
INVENTOR(S) : Ehab Moussa et al.

Page 1 of 1

It is certified that error appears in the above-identified patent and that said Letters Patent is hereby corrected as shown below:

On the Title Page

Under (73) "Assignees," please remove the following Assignee:
"AbbVie Deutschland Gmbh & Co. KG, Wiesbaden (DE)"

Signed and Sealed this
Fifteenth Day of April, 2025

Coke Morgan Stewart
*Acting Director of the United States Patent and Trademark Office*